US012736541B2

(12) United States Patent
Zhao et al.

(10) Patent No.: US 12,736,541 B2
(45) Date of Patent: Sep. 15, 2026

(54) TARGET-BASED METHOD FOR HIGH-THROUGHPUT AND SUBCLASS SPECIFIC IgG GLYCAN PROFILING IN HUMAN PLASMA

(71) Applicant: Regeneron Pharmaceuticals, Inc., Tarrytown, NY (US)

(72) Inventors: Yunlong Zhao, Scarsdale, NY (US); Shivkumar Raidas, New City, NY (US); Yuan Mao, Hartsdale, NY (US); Ning Li, New Canaan, CT (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 109 days.

(21) Appl. No.: 18/414,536

(22) Filed: Jan. 17, 2024

(65) Prior Publication Data

US 2024/0353417 A1 Oct. 24, 2024

Related U.S. Application Data

(60) Provisional application No. 63/451,113, filed on Mar. 9, 2023, provisional application No. 63/439,929, filed on Jan. 19, 2023.

(51) Int. Cl.

*G01N 33/68* (2006.01)
*G01N 30/72* (2006.01)
*G01N 30/02* (2006.01)

(52) U.S. Cl.

CPC ..... *G01N 33/6848* (2013.01); *G01N 30/7266* (2013.01); *G01N 2030/027* (2013.01); *G01N 2440/38* (2013.01)

(58) Field of Classification Search

None

See application file for complete search history.

(56) References Cited

U.S. PATENT DOCUMENTS

2016/0217994 A1* 7/2016 Oleschuk .............. H01J 49/165
2019/0101544 A1* 4/2019 Danan-Leon ...... G01N 33/6857
2021/0239661 A1 8/2021 Wang

OTHER PUBLICATIONS

Hong et al., Journal of Proteome Research, vol. 14, pp. 5179-5192; with Supporting Information, pp. S1-S17 (Year: 2015).*

Zhou Shiyue et al: . "Quantitation of PermethylatedN-Glycans through Multiple-Reaction Monitoring (MRM) LC-MS/MS", Journal of the American Society for Mass Spectrometry, Elsevier Science Inc, US, vol. 26, No. 4, Feb. 20, 2015 (Feb. 20, 2015), pp. 596-603, XP035469428, ISSN: 1044-0305, DOI: 10.1007/S13361-014-1054-1 [retrieved on Feb. 20, 2015] p. 596, 597, 602.

Hong Qiuting et al: "A Method for Comprehensive Glycosite-Mapping and Direct Quantitation of Serum Glycoproteins", Journal of Proteome Research, vol. 14, No. 12, Nov. 9, 2015 (Nov. 9, 2015), pp. 5179-5192, XP055835324, ISSN: 1535-3893, DOI:10.1021/acs.jproteome.5b00756, p. 5179-p. 5180.

Plomp Rosina et al: "Recent Advances in Clinical Glycoproteomics of Immunoglobulins (Igs)", Molecular & Cellular Proteomics, vol. 15, No. 7, Mar. 23, 2016 (Mar. 23, 2016), pp. 2217-2228, XP093109810, US ISSN: 1535-9476, DOI:10.1074/mcp.0116.058503 Retrieved from the Internet:URL:https://www.ncbi.nlm.nih.gov/pmc/articles/PMC4937499/pdf/zjw2217.pdp p. 2218, 2219, 2221.

Roy Rini et al: "Absolute Quantitation of Glycoforms of Two Human IgG Subclasses Using Synthetic Fc Peptides and Glycopeptides", Journal of the American Society for Mass Spectrometry, Elsevier Science Inc, US, vol. 29, No. 6, May 23, 2018 (May 23, 2018), pp. 1086-1098, XP036809810, ISSN: 1044-0305, DOI: 10.1007/S13361-018-1900-7 [retrieved on May 23, 2018] p. 1097.

International Search Report and Written Opinion, International Application No. PCT/US2024/011738, International Filing Date Jan. 17, 2024, Date of Mailing Apr. 11, 2024.

* cited by examiner

*Primary Examiner* — Michelle F. Paguio Frising

(74) *Attorney, Agent, or Firm* — McCarter & English, LLP

(57) ABSTRACT

This application relates to methods for identifying a glycosylated peptide biomarker in a sample. In particular, the application relates to methods for identifying an N-glycan profile of a protein in a sample.

24 Claims, 51 Drawing Sheets

Retention Time

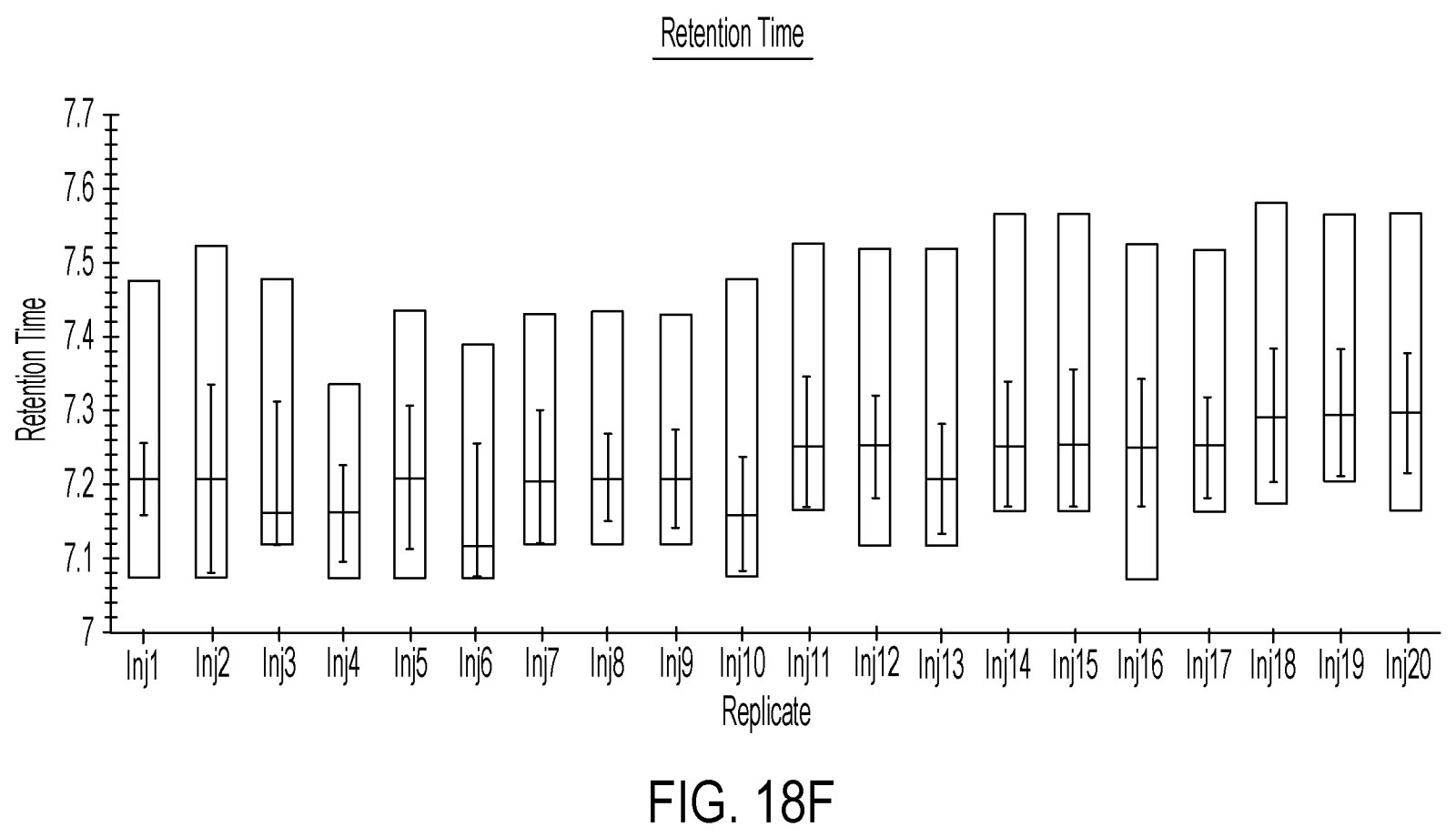

Retention Time 7.7
7.6
7.5
7.4
7.3
7.2
7.1
7

Inj1 Inj2 Inj3 Inj4 Inj5 Inj6 Inj7 Inj8 Inj9 Inj10 Inj11 Inj12 Inj13 Inj14 Inj15 Inj16 Inj17 Inj18 Inj19 Inj20

Replicate

FIG. 18F

TARGET-BASED METHOD FOR HIGH-THROUGHPUT AND SUBCLASS SPECIFIC IgG GLYCAN PROFILING IN HUMAN PLASMA

CROSS-REFERENCE TO RELATED APPLICATIONS

This application incorporates by reference and claims priority to and the benefit of U.S. Provisional Patent Application No. 63/439,929, filed on Jan. 19, 2023 and U.S. Provisional Patent Application No. 63/451,113 filed on Mar. 9, 2023.

REFERENCE TO ELECTRONIC SEQUENCE LISTING

This application contains a Sequence Listing which has been submitted electronically in .XML format and is hereby incorporated by reference in its entirety. Said .XML copy, created on Jul. 1, 2026, is named "135975-36903.xml" and is 83,405 bytes in size. The sequence listing contained in this .XML file is part of the specification and is hereby incorporated by reference herein in its entirety.

FIELD

This application relates to methods for identifying a glycosylated peptide biomarker in a sample. In particular, the application relates to methods for identifying an N-glycan profile of a protein in a sample.

BACKGROUND

Human immunoglobulins (IgG) consist of four subclasses (IgG1, IgG2, IgG3, and IgG4) at a wide range of concentrations in serum across different individuals. Although these subclasses share highly similar structures, differed only in the hinge region, each IgG subclass plays well-defined roles in unique physiological processes and response to different types of antigen. One of the major differences amongst IgG subclasses is the affinity to different Fc receptors and therefore the sensitivity to trigger different Fc receptor-mediated effector functions. For example, IgG1 and IgG3 can trigger many effector functions including antibody-dependent cellular cytotoxicity (ADCC) more readily compared to IgG2 and IgG4.

Human IgG subclasses share conserved amino acid sequence in the Fc region, including a single N-glycosylation site (N297). The Fc glycosylation is also crucial to the interaction between Fc and different types of receptors and therefore related to their biophysical profile such as lifetime and effector functions. For instance, antibodies with Fc-afucosylation exhibit stronger binding affinity to Fcγ receptor III and enhanced antibody-dependent cellular cytotoxicity (ADCC); Fc-galacosylation is associated with a strong binding affinity to C1q and enhanced complement-dependent cytotoxicity (CDC).

These synergetic contributions to biophysical functions by IgG subclass and N-linked Fc glycosylation profile have been considered during antibody-like drug development to achieve desired potency, pharmacokinetics, and effector functions, where specific IgG subtypes were selected (or engineered) to be a proper drug modality and the N-linked Fc-glycosylation was also engineered. In addition, subclass and glycosylation shift for endogenous human IgGs may be observed in aging and some abnormal physiology conditions such as autoimmune defect, tumor progression and metastasis, metabolic disorder, and pathogen infections. Therefore, subclass-specific IgG N-glycan profiling is highly demanded task during fundamental researches on disease mechanism as well as other clinical practices such as biomarker-based diagnosis and vaccine development.

IgG N-glycosylation profiling can be executed through well-established mass spectrometry-based methods, aiming at detection and quantification of the individual glycopeptides from the Fc region. Meanwhile, the protein level for each IgG subclass can also be estimated by summing up all major glycopeptides or using subclass-specific surrogate peptides. The peptide sequences covering the Fc N-glycosylation site are slightly different amongst four IgG subclasses and therefore they can be distinguished by accurate mass and/or separated by reverse phase chromatography. Although a glycopeptide can be simply quantified using extracted ion chromatogram (XIC) peaks for precursors from the full scan under data-dependent acquisition (DDA) mode, target-based methods were frequently carried on in recent IgG glycosylation profiling studies.

These methods are mainly based on MRM/PRM scans to monitor the product ions generated from the isolated precursors through glycosidic bond fragmentation, including released oxonium ions and Y series ions (intact peptide with residual saccharide units) for both better sensitivity and selectivity. Although these methods can effectively quantify glycosylation profiles of IgG1, IgG2 and total IgG3/IgG4, the only difference in Fc N-glycopeptide sequences of IgG3 (EEQFNSTYR)(SEQ ID NO: 1) and IgG4 (EEQYNSTFR) (SEQ ID NO: 2) is the swapped position of two amino acids, phenylalanine and tyrosine. This results in the same mass and coelution using existing separation methods, including reverse phase or hydrophilic interaction chromatography. Therefore, Fc glycopeptides from IgG3 and IgG4 are usually co-isolated in the target-based method and not distinguished by either precursor or the product ions generated by glycosidic bond fragmentation.

Consequently, it will be appreciated that a need exists for improved methods of IgG N-glycosylation profiling.

SUMMARY

In one embodiment, this disclosure provides a method for identifying a N-glycan profile of a protein in a sample, comprising: (a) contacting the sample with one or more proteases as to obtain a digested sample, wherein the digested sample comprises one or more peptides; (b) loading the digested sample with a liquid chromatography column to provide an eluent; (c) performing a multiple reaction monitoring on at least a portion of the eluent to obtain peptide backbone fragments using collision energy in a mass spectrometer; and (d) analyzing the peptide backbone fragments to identify the N-glycan profile of the protein.

In one aspect, the eluent is introduced in the mass spectrometer using a multi-nozzle electrospray emitter.

In another aspect, the multi-nozzle electrospray emitter has at least 5 channels.

In yet another aspect, the multi-nozzle electrospray emitter emits an electrospray of less than about 1 μL/min at a tip of each of the channels.

In another aspect, tips of each nozzle of the multi-nozzle electrospray emitter has a dimeter of about 10 μm.

In one aspect, the method further comprises denaturing the sample before contacting the sample with one or more proteases.

In one aspect, the method further comprises reducing the sample before contacting the sample with one or more proteases.

In one aspect, the method further comprises alkylating the sample before contacting the sample with one or more proteases.

In one aspect, the flowrate for the liquid chromatography column is about 5 μL/min.

In one aspect, the sample is at least about 5 μL in volume.

In one aspect, the method further comprises enriching the sample using affinity chromatography column prior to contacting the sample with one or more proteases.

In another aspect, the affinity chromatography column comprises immobilized protein A, immobilized protein G, or combination of immobilized protein A and immobilized protein G.

In another embodiment, this disclosure also provides a method for identifying a glycosylated peptide biomarker in a sample, comprising: (a) contacting the sample with one or more proteases as to obtain a digested sample, wherein the digested sample comprises one or more peptides; (b) loading the digested sample with a liquid chromatography column to provide an eluent; (c) performing a multiple reaction monitoring on at least a portion of the eluent to obtain peptide backbone fragments using collision energy in a mass spectrometer; and (d) analyzing the peptide backbone fragments to identify the glycosylated peptide biomarker.

In one aspect, the eluent is introduced in the mass spectrometer using a multi-nozzle electrospray emitter.

In another aspect, the multi-nozzle electrospray emitter has at least 5 channels.

In yet another aspect, the multi-nozzle electrospray emitter emits an electrospray of less than about 1 μL/min at a tip of each of the channels.

In another aspect, the tips of each nozzle of the multi-nozzle electrospray emitter has a dimeter of about 10 μm.

In one aspect, the method further comprises denaturing the sample before contacting the sample with one or more proteases.

In one aspect, the method further comprises reducing the sample before contacting the sample with one or more proteases.

In one aspect, the method further comprises alkylating the sample before contacting the sample with one or more proteases.

In one aspect, the flowrate for the liquid chromatography column is about 5 μL/min.

In one aspect, the sample is at least about 5 μL in volume.

In one aspect, the method further comprises enriching the sample using affinity chromatography column prior to contacting the sample with one or more proteases.

In yet another aspect, the affinity chromatography column comprises immobilized protein A, immobilized protein G, or combination of immobilized protein A and immobilized protein G.

BRIEF DESCRIPTION OF THE DRAWINGS

FIGS. 2B-1 and 2B-2 shows the mass spectrum of oxonium, b, y and Y (e.g., Y1, Y1* and other IgG1 N-glycopeptides with carbohydrate fragments) ions that derived from IgG1 N-glycopeptides (e.g., E-E-Q-Y-N-S-T-Y-R (SEQ ID NO: 3) with 4 N-acetylglucosamine/blue squares, 3 mannose/green circles and 1 fucose/red triangle), according to an exemplary embodiment.

FIGS. 9B-1, 9B-2 and 9B-3 shows the number of identified protein/peptide groups using the optimized MnESI-PRM method and nanoflow LC, according to an exemplary embodiment.

FIG. 18A-18F shows the absolute intensity of y4 ions and retention time for representative glycoforms of high abundance (FA2G1) and low abundance (A2G1) in IgG3 and IgG4 plotted from 20 continuous microflow LC-MnESI-PRM runs of pooled normal human serum digestion (Vendor 1), according to an exemplary embodiment.

DETAILED DESCRIPTION

Human immunoglobulins (IgG) consist of four subclasses (IgG1, IgG2, IgG3, and IgG4) at a wide range of concentrations in serum across different individuals. IgG1 and IgG2 are the most abundant subclasses followed by IgG3 and IgG4 in the normal human serum. Each IgG subclass plays a unique role in different physiological process, such as immune response, infectious disease and inflammation. Human IgG subclasses share a highly similar amino acid sequence in the fragment crystallizable (Fc) region, including a single conserved N-glycosylation site (N297).

Figure 1:
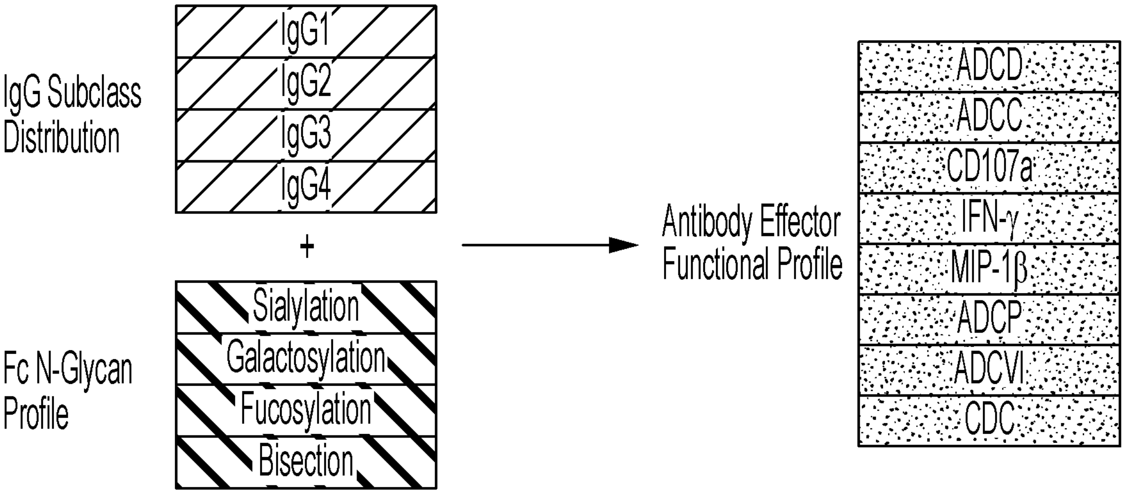
FIG. 1 shows that an IgG subclass distribution and their Fc N-glycan profiles determine an antibody effector functional profile, according to an exemplary embodiment.

FIG. 1 shows that the distribution of IgG subclasses and their N-glycan profiles to determine the antibody effector functional profile through interactions with various downstream effectors. For instance, antibodies with Fc-afucosylation exhibit stronger binding affinity to Fcγ receptor III and enhanced antibody-dependent cellular cytotoxicity (ADCC); Fc-galactosylation is associated with a strong binding affinity to C1q and enhanced complement-dependent cytotoxicity (CDC). On the other hand, due to different roles in physiological process, each IgG subclass also exhibits a different biophysical profile. These synergetic contributions to biophysical functions by IgG subclass and N-linked Fc glycosylation have been utilized during antibody-like drug development to achieve desired potency, pharmacokinetics and effector functions, where specific IgG subtypes were carefully selected as drug modality and the N-linked Fc-glycosylation was engineered.

The subclass and Fc N-glycan profile of endogenous human IgGs may be significantly altered in some abnormal physiology conditions, such as autoimmune defect, tumor progression and metastasis, and metabolic disorders. Therefore, subclass-specific IgG quantification and N-glycan profiling are important tasks during fundamental research on disease mechanism, as well as other clinical practices, such as biomarker-based diagnosis. Subclass-specific IgG quantification and N-glycan profiling can be used to support vaccine development and efficacy evaluation by generating vaccine-induced IgG pharmacokinetic (PK) and effector function profiles.

Figure 2A:
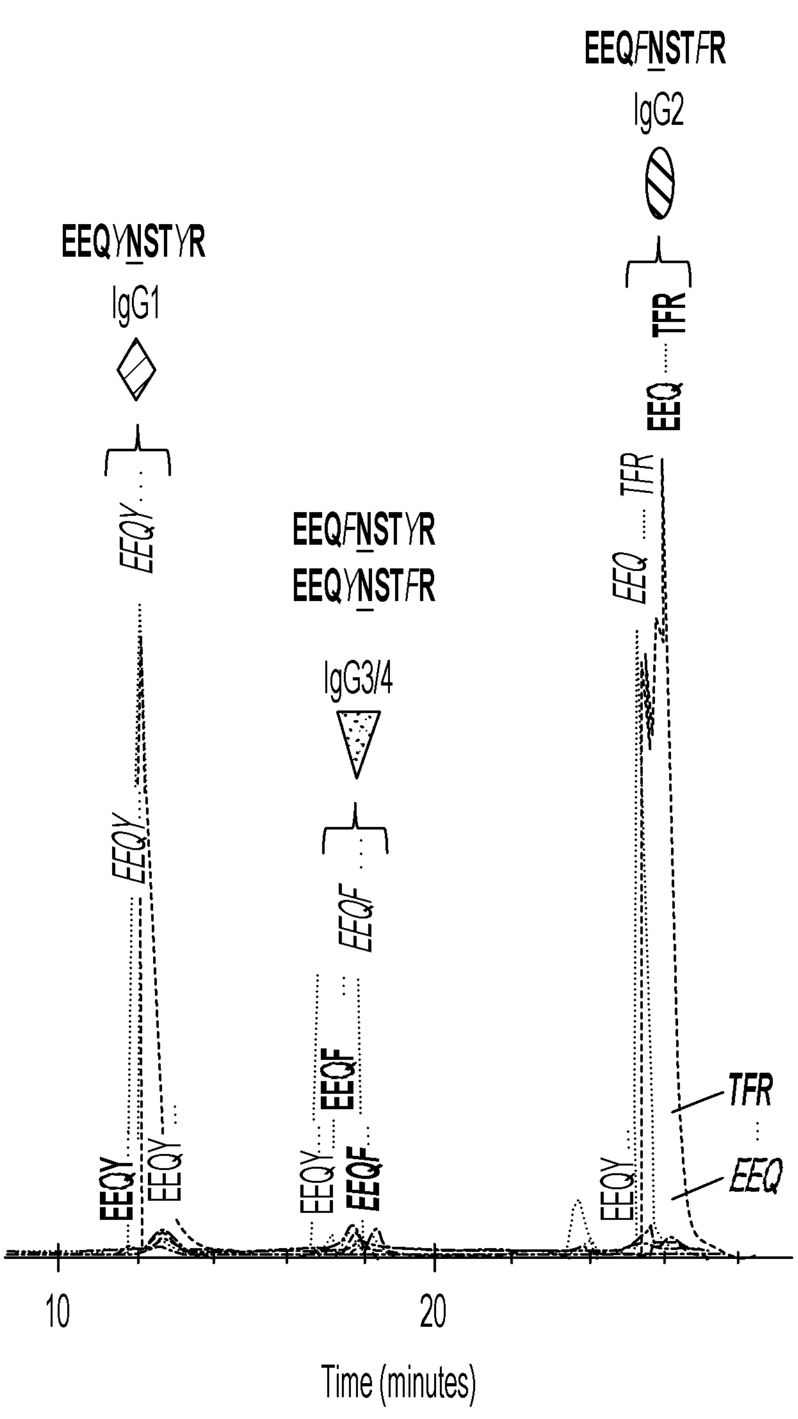
FIG. 2A shows the IgG N-glycopeptides for each subclass and their precursor ion peaks, according to an exemplary embodiment (EEQFNSTYR (SEQ ID NO: 1); EEQYNSTFR (SEQ ID NO: 2); EEQYNSTYR (SEQ ID NO: 3); EEQFNSTFR (SEQ ID NO: 10); EEQF (SEQ ID NO: 55); and EEQY (SEQ ID NO: 71).

IgG quantification and N-glycan profiling can be executed simultaneously through liquid chromatography-mass spectrometry (LC-MS)-based methods. LC-MS can quantify the glycopeptides containing the Fc N-glycosylation site of an IgG and determine a relative distribution of individual glycoforms. The total protein level can be estimated using summation of all IgG N-glycopeptides or an individual subclass-specific surrogate peptide. FIG. 2A shows that the IgG N-glycopeptides are slightly different. Therefore, the IgG N-glycopeptides can be separated and distinguished using reversed-phase chromatography (RPC) and accurate mass measurement, respectively.

A multi-nozzle emitter can split the low microflow stream (<5 μl/min) into 5-8 channels, and the electrospray ionization (ESI) at the tip of each channel can resemble the spray of nanoflow (<1 μl/min). Unlike an LC flow splitter coupled to a nanospray emitter, which diverts the majority of a stream into the waste, a multi-nozzle emitter may not reduce the amount of sample infused into the ESI source. Instead, a multi-nozzle emitter can significantly improve ionization efficiency. Compared to nanoflow LC, microflow LC can shorten an overall run time due to reduced dead volume. Additionally, increasing sample loading capacity using columns with a larger inner diameter (I.D.) can further improve the signal and alleviate carryover issues. Together, these features can make microflow LC methods high throughput and improve their robustness.

Figures 1, 2B:
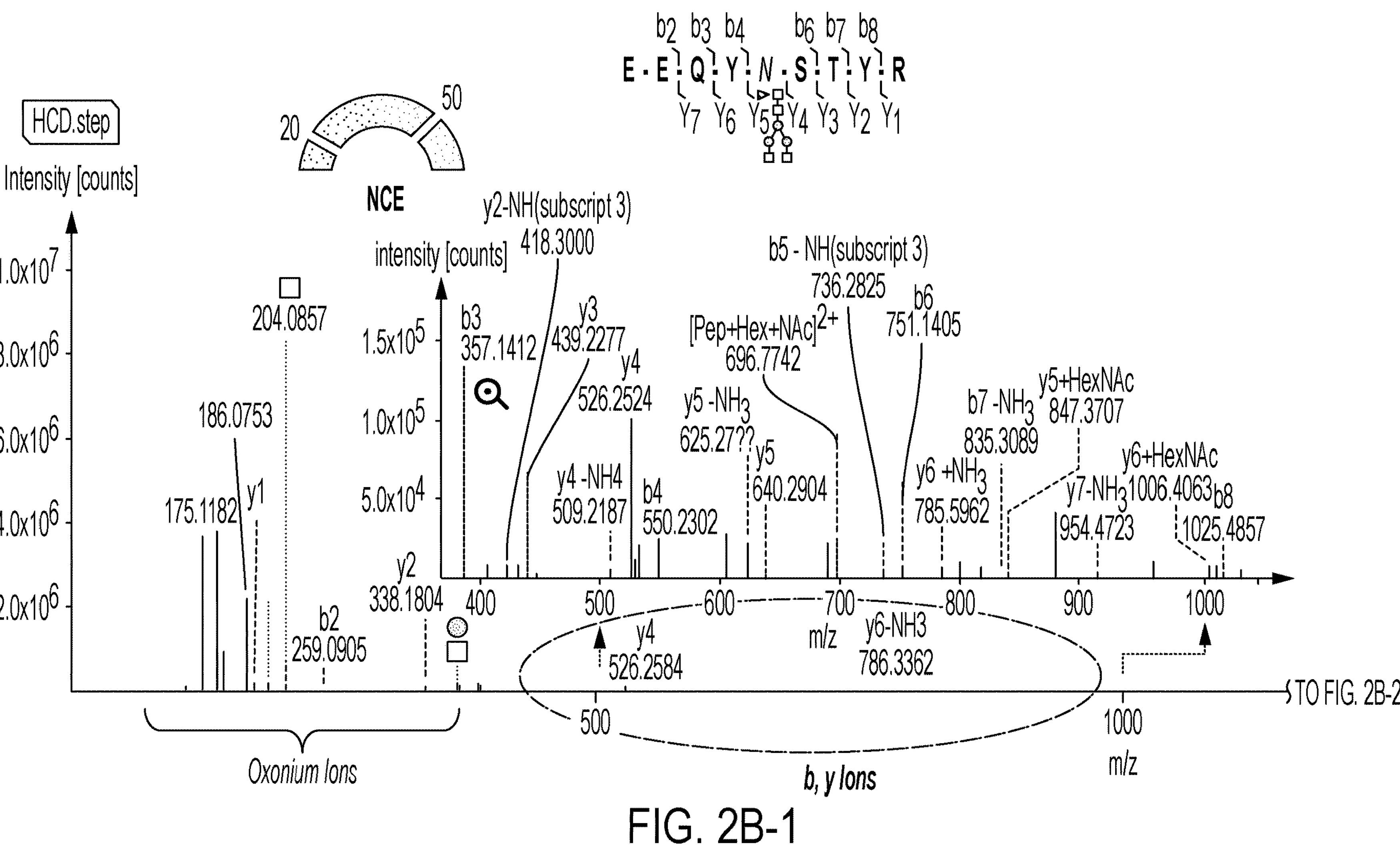
Figures 2, 2B:
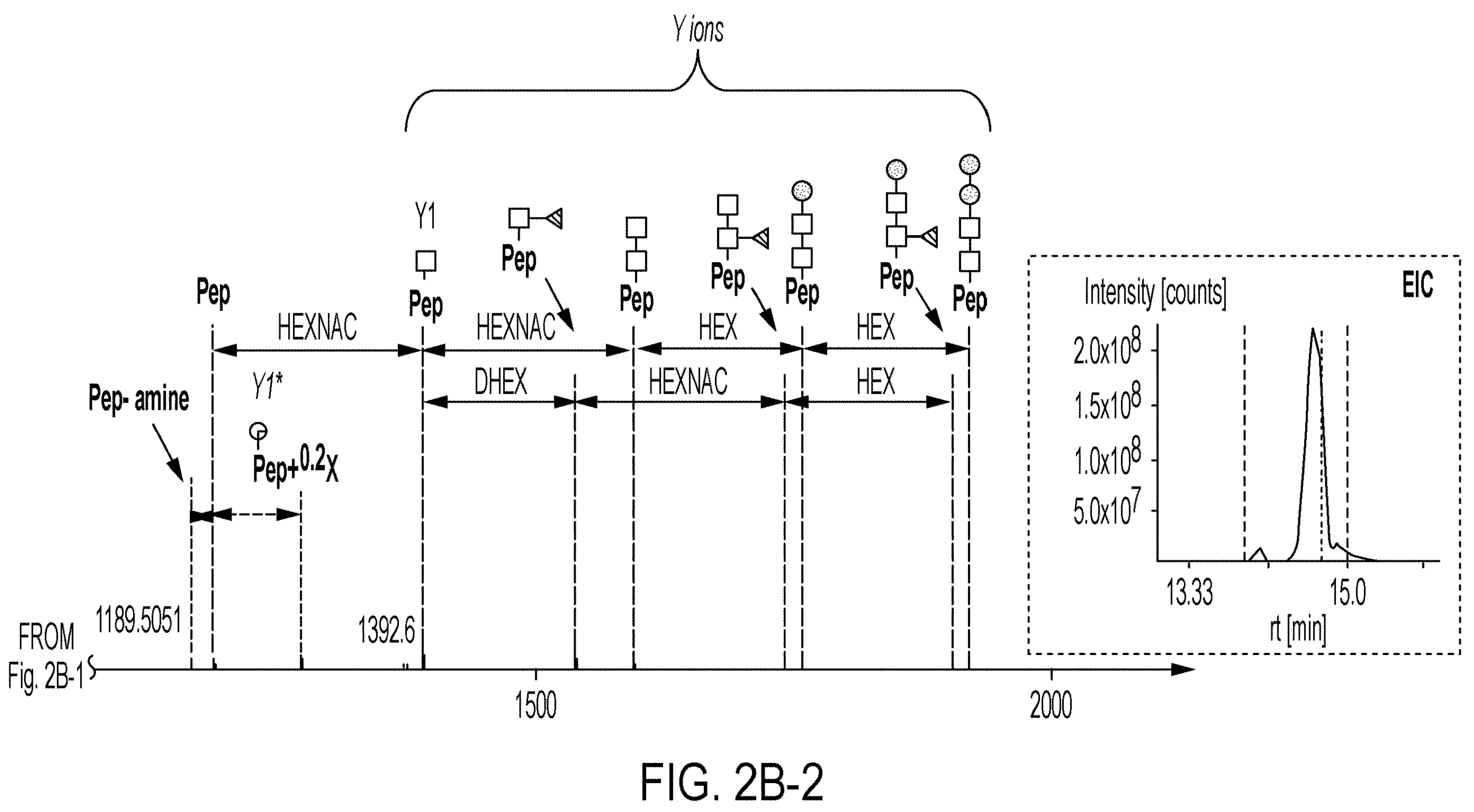

A conventional method for quantifying IgG Fc N-glycopeptides monitors the extracted ion chromatogram peaks of all precursor ions while performing a full scan in DDA mode. Conventional target-based methods for quantifying IgG Fc N-glycopeptides can monitor an isolated precursor ion using targeted selected ion monitoring (t-SIM) to improve the sensitivity of detection, or productions generated by glycan fragmentation (e.g., oxonium and Y1 ions) to improve the selectivity of detection. FIGS. 2B-1 and 2B-2 shows the product ions of an IgG1 N-glycopeptide, including oxonium ions/carbohydrate fragments (e.g., monosaccharides), b ions/peptide backbone fragments, y ions/peptide backbone fragments, and Y ions/glycopeptide fragments (e.g., Y1/peptide with N-acetylglucosamine, Y1*/peptide with cross-ring fragmented N-acetylglucosamine, and peptide with other carbohydrates).

FIG. 2A shows that the only difference between the IgG3 and IgG4 Fc N-glycopeptides is the position of a phenylalanine residue and a tyrosine residue. Accordingly, the IgG3 and IgG4 Fc N-glycopeptides have the same m/z ratio and may coelute using conventional separation methods, including RPC and hydrophilic interaction liquid chromatography (HILIC). Consequently, the IgG3 and IgG4 Fc N-glycopeptides always co-isolate using t-SIM and cannot be distinguished using the precursor or product ions generated by glycan fragmentation.

Immunoaffinity-based enrichment methods can use subclass-specific antibodies to provide IgG subclass-specific glycan profiling. FIGS. 2B-1 and 2B-2 shows that the b and y ions generated by peptide backbone fragmentation are much less abundant than the oxonium and Y ions. Thus, monitoring b and y product ions is not always practical. A peptide derivative approach can enhance the yield and detectability of peptide backbone fragment ions using electron transfer dissociation (ETD). For non-derived glycopeptides and a spectrum generated by higher energy collision dissociation (HCD), the most popular and robust fragmentation method, the instrument conditions need to be further optimized and developed.

Therefore, the present disclosure provides parallel reaction monitoring (PRM)-based methods for detecting the combined transitions generated from glycan and peptide backbone fragmentation and quantifying IgG Fc N-glycopeptides using a microflow LC platform coupled to a multi-nozzle electrospray emitter. The transitions generated from peptide backbone fragmentation enabled IgG3 and IgG4 subpopulations to be directly distinguished from each other due to their mass difference without requiring further enrichment of specific IgG subclass. Coupling the multi-nozzle electrospray emitter to capillary flow liquid chromatography improved the detection sensitivity for low-yield peptide backbone fragment ions and enhanced the method robustness. The gradients of exemplary embodiments were optimized to reduce the overall run time and make the method compatible with high throughput analysis. Exemplary embodiments of the disclosed methods used peptide backbone fragmentation to distinguish IgG3 and IgG4 glycosylation in IgG standard and commercially available human sera. Specifically, exemplary embodiments of the disclosed methods could effectively monitor twelve representative glycoforms of each IgG subclass, including IgG3 and IgG4, within a 20-minute run with a good detection limit and robustness.

Unless described otherwise, all technical and scientific terms used herein have the same meaning as commonly understood by one of ordinary skill in the art to which this invention belongs. Although practice or testing can use methods and materials similar or equivalent to those described herein, particular methods and materials are now described.

The terms "a" and "an" should be understood to mean "at least one" and the terms "about" and "approximately" should be understood to permit standard variation as would be understood by those of ordinary skill in the art and where ranges are provided, endpoints are included. As used herein, the terms "include," "includes," and "including" are meant to be non-limiting and are understood to mean "comprise," "comprises," and "comprising" respectively.

As used herein, the term "composition" refers to a pharmaceutical product formulated together with one or more pharmaceutically acceptable vehicles.

As used herein, the terms "pharmaceutical" and "pharmaceutical product" can include a biologically active component of a drug product. A pharmaceutical and a pharmaceutical product can refer to any substance or combination of substances used in a drug product, intended to furnish pharmacological activity or to otherwise have a direct or indirect effect on the diagnosis, cure, mitigation, treatment, or prevention of disease, or to have a direct or indirect effect in restoring, correcting or modifying physiological functions in animals. Non-limiting examples of a pharmaceutical or a pharmaceutical product can include a drug, a chemical compound, a nucleic acid, a nucleotide, a nucleoside, an oligonucleotide, a toxin, a peptide, a protein, a fusion protein, an antibody, an antibody fragment, a Fab region of an antibody, an scFv, a monoclonal antibody, a bispecific antibody, a multispecific antibody, an antibody-drug conjugate, or a pharmaceutical protein product, or combinations thereof. Non-limiting examples of processes or elements that can be used in a method of preparing a pharmaceutical or a pharmaceutical product can include a fermentation process, recombinant DNA, isolation and recovery from natural resources, chemical synthesis, biosynthesis, polymerase chain reaction, or combinations thereof.

In some exemplary embodiments, the disclosure provides methods for characterizing a protein in a sample. The sample can be obtained from any step of a bioprocess, such as, culture cell culture fluid (CCF), harvested cell culture fluid (HCCF), process performance qualification (PPQ), any step in the downstream processing, drug substance (DS), or a drug product (DP) comprising the final formulated product. The sample can be selected from any step of a downstream process of clarification, chromatographic purification, viral inactivation, or filtration. The sample can be selected from a manufactured drug product in any phase of its lifecycle, including, for example, the clinic, shipping, storage, or handling of the drug product.

There can be at least two types of proteins in the sample. In some exemplary embodiments, the sample matrix can further comprise a protein of interest. As used herein, the term "protein" or "protein of interest" can include any amino acid polymer having covalently linked amide bonds. Proteins can comprise one or more amino acid polymer chains, generally known in the art as "polypeptides."

As used herein, the term "protein" can include any amino acid polymer having covalently linked amide bonds. Proteins comprise one or more amino acid polymer chains, generally known in the art as "polypeptides." "Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. "Synthetic peptides or polypeptides" refers to a non-naturally occurring peptide or polypeptide. Synthetic peptides or polypeptides can be synthesized, for example, using an automated polypeptide synthesizer. Various solid-phase peptide synthesis methods are known to those of skill in the art. A protein may comprise one or multiple polypeptides to form a single functioning biomolecule. A protein can include antibody fragments, nanobodies, recombinant antibody chimeras, cytokines, chemokines, peptide hormones, and the like. Proteins of interest can include any of bio-therapeutic proteins, recombinant proteins used in research or therapy, trap proteins and other chimeric receptor Fc-fusion proteins, chimeric proteins, antibodies, monoclonal antibodies, polyclonal antibodies, human antibodies, and bispecific antibodies. Proteins may be produced using recombinant cell-based production systems, such as the insect baculovirus system, yeast systems (e.g., Pichia sp.), mammalian systems (e.g., CHO cells and CHO derivatives like CHO-K1 cells). For a recent review discussing biotherapeutic proteins and their production, see Ghaderi et al., "Production platforms for biotherapeutic glycoproteins. Occurrence, impact, and challenges of non-human sialylation" (Darius Ghaderi et al., *Production platforms for biotherapeutic glycoproteins. Occurrence, impact, and challenges of non-human sialylation,* 28 Biotechnology and Genetic Engineering Reviews 147-176 (2012), the entire teachings of which are herein incorporated). Proteins can be classified on the basis of compositions and solubility and can thus include simple proteins, such as globular proteins and fibrous proteins; conjugated proteins, such as nucleoproteins, glycoproteins, mucoproteins, chromoproteins, phosphoproteins, metalloproteins, and lipoproteins; and derived proteins, such as primary derived proteins and secondary derived proteins. Non-limiting examples of a protein or a pharmaceutical protein product can include a recombinant protein, an antibody, a bispecific antibody, a multispecific antibody, an antibody fragment, a monoclonal antibody, a fusion protein, an scFv and combinations thereof.

As used herein, the term "recombinant protein" refers to a protein produced as the result of the transcription and translation of a gene carried on a recombinant expression vector that has been introduced into a suitable host cell. A recombinant protein can be an antibody, for example, a chimeric, humanized, or fully human antibody. A recombinant protein can be an antibody of an isotype selected from group consisting of: IgG (e.g., IgG1, IgG2, IgG3, IgG4), IgM, IgA1, IgA2, IgD, or IgE. An antibody molecule may be a full-length antibody (e.g., an IgG1 or IgG4 immunoglobulin), or the antibody can be a fragment (e.g., an Fc fragment or a Fab fragment).

The term "antibody," as used herein, includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or VH) and a heavy chain constant region. The heavy chain constant region comprises three domains, CH1, CH2 and CH3. Each light chain comprises a light chain variable region (abbreviated herein as LCVR or VL) and a light chain constant region. The light chain constant region comprises one domain (CL1). The VH and VL regions can be further subdivided into regions of hypervariability, termed complementarity determining regions (CDRs), interspersed with regions that are more conserved, termed framework regions (FRs). Each VH and VL is composed of three complementarity determining regions and four framework regions, arranged from amino-terminus to carboxy-terminus in the following order: FR1, CDR1, FR2, CDR2, FR3, CDR3, and FR4. The framework regions of the anti-big-ET-1 antibody (or antigen-binding portion thereof) may be identical to the human germline sequences or may be naturally or artificially modified. An amino acid consensus sequence may be defined based on a side-by-side analysis of two or more complementarity determining regions. The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, for example, from full antibody molecules using any suitable standard techniques such as proteolytic digestion or recombinant genetic engineering techniques involving the manipulation and expression of DNA encoding antibody variable and optionally constant domains. Such DNA is known and/or is readily available from, for example, commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

As used herein, an "antibody fragment" includes a portion of an intact antibody, such as, for example, the antigen-binding or variable region of an antibody. Examples of antibody fragments include, but are not limited to, a Fab fragment, a Fab' fragment, an F(ab')2 fragment, an scFv fragment, an Fv fragment, a dsFv diabody, a dAb fragment, an Fd' fragment, an Fd fragment, and an isolated complementarity determining region, as well as triabodies, tetrabodies, linear antibodies, single-chain antibody molecules, and multi specific antibodies formed from antibody fragments. Fv fragments are the combination of the variable regions of the immunoglobulin heavy and light chains, and ScFv proteins are recombinant single chain polypeptide molecules in which immunoglobulin light and heavy chain variable regions are connected by a peptide linker. An antibody fragment can comprise a sufficient amino acid sequence of the parent antibody of which it is a fragment that it binds to the same antigen as does the parent antibody; an antibody fragment binds to the antigen with a comparable affinity to that of the parent antibody and/or competes with the parent antibody for binding to the antigen. An antibody fragment may be produced by any means. For example, an antibody fragment may be enzymatically or chemically produced by fragmentation of an intact antibody and/or it may be recombinantly produced from a gene encoding the partial antibody sequence. Alternatively, or additionally, an antibody fragment may be wholly or partially synthetically produced. An antibody fragment may optionally comprise a single-chain antibody fragment. Alternatively, or additionally, an antibody fragment may comprise multiple chains that are linked together, for example, by disulfide linkages. An antibody fragment may optionally comprise a multi-molecular complex. A functional antibody fragment typically comprises at least about 50 amino acids and more typically comprises at least about 200 amino acids.

The term "bispecific antibody" includes an antibody capable of selectively binding two or more epitopes. Bispecific antibodies generally comprise two different heavy chains, with each heavy chain specifically binding a different epitope-either on two different molecules (e.g., antigens) or on the same molecule (e.g., on the same antigen). If a bispecific antibody is capable of selectively binding two different epitopes (a first epitope and a second epitope), the affinity of the first heavy chain for the first epitope will generally be at least one to two or three or four orders of magnitude lower than the affinity of the first heavy chain for the second epitope, and vice versa. The epitopes recognized by the bispecific antibody can be on the same or a different target (e.g., on the same or a different protein). Bispecific antibodies can be made, for example, by combining heavy chains that recognize different epitopes of the same antigen. For example, nucleic acid sequences encoding heavy chain variable sequences that recognize different epitopes of the same antigen can be fused to nucleic acid sequences encoding different heavy chain constant regions and such sequences can be expressed in a cell that expresses an immunoglobulin light chain.

A typical bispecific antibody has two heavy chains, each having three heavy chain complementarity determining regions, followed by a CH1 domain, a hinge, a CH2 domain, and a CH3 domain, and an immunoglobulin light chain that either does not confer antigen-binding specificity but that can associate with each heavy chain, or that can associate with each heavy chain and that can bind one or more of the epitopes bound by the heavy chain antigen-binding regions, or that can associate with each heavy chain and enable binding of one or both of the heavy chains to one or both epitopes. BsAbs can be divided into two major classes, those bearing an Fc region (IgG-like) and those lacking an Fc region, the latter normally being smaller than the IgG and IgG-like bispecific molecules comprising an Fc. The IgG-like bispecific antibodies (bsAbs) can have different formats such as, but not limited to, triomab, knobs-into-holes IgG (KiH IgG), crossMab, orth-Fab IgG, Dual-variable domains Ig (DVD-Ig), two-in-one or dual action Fab (DAF), IgG-single-chain Fv (IgG-scFv), or KA-bodies. The non-IgG-like different formats include tandem scFvs, diabody format, single-chain diabody, tandem diabodies (TandAbs), Dual-affinity retargeting molecule (DART), DART-Fc, nanobodies, or antibodies produced by the dock-and-lock (DNL) method (Gaowei Fan, Zujian Wang and Mingju Hao, Bispecific Antibodies and Their Applications, 8 Journal of Hematology & Oncology 130; Dafne Müller and Roland E. Kontermann, Bispecific Antibodies, Handbook of Therapeutic Antibodies 265-310 (2014), the entire teachings of which are herein incorporated).

As used herein, "multispecific antibody" refers to an antibody with binding specificities for at least two different antigens. While such molecules normally will only bind two antigens (e.g., bispecific antibodies/bsAbs), antibodies with additional specificities such as trispecific antibodies and KiH trispecific antibodies can also be addressed by the system and method disclosed herein.

The term "monoclonal antibody" as used herein, is not limited to antibodies produced through hybridoma technology. A monoclonal antibody can be derived from a single clone, including any eukaryotic, prokaryotic, or phage clone, by any means available or known in the art. Monoclonal antibodies useful with the present disclosure can be prepared using a wide variety of techniques known in the art, including the use of hybridoma, recombinant, and phage display technologies, or a combination thereof.

A protein can be produced from mammalian cells. The mammalian cells can be of human origin or non-human origin, and can include primary epithelial cells (e.g., keratinocytes, cervical epithelial cells, bronchial epithelial cells, tracheal epithelial cells, kidney epithelial cells and retinal epithelial cells), established cell lines and their strains (e.g., 293 embryonic kidney cells, BHK cells, HeLa cervical epithelial cells and PER-C6 retinal cells, MDBK (NBL-1) cells, 911 cells, CRFK cells, MDCK cells, CHO cells, BeWo cells, Chang cells, Detroit 562 cells, HeLa 229 cells, HeLa S3 cells, Hep-2 cells, KB cells, LSI80 cells, LS174T cells, NCI-H-548 cells, RPMI2650 cells, SW-13 cells, T24 cells, WI-28 VA13, 2RA cells, WISH cells, BS-C-I cells, LLC-MK2 cells, Clone M-3 cells, 1-10 cells, RAG cells, TCMK-1 cells, Y-1 cells, LLC-PKi cells, PK (15) cells, GHi cells, GH3 cells, L2 cells, LLC-RC 256 cells, MHiCi cells, XC cells, MDOK cells, VSW cells, and TH-I, B1 cells, BSC-1 cells, RAf cells, RK-cells, PK-15 cells or derivatives thereof), fibroblast cells from any tissue or organ (including but not limited to heart, liver, kidney, colon, intestines, esophagus, stomach, neural tissue (brain, spinal cord), lung, vascular tissue (artery, vein, capillary), lymphoid tissue (lymph gland, adenoid, tonsil, bone marrow, and blood), spleen, and fibroblast and fibroblast-like cell lines (e.g., CHO cells, TRG-2 cells, IMR-33 cells, Don cells, GHK-21 cells, citrullinemia cells, Dempsey cells, Detroit 551 cells, Detroit 510 cells, Detroit 525 cells, Detroit 529 cells, Detroit 532 cells, Detroit 539 cells, Detroit 548 cells, Detroit 573 cells, HEL 299 cells, IMR-90 cells, MRC-5 cells, WI-38 cells, WI-26 cells, Midi cells, CHO cells, CV-1 cells, COS-1 cells, COS-3 cells, COS-7 cells, Vero cells, DBS-FrhL-2 cells, BALB/3T3 cells, F9 cells, SV-T2 cells, M-MSV-BALB/3T3 cells, K-BALB cells, BLO-11 cells, NOR-10 cells, C3H/IOTI/2 cells, HSDMiC3 cells, KLN205 cells, McCoy cells, Mouse L cells, Strain 2071 (Mouse L) cells, L-M strain (Mouse L) cells, L-MTK' (Mouse L) cells, NCTC clones 2472 and 2555, SCC-PSA1 cells, Swiss/3T3 cells, Indian muntjac cells, SIRC cells, Cn cells, and Jensen cells, Sp2/0, NS0, NS1 cells or derivatives thereof).

A composition can be used for the treatment, prevention, and/or amelioration of a disease or disorder. Exemplary, non-limiting diseases and disorders that can be treated and/or prevented by the administration of the pharmaceutical formulations of the present invention include, infections; respiratory diseases; pain resulting from any condition associated with neurogenic, neuropathic or nociceptic pain; genetic disorder; congenital disorder; cancer; herpetiformis; chronic idiopathic urticarial; scleroderma, hypertrophic scarring; Whipple's Disease; benign prostate hyperplasia; lung disorders, such as mild, moderate or severe asthma, allergic reactions; Kawasaki disease, sickle cell disease; Churg-Strauss syndrome; Grave's disease; pre-eclampsia; Sjogren's syndrome; autoimmune lymphoproliferative syndrome; autoimmune hemolytic anemia; Barrett's esophagus;

autoimmune uveitis; tuberculosis; nephrosis; arthritis, including chronic rheumatoid arthritis; inflammatory bowel diseases, including Crohn's disease and ulcerative colitis; systemic lupus erythematosus; inflammatory diseases; HIV infection; AIDS; LDL apheresis; disorders due to PCSK9-activating mutations (gain of function mutations, "GOF"), disorders due to heterozygous Familial Hypercholesterolemia (heFH); primary hypercholesterolemia; dyslipidemia; cholestatic liver diseases; nephrotic syndrome; hypothyroidism; obesity; atherosclerosis; cardiovascular diseases; neurodegenerative diseases; neonatal Onset Multisystem Inflammatory Disorder (NOM ID/CINCA); Muckle-Wells Syndrome (MWS); Familial Cold Autoinflammatory Syndrome (FCAS); familial Mediterranean fever (FMF); tumor necrosis factor receptor-associated periodic fever syndrome (TRAPS); systemic onset juvenile idiopathic arthritis (Still's Disease); diabetes mellitus type 1 and type 2; auto-immune diseases; motor neuron disease; eye diseases; sexually transmitted diseases; tuberculosis; disease or condition which is ameliorated, inhibited, or reduced by a VEGF antagonist; disease or condition which is ameliorated, inhibited, or reduced by a PD-1 inhibitor; disease or condition which is ameliorated, inhibited, or reduced by a Interleukin antibody; disease or condition which is ameliorated, inhibited, or reduced by a NGF antibody; disease or condition which is ameliorated, inhibited, or reduced by a PCSK9 antibody; disease or condition which is ameliorated, inhibited, or reduced by a ANGPTL antibody; disease or condition which is ameliorated, inhibited, or reduced by an activin antibody; disease or condition which is ameliorated, inhibited, or reduced by a GDF antibody; disease or condition which is ameliorated, inhibited, or reduced by a Fel d1 antibody; disease or condition which is ameliorated, inhibited, or reduced by a CD antibody; disease or condition which is ameliorated, inhibited, or reduced by a C5 antibody or combinations thereof.

A composition can be administered to a patient. Administration may be via any route acceptable to those skilled in the art. Non-limiting routes of administration include oral, topical, or parenteral. Administration via certain parenteral routes may involve introducing the formulations of the present invention into the body of a patient through a needle or a catheter, propelled by a sterile syringe or some other mechanical device such as a continuous infusion system. A composition may be administered using a syringe, injector, pump, or any other device recognized in the art for parenteral administration. A composition may also be administered as an aerosol for absorption in the lung or nasal cavity. The solutions may also be administered for absorption through the mucus membranes, such as in buccal administration.

A formulation can further comprise excipients including, but not limited to, buffering agents, bulking agents, tonicity modifiers, solubilizing agents, and preservatives. Other additional excipients can also be selected based on function and compatibility with the formulations may be found, for example, in Remington: The Science and Practice of Pharmacy, (2005); U.S. Pharmacopeia: National formulary; Louis Sanford Goodman et al., Goodman and Gilmans The Pharmacological Basis of Therapeutics (2001); Kenneth E. Avis, Herbert A. Lieberman and Leon Lachman, Pharmaceutical Dosage Forms: Parenteral Medications (1992); Praful Agrawala, Pharmaceutical Dosage Forms: Tablets. Volume 1, 79 Journal of Pharmaceutical Sciences 188 (1990); Herbert A. Lieberman, Martin M. Rieger and Gilbert S. Banker, Pharmaceutical Dosage Forms: Disperse Systems (1996); Myra L. Weiner and Lois A. Kotkoskie, Excipient Toxicity and Safety (2000), herein incorporated by reference in their entirety.

In some exemplary embodiments, the method for characterizing a protein can comprise enriching at least one protein in the sample by contacting the sample with a chromatography support.

As used herein, the term "chromatography" refers to a process in which a chemical mixture carried by a liquid or gas can be separated into components as a result of differential distribution of the chemical entities as they flow around or over a stationary liquid or solid phase. Non-limiting examples of chromatography include traditional reversed phase (RP), ion exchange (IEX) and normal phase chromatography (NP). Unlike RP, NP and IEX chromatography, in which hydrophobic interaction, hydrophilic interaction and ionic interaction respectively are the dominant interaction modes, mixed-mode chromatography can employ a combination of two or more of these interaction modes. Several types of liquid chromatography can be used with the mass spectrometer, such as, rapid resolution liquid chromatography (RRLC), ultra-performance liquid chromatography (UPLC), ultra-fast liquid chromatography (UFLC) and nano liquid chromatography (nLC). For further details on chromatography method and principles, see Colin et al. (COLIN F. POOLE ET AL., LIQUID CHROMATOGRAPHY FUNDAMENTALS AND INSTRUMENTATION (2017)).

A chromatography support can be a liquid chromatography support. As used herein, the term "liquid chromatography" refers to a process in which a chemical mixture carried by a liquid can be separated into components as a result of differential distribution of the chemical entities as they flow around or over a stationary liquid or solid phase. Non-limiting examples of liquid chromatography include reversed phase liquid chromatography, ion-exchange chromatography, size exclusion chromatography, affinity chromatography, mixed-mode chromatography or hydrophobic chromatography.

As used herein, "ion exchange chromatography" can include separations including any method by which two substances are separated based on the difference in their respective ionic charges, either on the molecule of interest and/or chromatographic material as a whole or locally on specific regions of the molecule of interest and/or chromatographic material, and thus can employ either cationic exchange material or anionic exchange material. Ion exchange chromatography separates molecules based on differences between the local charges of the molecules of interest and the local charges of the chromatographic material. A packed ion-exchange chromatography column or an ion-exchange membrane device can be operated in a bind-elute mode, a flow-through, or a hybrid mode. After washing the column or the membrane device with the equilibration buffer or another buffer with different pH and/or conductivity, the product recovery can be achieved by increasing the ionic strength (e.g., conductivity) of the elution buffer to compete with the solute for the charged sites of the ion exchange matrix. Changing the pH and thereby altering the charge of the solute can be another way to achieve elution of the solute. The change in conductivity or pH may be gradual (gradient elution) or stepwise (step elution). The column can be then regenerated before next use. Anionic or cationic substituents may be attached to matrices in order to form anionic or cationic supports for chromatography. Non-limiting examples of anionic exchange substituents include diethylaminoethyl (DEAE), quaternary aminoethyl (QAE) and quaternary amine (Q) groups. Cationic substituents include carboxymethyl (CM), sulfoethyl (SE), sulfopropyl (SP), phosphate (P) and sulfonate(S). Cellulose ion exchange medias or support can include DE23™, DE32™, DE52™, CM-23™, CM-32™, and CM-52™ are available from Whatman Ltd. Maidstone, Kent, U.K. SEPHADEX®-based and -locross-linked ion exchangers are also known. For example, DEAE-, QAE-, CM-, and SP-SEPHADEX® and DEAE-, Q-, CM- and S-SEPHAROSE® and SEPHAROSER Fast Flow, and Capto™ S are all available from GE Healthcare. Further, both DEAE and CM derivatized ethylene glycol-methacrylate copolymer such as TOYOPEARL™ DEAE-650S or M and TOYOPEARL™ CM-650S or M are available from Toso Haas Co., Philadelphia, Pa., or Nuvia S and UNOSphere™ S from BioRad, Hercules, Calif., Eshmuno® S from EMD Millipore, MA.

As used herein, the term "hydrophobic interaction chromatography resin" can include a solid phase which can be covalently modified with phenyl, octyl, or butyl chemicals. It can use the properties of hydrophobicity to separate molecules from one another. In this type of chromatography, hydrophobic groups such as, phenyl, octyl, hexyl or butyl can be attached to the stationary column. Molecules that pass through the column that have hydrophobic amino acid side chains on their surfaces are able to interact with and bind to the hydrophobic groups on the column. Examples of hydrophobic interaction chromatography resins or support include Phenyl sepharose FF, Capto Phenyl (GE Healthcare, Uppsala, Sweden), Phenyl 650-M (Tosoh Bioscience, Tokyo, Japan) and Sartobind Phenyl (Sartorius corporation, New York, USA).

As used herein, the term "Mixed Mode Chromatography (MMC)" or "multimodal chromatography" includes a chromatographic method in which solutes interact with stationary phase through more than one interaction mode or mechanism. MMC can be used as an alternative or complementary tool to traditional reversed phase (RP), ion exchange (IEX) and normal phase chromatography (NP). Unlike RP, NP and IEX chromatography, in which hydrophobic interaction, hydrophilic interaction and ionic interaction respectively are the dominant interaction modes, mixed-mode chromatography can employ a combination of two or more of these interaction modes. Mixed mode chromatography media can provide unique selectivity that cannot be reproduced by single mode chromatography. Mixed mode chromatography can also provide potential cost savings, longer column lifetimes and operation flexibility compared to affinity-based methods. A mixed mode chromatography media can be comprised of mixed mode ligands coupled to an organic or inorganic support, sometimes denoted a base matrix, directly or via a spacer. The support may be in the form of particles, such as essentially spherical particles, a monolith, filter, membrane, surface, capillaries, etc. In some specific exemplary embodiments, the support can be prepared from a native polymer, such as cross-linked carbohydrate material, such as agarose, agar, cellulose, dextran, chitosan, konjac, carrageenan, gellan, alginate etc. To obtain high adsorption capacities, the support can be porous, and ligands are then coupled to the external surfaces as well as to the pore surfaces. Such native polymer supports can be prepared according to standard methods, such as inverse suspension gelation (Stellan Hjertén, *The preparation of agarose spheres for chromatography of molecules and particles,* 79 Biochimica et Biophysica Acta (BBA)—Biophysics including Photosynthesis 393-398 (1964) incorporated herein by reference). Alternatively, the support can be prepared from a synthetic polymer, such as cross-linked synthetic polymers, e.g., styrene or styrene derivatives, divinylbenzene, acrylamides, acrylate esters, methacrylate esters, vinyl esters, vinyl amides etc. Such synthetic polymers can be produced according to standard methods, see e.g., Eduardo Vivaldo-Lima et al., *An Updated Review on Suspension Polymerization,* 36 Industrial & Engineering Chemistry Research 939-965 (1997). Porous native or synthetic polymer supports are also available from commercial sources, such as Amersham Biosciences, Uppsala, Sweden.

In some exemplary embodiments, the method for characterizing a protein can comprise enriching at least one protein in the sample by contacting the sample with an affinity chromatography support.

As used herein, "affinity chromatography" can include separations including any method by which two substances are separated based on their affinity to a chromatographic material. Non-limiting examples of affinity chromatography support include, but are not limited to Protein A resin, Protein G resin, affinity supports comprising the antigen against which the binding molecule was raised, and affinity supports comprising an Fc binding protein. The affinity chromatography resin can be formed by immobilizing Protein A, Protein G, antigen against which the binding molecule was raised, or Fc binding protein on a resin, such as, agarose or sepharose. There are several commercial sources for Protein A resin. Non-limiting examples of Protein A resin include MabSelect SuRe™, MabSelect SuRe LX, MabSelect, MabSelect Xtra, rProtein A Sepharose from GE Healthcare, and ProSep HC, ProSep Ultra, and ProSep Ultra Plus from EMD Millipore.

The affinity chromatographic material can be equilibrated with a suitable buffer prior to sample matrix loading. Following this equilibration, the sample matrix can be loaded onto the column. Following the loading of the affinity chromatographic material, the affinity chromatographic material can be washed one or multiple times using an appropriate wash buffer. A flow-through from the wash can be collected. The flow-through from the wash can be further processed. Optionally other washes, including washes employing different buffers, can be employed prior to eluting the column. A flow-through from the washes can be collected and further processed. The affinity chromatographic material can also be eluted using an appropriate elution buffer. The eluate can be monitored using techniques well known to those skilled in the art. For example, the absorbance at OD280 can be followed. The elution fraction(s) of interest can then be prepared for further processing.

A kosmotropic salt solution can be supplemented into the sample matrix comprising the protein of interest prior to contacting with an affinity chromatography resin. The kosmotropic salt solution comprises at least one kosmotropic salt. Examples of suitable kosmotropic salts include, but are not limited to ammonium sulfate, sodium sulfate, sodium citrate, potassium sulfate, potassium phosphate, sodium phosphate and a combination thereof. The kosmotropic salt can be present in the kosmotropic salt solution at a concentration of from about 0.3 M to about 1.1 M.

In some exemplary embodiments, the enrichment step can further comprise treating a sample obtained from the chromatography support.

In some exemplary embodiments, a sample obtained from the chromatography support can be treated with a treatment. The treatment can include adding a hydrolyzing agent to the sample to produce peptides. As used herein, the term "hydrolyzing agent" refers to any one or combination of a large number of different agents that can perform digestion of a protein. Non-limiting examples of hydrolyzing agents that can carry out enzymatic digestion include trypsin, endoproteinase Arg-C, endoproteinase Asp-N, endoproteinase Glu-C, outer membrane protease T (OmpT), immunoglobulin-degrading enzyme of *Streptococcus pyogenes* (IdeS), chymotrypsin, pepsin, thermolysin, papain, pronase, and protease from *Aspergillus saitoi*. Non-limiting examples of hydrolyzing agents that can carry out non-enzymatic digestion include the use of high temperature, microwave, ultrasound, high pressure, infrared, solvents (non-limiting examples are ethanol and acetonitrile), immobilized enzyme digestion (IMER), magnetic particle immobilized enzymes, and on-chip immobilized enzymes. For a recent review discussing the available techniques for protein digestion see Switazar et al., "Protein Digestion: An Overview of the Available Techniques and Recent Developments" (Linda Switzar, Martin Giera & Wilfried M. A. Niessen, *Protein Digestion: An Overview of the Available Techniques and Recent Developments,* 12 Journal of Proteome Research 1067-1077 (2013)). One or a combination of hydrolyzing agents can cleave peptide bonds in a protein or polypeptide, in a sequence-specific manner, generating a predictable collection of shorter peptides.

The term ratio of hydrolyzing agent to the protein and the time required for digestion can be appropriately selected to obtain a digestion of the protein. When the enzyme to substrate (E/S) ratio is unsuitably high, it can cause a non-specific cleavage (potentially breaking all proteins/peptides into individual amino acids) thereby limiting the ability to identify proteins as well as reducing sequence coverage. On the other hand, a low E/S ratio would need long digestion and thus long sample preparation time. The enzyme to substrate ratio can range from about 1:0.5 to about 1:500. In Exemplary embodiments, the enzyme to substrate ratio can be 1:50, 1:100, or 1:200.

As used herein, the term "digestion" refers to hydrolysis of one or more peptide bonds of a protein. There are several approaches to carrying out digestion of a protein in a sample using an appropriate hydrolyzing agent, for example, enzymatic digestion or non-enzymatic digestion.

One of the widely accepted methods for digestion of proteins in a sample involves the use of proteases. Many proteases are available and each of them have their own characteristics in terms of specificity, efficiency, and optimum digestion conditions. Proteases refer to both endopeptidases and exopeptidases, as classified based on the ability of the protease to cleave at non-terminal or terminal amino acids within a peptide. Alternatively, proteases also refer to the six distinct classes-aspartic, glutamic, and metalloproteases, cysteine, serine, and threonine proteases, as classified on the mechanism of catalysis. The terms "protease" and "peptidase" are used interchangeably to refer to enzymes which hydrolyze peptide bonds.

Apart from contacting a protein to a hydrolyzing agent, the method can optionally include steps for reducing the protein, alkylating the protein, buffering the protein, and/or desalting the sample. These steps can be accomplished in any suitable manner as desired.

The treatment can include adding a protein reducing agent to the sample. As used herein, the term "protein reducing agent" refers to the agent used for reduction of disulfide bridges in a protein. Non-limiting examples of the protein reducing agents used to reduce the protein are dithiothreitol (DTT), β-mercaptoethanol, Ellman's reagent, hydroxylamine hydrochloride, sodium cyanoborohydride, tris(2-carboxyethyl) phosphine hydrochloride (TCEP-HCl), or combinations thereof.

The treatment can include adding a protein alkylating agent to the sample. As used herein, the term "protein alkylating agent" refers to the agent used for alkylate certain free amino acid residues in a protein. Non-limiting examples of the protein alkylating agents are iodoacetamide (IOA), chloroacetamide (CAA), acrylamide (AA), N-ethylmaleimide (NEM), methyl methanethiosulfonate (MMTS), and 4-vinylpyridine or combinations thereof.

The treatment can include adding one or more form the group consisting of alkylating agent, reducing agent, hydrolyzing agent or combinations thereof. The additions of these agents to the sample can vary. The addition can be carried by adding the sample to the agents or by adding the agents to the samples.

The method for characterizing a protein can comprise enriching at least one protein in a sample by contacting the sample with a chromatography support and performing a fractionation step. As used herein, the term "fractionation" can include a process of separating various peptides obtained from digesting the proteins present in a sample. The process can involve separating the peptides using an appropriate peptide fractionation technique(s) which can fractionate the peptides based their various general properties such as the peptides' pI, hydrophobicity, metal binding ability, content of exposed thiol groups, size, charge, shape, solubility, stability and sedimentation velocity, ability to bind with various ionic groups, and affinity for substrates as a basis for isolating peptide(s) from complex biological sample matrixes. Peptides can also be separated based on their cellular location, thereby allowing to extract cytoplasmic, nuclear and membrane proteins.

The fractionation can be a size-based fractionation. The size-based fractionation can be carried out by using gel electrophoresis. Details on gel electrophoresis can be found in Zaifang Zhu, Joann Lu & Shaorong Liu, *Protein separation by capillary gel electrophoresis: A review,* 709 Analytica Chimica Acta 21-31 (2012), which is incorporated herein by reference. Further principles and basics can be found in Sameh Magdeldin, Gel electrophoresis: principles and basics (2012), which is incorporated herein by reference.

The size-based fractionation can be carried out by using dialysis. The dialysis can be performed using a molecular cut-off membrane filter or a series of membrane filters. The dialysis can also be performed using dialysis cassettes. Example of one such dialysis methods can include using Slide-A-Lyzer™ Dialysis Cassettes. The cassette design helps maximize surface area to sample volume ratio and enables excellent sample recoveries.

The size-based fractionation can be carried out by using capillary electrophoresis. Recent trends and advances on capillary electrophoresis can be found in Robert Voeten et al., *Capillary Electrophoresis: Trends and Recent Advances,* 90 Analytical Chemistry 1464-1481 (2018) and María Ramos-Payán et al., *Recent trends in capillary electrophoresis for complex samples analysis: A review,* 39 Electrophoresis 111-125 (2017), which are incorporated herein by reference. Further principles and basics can be found in Harry Whatley, *Basic Principles and Modes of Capillary Electrophoresis*, Clinical and Forensic Applications of Capillary Electrophoresis 21-58, which is incorporated herein by reference.

The size-based fractionation can be carried out using size exclusion chromatography. The phrase "size exclusion chromatography" or "SEC" or "gel filtration" includes a liquid column chromatographic technique that can sort molecules according to their size in solution. As used herein, the terms "SEC chromatography resin" or "SEC chromatography media" are used interchangeably herein and can include any kind of solid phase used in SEC which separates the impurity from the desired product (e.g., a homodimer contaminant for a bispecific antibody product). The volume of the resin, the length and diameter of the column to be used, as well as the dynamic capacity and flow-rate can depend on several parameters such as the volume of fluid to be treated, concentration of protein in the fluid to be subjected to the process of the invention, etc. Determination of these parameters for each step is well within the average skills of the person skilled in the art. A brief practical review on size exclusion chromatography can be found in Richard R. Burgess, *A brief practical review of size exclusion chromatography: Rules of thumb, limitations, and troubleshooting,* 150 Protein Expression and Purification 81-85 (2018) and Gloria Brusotti et al., *Advances on Size Exclusion Chromatography and Applications on the Analysis of Protein Biopharmaceuticals and Protein Aggregates: A Mini Review,* 81 Chromatographia 3-23 (2017), which are each incorporated herein by reference. Further principles and basics of SEC can be found in Paula Hong, Stephan Koza & Edouard S. P. Bouvier, *A Review Size-Exclusion Chromatography For The Analysis Of Protein Biotherapeutics And Their Aggregates,* 35 Journal of Liquid Chromatography & Related Technologies 2923-2950 (2012), which is incorporated herein by reference. Newer methods for size exclusion chromatography can also be used for the methods, as illustrated in Singh et al., *New Automated Systems for Size-fractionation of Protein Samples,* 24 Journal of Biomolecular Technologies S60-S61 (2013), which is incorporated herein by reference.

The size-based fractionation can be carried out using field flow fractionation. The field flow fractionation (FFF) is a class of 'soft impact' elution techniques employed mainly to separate heterogeneous mixtures of supramolecules, proteins and bioparticles (<100 μm dia.) within laminar microfluidic flows. An overview of the FFF is provided by in the article by Messaud et al. (Fathi A. Messaud et al., *An overview on field-flow fractionation techniques and their applications in the separation and characterization of polymers,* 34 Progress in Polymer Science 351-368 (2009)), which is incorporated herein by reference. Further techniques for FFF can be found in T. Kowalkowski et al., *Field-Flow Fractionation: Theory, Techniques, Applications and the Challenges,* 36 Critical Reviews in Analytical Chemistry 129-135 (2006) and Barbara Roda et al., *Field-flow fractionation in bioanalysis: A review of recent trends,* 635 Analytica Chimica Acta 132-143 (2009), which are each incorporated herein by reference.

The fractionation can be a hydrophobicity-based fractionation. In one aspect, the size-based fractionation can be carried out using reversed phase chromatography. Reversed phase chromatography is the most widely used chromatographic mode allowing separation of proteins on the basis of their hydrophobicity. The separation is based on the analytes partition coefficient between the polar mobile phase and the hydrophobic (nonpolar) stationary phase. In the case of peptides, more polar peptides elute first while less polar peptides interact more strongly with the hydrophobic groups that form a 'liquid-like' layer around the solid silica support. RPLC has been extensively applied in peptide separation for its ease of use with gradient elution, compatibility with aqueous samples and versatility of the retention mechanism, allowing changes in the separation brought by changes in the pH, organic modifier or additives. The size-based fractionation can be carried out using a pH gradient chromatography.

The reversed phase chromatography can comprise a low pH reversed phase liquid chromatography separation using the nano LC. The reversed phase chromatography can comprise a high pH reversed phase liquid chromatography separation. The reversed phase chromatography can comprise a high pH reversed phase liquid chromatography separation orthogonal to a low pH reversed phase liquid chromatography. An overview of one such two-Dimensional Separation Using High-pH and Low-pH Reversed Phase Liquid Chromatography for Top-down Proteomics can be found in Zhe Wang et al., *Two-dimensional separation using high-pH and low-pH reversed phase liquid chromatography for top-down proteomics,* 427 International Journal of Mass Spectrometry 43-51 (2018).

The fractionation can be a charge-based fractionation. The charge-based fractionation can be carried out using an ion-exchange chromatography. The ion-exchange chromatography can be a cation-exchange chromatography. The ion-exchange chromatography can be an anion-exchange chromatography.

The fractionation can be a pI-based fractionation. The charge-based fractionation can be carried out using an ion-exchange chromatography. The ion-exchange chromatography can be a cation-exchange chromatography. The ion-exchange chromatography can be an anion-exchange chromatography. The charge-based fractionation can be carried by isoelectric focusing. Isoelectric focusing (IEF) can provide separation of proteins, wherein proteins can travel according to their charge under the influence of an electric field, in the presence of a pH gradient, until the net charge of the molecule is zero (e.g., isoelectric point, pI). The separation can be deemed according to the composition of amino acids and exposed charged residues, which behave as weak acids and bases. The migration of the proteins will follow basic principles of electrophoresis; however, the mobility will change in the presence of the pH gradient by slowing down migration at values close to the pI value. An overview of the IEF is provided by in the article by Pergande and Cologna Melissa Pergande & Stephanie Cologna, *Isoelectric Point Separations of Peptides and Proteins,* 5 Proteomes 4 (2017), which is incorporated herein by reference. Further techniques for IEF can be found in Findley Cornell, *Isoelectric Focusing, Blotting and Probing Methods for Detection and Identification of Monoclonal Proteins,* 30 The Clinical Biochemist Reviews 123-130 (2009); Tomasz Bączek, *Fractionation of peptides in proteomics with the use of pI-based approach and ZipTip pipette tips,* 34 Journal of Pharmaceutical and Biomedical Analysis 851-860 (2004); C. F. Ivory, A Brief Review of Alternative Electrofocusing Techniques, 35 Separation Science and Technology 1777-1793 (2000); G. B. Smejkal, *Solution phase isoelectric fractionation in the multi-compartment electrolyser: A divide and conquer strategy for the analysis of complex proteomes,* 4 Briefings in Functional Genomics and Proteomics 76-81 (2005), and David Garfin, *Gel Electrophoresis of Proteins*, in Essential Cell Biology, Volume 1, a practical approach 197-268 (2003), which are each incorporated herein by reference.

Further improvements in the pI-based fractionation can be used for the fractionation step, such as, methods delineated in Subhashini Selvaraju & Ziad El Rassi, *Liquid-phase-based separation systems for depletion, prefractionation and enrichment of proteins in biological fluids and matrices for in-depth proteomics analysis-An update covering the period* 2008-2011, 33 Electrophoresis 74-88 (2011).

The method for identifying an N-glycan profile of a protein in a sample can comprise analyzing and/or characterizing the protein using a mass spectrometer.

The analyzing and/or characterizing can include identifying the peptides obtained from the fractionation step.

Peptide identification can be further performed by comparing the mass spectra derived from the polypeptide fragmentation with the theoretical mass spectra generated from in silico digestion of a protein. Protein inference is then accomplished by assigning peptide sequences to proteins.

As used herein, the term "mass spectrometer" includes a device capable of identifying specific molecular species and measuring their accurate masses. The term is meant to include any molecular detector into which a polypeptide or peptide may be eluted for detection and/or characterization. A mass spectrometer can include three major parts: the ion source, the mass analyzer, and the detector. The role of the ion source is to create gas phase ions. Analyte atoms, molecules, or clusters can be transferred into gas phase and ionized either concurrently (as in electrospray ionization) or through separate processes. The choice of ion source depends heavily on the application. The mass spectrometer can be a tandem mass spectrometer.

The mass spectrometer can be coupled to a liquid chromatography-multiple reaction monitoring system. More generally, a mass spectrometer may be capable of analysis by selected reaction monitoring (SRM), including consecutive reaction monitoring (CRM) and parallel reaction monitoring (PRM).

As used herein, "multiple reaction monitoring" or "MRM" refers to a mass spectrometry-based technique that can precisely quantify small molecules, peptides, and proteins within complex matrices with high sensitivity, specificity and a wide dynamic range (Paola Picotti & Ruedi Aebersold, Selected reaction monitoring-based proteomics: workflows, potential, pitfalls and future directions, 9 NATURE METHODS 555-566 (2012)). MRM can be typically performed with triple quadrupole mass spectrometers wherein a precursor ion corresponding to the selected small molecules/peptides is selected in the first quadrupole and a fragment ion of the precursor ion was selected for monitoring in the third quadrupole (Yong Seok Choi et al., Targeted human cerebrospinal fluid proteomics for the validation of multiple Alzheimers disease biomarker candidates, 930 JOURNAL OF CHROMATOGRAPHY B 129-135 (2013)).

SRM/MRM/Selected-ion monitoring (SIM) is a method used in tandem mass spectrometry in which an ion of a particular mass is selected in the first stage of a tandem mass spectrometer and an ion product of a fragmentation reaction of the precursor ion is selected in the second mass spectrometer stage for detection. Examples of triple quadrupole mass spectrometers (TQMS) that can perform MRM/SRM/SIM include but are not limited to QTRAP® 6500 System (Sciex), QTRAP® 5500 System (Sciex), Triple QTriple Quad 6500 System (Sciex), Agilent 6400 Series Triple Quadrupole LC/MS systems, and Thermo Scientific™ TSQ™ Triple Quadrupole system.

In addition to MRM, the choice of peptides can also be quantified through Parallel-Reaction Monitoring (PRM). Parallel reaction monitoring (PRM) is the application of SRM with parallel detection of all transitions in a single analysis using a high-resolution mass spectrometer. PRM provides high selectivity, high sensitivity and high-throughput to quantify selected peptide (Q1), hence quantify proteins. Multiple peptides can be specifically selected for each protein. PRM methodology can use the quadrupole of a mass spectrometer to isolate a target precursor ion, fragment the targeted precursor ion in the collision cell, and then detect the resulting product ions in the Orbitrap mass analyzer. PRM can use a quadrupole time-of-flight (QTOF) or hybrid quadrupole-orbitrap (QOrbitrap) mass spectrometer to carry out the identification of peptides and/or proteins. Examples of QTOF include but are not limited to TripleTOF® 6600 System (Sciex), TripleTOF® 5600 System (Sciex), X500R QTOF System (Sciex), 6500 Series Accurate-Mass Quadrupole Time-of-Flight (Q-TOF) (Agilent) and Xevo G2-XS QT of Quadrupole Time-of-Flight Mass Spectrometry (Waters). Examples of QObitrap include but are not limited to Q Exactive™ Hybrid Quadrupole-Orbitrap Mass Spectrometer (Thermo Scientific) and Orbitrap Fusion™ Tribrid™ (Thermo Scientific).

The mass spectrometer in the method or system of the present application can be an electrospray ionization mass spectrometer, nano-electrospray ionization mass spectrometer, or a triple quadrupole mass spectrometer, wherein the mass spectrometer can be coupled to a liquid chromatography system, wherein the mass spectrometer is capable of performing LC-MS (liquid chromatography-mass spectrometry) or LC-MRM-MS (liquid chromatography-multiple reaction monitoring-mass spectrometry) analyses.

As used herein, the term "tandem mass spectrometry" includes a technique where structural information on sample molecules is obtained by using multiple stages of mass selection and mass separation. A prerequisite is that the sample molecules can be transferred into the gas phase and ionized intact and that they can be induced to fall apart in some predictable and controllable fashion after the first mass selection step. Multistage MS/MS, or $MS^n$, can be performed by first selecting and isolating a precursor ion ($MS^2$), fragmenting it, isolating a primary fragment ion ($MS^3$), fragmenting it, isolating a secondary fragment ($MS^4$), and so on as long as one can obtain meaningful information or the fragment ion signal is detectable. Tandem MS has been successfully performed with a wide variety of analyzer combinations. What analyzers to combine for a certain application can be determined by many different factors, such as sensitivity, selectivity, and speed, but also size, cost, and availability. The two major categories of tandem MS methods are tandem-in-space and tandem-in-time, but there are also hybrids where tandem-in-time analyzers are coupled in space or with tandem-in-space analyzers. A tandem-in-space mass spectrometer comprises an ion source, a precursor ion activation device, and at least two non-trapping mass analyzers. Specific m/z separation functions can be designed so that in one section of the instrument ions are selected, dissociated in an intermediate region, and the product ions are then transmitted to another analyzer for m/z separation and data acquisition. In tandem-in-time, mass spectrometer ions produced in the ion source can be trapped, isolated, fragmented, and m/z separated in the same physical device.

The peptides identified by the mass spectrometer can be used as surrogate representatives of the intact protein and their post translational modifications. They can be used for protein characterization by correlating experimental and theoretical MS/MS data, the latter generated from possible peptides in a protein sequence database. The characterization includes, but is not limited to, sequencing amino acids of the protein fragments, determining protein sequencing, determining protein de novo sequencing, locating post-translational modifications, or identifying post translational modifications, or comparability analysis, or combinations thereof.

As used herein, the term "database" refers to bioinformatic tools which provide the possibility of searching the uninterpreted MS-MS spectra against all possible sequences in the database(s). Non-limiting examples of such tools are Mascot (www.matrixscience.com), Spectrum Mill (www.chem.agilent.com), PLGS (www.waters.com), PEAKS (www.bioinformaticssolutions.com), Proteinpilot (download.appliedbiosystems.com//proteinpilot), Phenyx (www.phenyx-ms.com), Sorcerer (www.sagenresearch.com), OMSSA (www.pubchem.ncbi.nlm.nih.gov/omssa/), X!Tandem (www.thegpm.org/TANDEM/), Protein Prospector (www. prospector.ucsf.edu/prospector/mshome.htm), Byonic (www.proteinmetrics.com/products/byonic), Andromeda (www.ncbi.nlm.nih.gov/pubmed/21254760) or Sequest (fields.scripps.edu/sequest).

The mass spectrometer can be coupled to a liquid chromatography system. The mass spectrometer can be coupled to a nano liquid chromatography system. The mobile phase used to elute the protein in liquid chromatography can be a mobile phase that can be compatible with a mass spectrometer. The mobile phase can be ammonium acetate, ammonium bicarbonate, or ammonium formate, acetonitrile, water, formic acid, a volatile acid, or combinations thereof.

The method for analyzing a protein can comprise further characterizing at least one of the proteins using High-Field Asymmetric Waveform Ion Mobility Spectrometry. As used herein, "High field asymmetric waveform ion mobility spectrometry" or "FAIMS" or "differential mobility spectrometry" or "DMS" can include an atmospheric pressure ion mobility technique that separates gas-phase ions by their behavior in strong and weak electric fields. A "FAIMS device" can be easily interfaced with electrospray ionization and has been implemented as an additional separation mode between liquid chromatography (LC) and mass spectrometry (MS) in proteomic studies. FAIMS separation can be orthogonal to both LC and MS and can be used as a means of on-line fractionation to improve detection of peptides in complex samples. FAIMS can improve dynamic range and concomitantly the detection limits of ions by filtering out chemical noise. FAIMS can also be used to remove interfering ion species and to select peptide charge states optimal for identification by tandem MS. A review on use of FAIMS for mass spectrometry-based proteomics can be found in the article published by Swearingen and Moritz (Kristian E Swearingen & Robert L Moritz, High-field asymmetric waveform ion mobility spectrometry for mass spectrometry-based proteomics, 9 Expert Review of Proteomics 505-517 (2012)), which is incorporated herein by reference. Further details on FAIMS can also be found in several reviews: Roger Guevremont, *High-field asymmetric waveform ion mobility spectrometry: A new tool for mass spectrometry,* 1058 Journal of Chromatography A 3-19 (2004); Alexandre A. Shvartsburg et al., Field Asymmetric Waveform Ion Mobility Spectrometry Studies of Proteins: Dipole Alignment in Ion Mobility Spectrometry?, 110 The Journal of Physical Chemistry B 21966-21980 (2006); Beata M. Kolakowski & Zoltán Mester, Review of applications of high-field asymmetric waveform ion mobility spectrometry (FAIMS) and differential mobility spectrometry (DMS), 132 The Analyst 842 (2007), all of which are incorporated herein by reference. A general review of FAIMS by Kolakowski and Mester, a series of theoretical and practical explorations of FAIMS by Nazarov and co-workers (Nazarov, *Electric field dependence of the ion mobility,* 285 International Journal of Mass Spectrometry 149-156 (2009)); Bradley B. Schneider et al., *Planar differential mobility spectrometer as a pre-filter for atmospheric pressure ionization mass spectrometry,* 298 International Journal of Mass Spectrometry 45-54 (2010); Evgeny V. Krylov et al., *Selection and generation of waveforms for differential mobility spectrometry,* 81 Review of Scientific Instruments 024101 (2010); Bradley B. Schneider et al., *Control of Chemical Effects in the Separation Process of a Differential Mobility Mass Spectrometer System,* 16 European Journal of Mass Spectrometry 57-71 (2010); Stephen L. Coy et al., *Detection of radiation-exposure biomarkers by differential mobility prefiltered mass spectrometry* (*DMS-MS*), 291 International Journal of Mass Spectrometry 108-117 (2010); Bradley B. Schneider et al., *Control of Chemical Effects in the Separation Process of a Differential Mobility Mass Spectrometer System,* 16 European Journal of Mass Spectrometry 57-71 (2010) and a book by Shvartsburg (Alexandre A. Shvartsburg, Differential ion mobility spectrometry nonlinear ion transport and fundamentals of FAIMS (2009)), all of which are incorporated herein by reference.

Any of the commercial or adapted mass spectrometers and FAIMS cells/systems/devices can be utilized for the characterization of the protein. The FAIMS cells can vary in size-they can be a "full-size" cell (FS-FAIMS) with a length of 65 mm, width of 20 mm, and analytical gap of 2 mm; and a "quarter-size" cell (QS-FAIMS) with a length of 15 mm, a width of 5 mm, and an analytical gap of 0.38 mm. The FAIMS device used can be c-FAIMS by Ionalytics or p-FAIMS by Sionex. Miniaturized, chip-based FAIMS systems can also be used, such as, obtained from Owlstone Nanotech Inc.: UltraFAIMS A1 and the Lonestar Gas Analyzer. Both chips in each device are comprised of two interdigitated electrodes that create a serpentine geometry across the face of the chip, where each row is a distinct planar FAIMS channel. The FAIMS Pro™ Interface from Thermo Scientific can also be used for the method.

It is understood that the present invention is not limited to any of the aforesaid solution(s), composition(s), pharmaceutical(s), pharmaceutical product(s), protein(s), pharmaceutical protein product(s), protein(s), polypeptide(s), synthetic polypeptide(s), recombinant protein(s), antibody(ies), antigen-binding portion(s), antigen-binding fragment(s), antibody fragment(s), bispecific antibody(ies), multispecific antibody(ies), formulation(s), excipient(s) or cell(s) and solution(s), composition(s), pharmaceutical(s), pharmaceutical product(s), protein(s), pharmaceutical protein product(s), protein(s), polypeptide(s), synthetic polypeptide(s), recombinant protein(s), antibody(ies), antigen-binding portion(s), antigen-binding fragment(s), antibody fragment(s), bispecific antibody(ies), multispecific antibody(ies), formulation(s), excipient(s) or cell(s) can be selected by any suitable means.

EXAMPLES

Experimental Procedures

Reagents and Chemicals

Pooled normal complement-preserved human sera were purchased from BioIVT (Vendor 1) and Innovative Research (Vendor 2). Individual human sera were purchased from Innovative Research. Mouse serum was purchased from Rockland Immunochemicals. Recombinant IgG1 and IgG4 were produced in-house at Regeneron. Recombinant IgG2 and IgG3 (Fc domain only) were purchased from ACRO-Biosystems. Other chemicals were purchased from Sigma-Aldrich unless otherwise noted.

Generation of Standard IgG Subclass Mix

Figure 3:
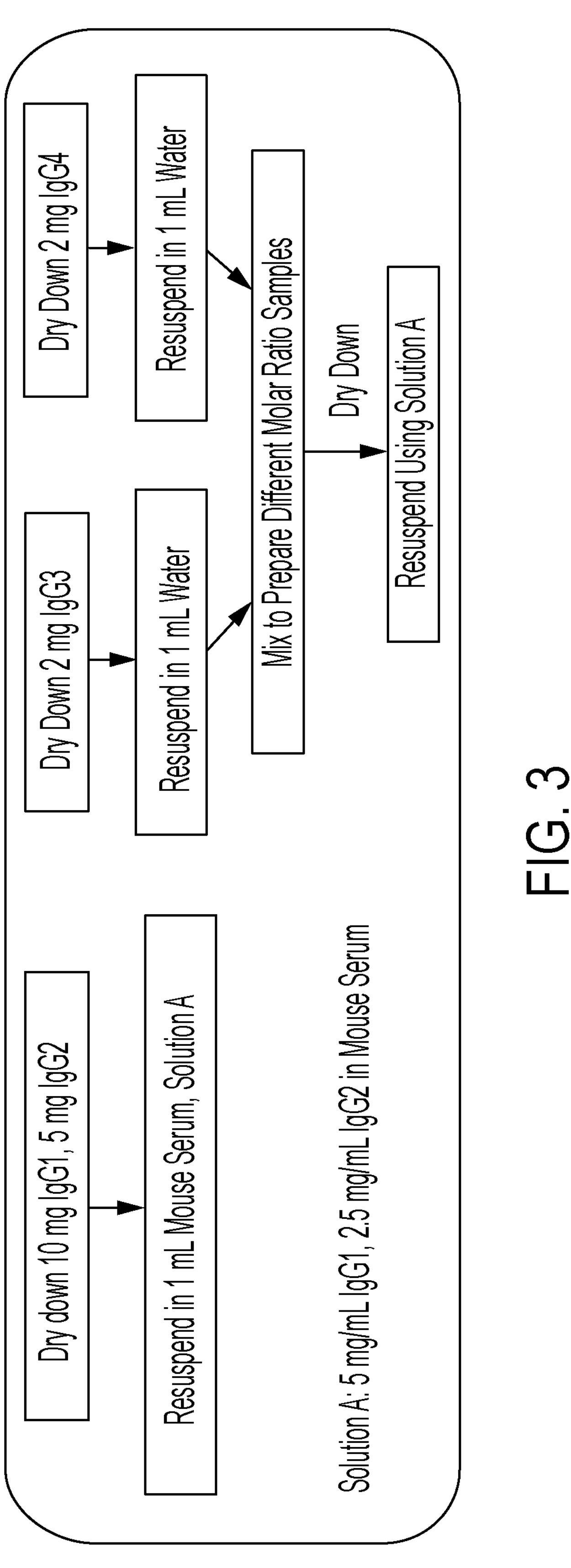
FIG. 3 illustrates the protocol for the generation of standard IgG subclass mixes, according to an exemplary embodiment.

FIG. 3 illustrates an exemplary embodiment of the following protocol for the generation of standard IgG subclass mixes. Solutions containing 10 mg of IgG1 and 1.67 mg of IgG2 Fc-domain (corresponding to 5 mg of full-length IgG2) were mixed and lyophilized. The dried IgG1/IgG2 mixture was reconstituted in 1 ml of mouse serum. The IgG3 and IgG4 solutions were mixed at the ratios indicated in Table 1 and lyophilized. Dried IgG3/IgG4 mixtures were reconstituted in the mouse serum containing IgG1 and IgG2.

Final concentrations for each sample are indicated in Table 1. A series of matrix-free IgG mixtures were prepared in parallel by mixing each protein in suggested ratio and directly diluted in water to reach the final concentrations specified Table 1. In Table 1, sample 7 (shaded column) represents general physiological concentrations of the IgGs, which are shown in Table 2.

for PRM data acquisition (Step II). Columns were flushed and re-equilibrated under 10 μl/min flow rate driven by a microflow pump. Any compounds washed from columns were discarded. The loading pump flow (5 μl/min) was introduced to an ion source for spraying to maintain the stable performance of M3 emitter (Step III). The varied flow rate, gradient and valve switch were optimized.

TABLE 1

Final Concentrations of Standard IgG Subclass Mixture in Mouse Serum

| Sample Number | | 1 | 2 | 3 | 4 | 5 | 6 | 7 | 8 | 9 | 10 | 11 | 12 | 13 |
|---|---|---|---|---|---|---|---|---|---|---|---|---|---|---|
| IgG3:IgG4 Ratios | | IgG3 Only | 100:1 | 50:1 | 10:1 | 5:1 | 2:1 | 1:1 | 1:2 | 1:5 | 1:10 | 1:50 | 1:100 | IgG4 Only |
| Final Concentration (μg/mL) | IgG1 | 5,000 | 5,000 | 5,000 | 5,000 | 5,000 | 5,000 | 5,000 | 5,000 | 5,000 | 5,000 | 5,000 | 5,0000 | 5,0000 |
| | IgG2 | 2,500 | 2,500 | 2,500 | 2,500 | 2,500 | 2,500 | 2,500 | 2,500 | 2,500 | 2,500 | 2,500 | 2,500 | 2,500 |
| | IgG3 | 1,000 | 1,000 | 1,000 | 1,000 | 1,000 | 1,000 | 1,000 | 500 | 200 | 100 | 20 | 10 | 0 |
| | IgG4 | 0 | 10 | 20 | 100 | 200 | 500 | 1,000 | 1,000 | 1,000 | 1,000 | 1,000 | 1,000 | 1,000 |

TABLE 2

SIGMA-ALDRICH ® Normal Serum, Ascites, and Cell Supernatant Typical Immunoglobin Concentration Ranges
Normal Sera

| Species | IgG (mg/mL) | IgM (mg/mL) | IgA (mg/mL) | % κ/λ |
|---|---|---|---|---|
| Human | Total: 7.5-22<br>IgG1: 5-9.5<br>IgG2: 2.2-4.8<br>IgG3: 0.4-1.0<br>IgG4: 0.1-0.6 | 0.2-2.8 | 0.5-3.4 | 67/33 |

Tryptic Digestion for Human Serum

Figure 4:
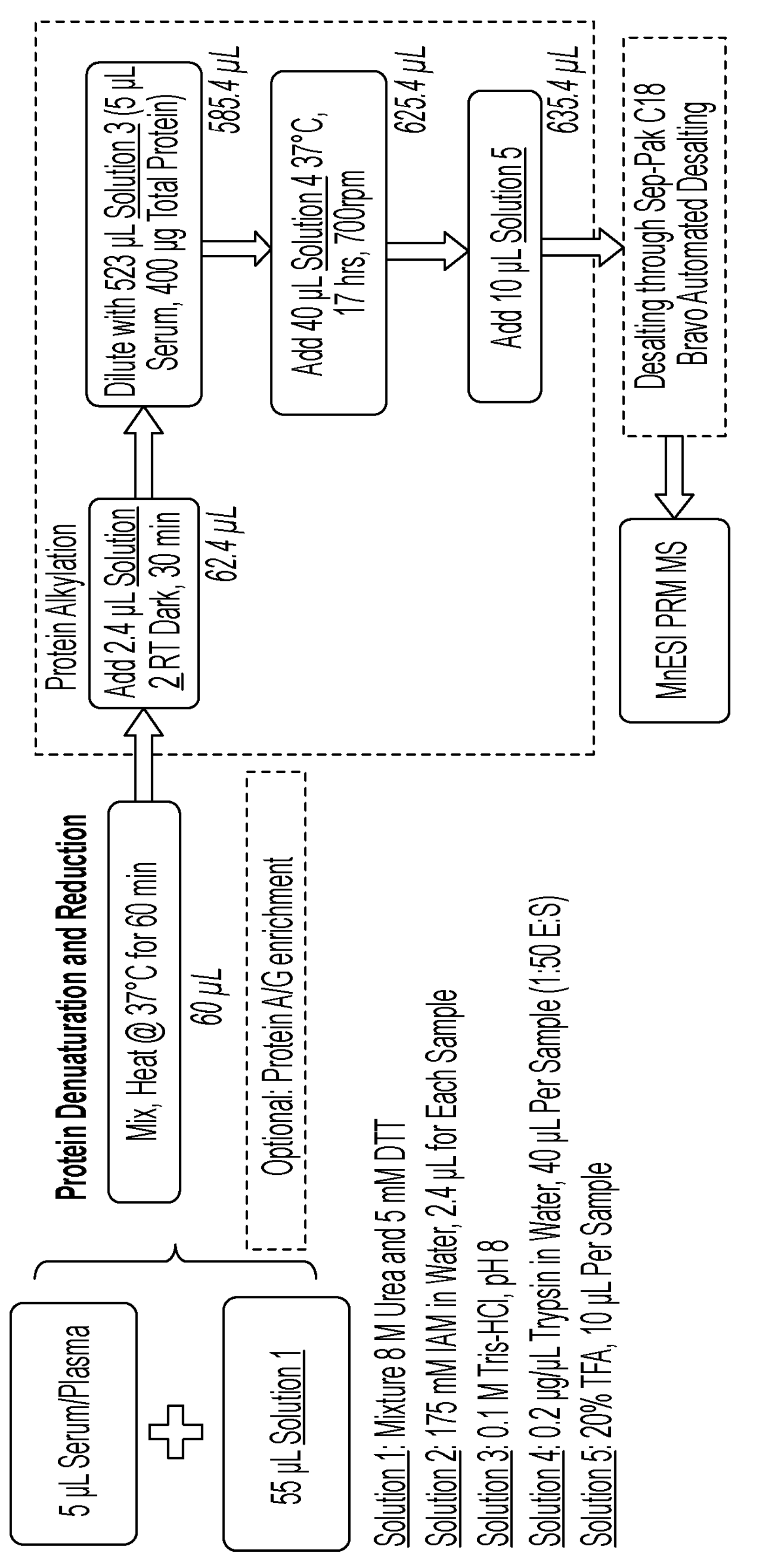
FIG. 4 illustrates the protocol for trypsin digestion of human serum, according to an exemplary embodiment.

FIG. 4 illustrates the following protocol for trypsin digestion of human serum. 5 μL of human serum or standard IgG mixtures were diluted in 60 μL of denaturation buffer containing 8 M urea and 5 mM of dithiothreitol and incubated at 37° C. for one hour. The reduced and denatured samples were alkylated by addition of 2.4 μL of 175 mM iodoacetamide and incubation in the dark at room temperature for 30 minutes. The urea concentration was then adjusted to 1 M by adding Tris buffer (pH 8.0). The samples were then digested with recombinant trypsin (Promega) at a 1:50 enzyme-to-substrate ratio at 37° C. for 17 hours, with shaking at 700 rpm. Digested samples were desalted using Sap-Pak C18 cartridges (Waters) and reconstituted in 800 μl 0.1% formic acid, and further diluted 10-fold prior to LC-MS analysis.

Microflow LC-PRM-MS

Figure 5:
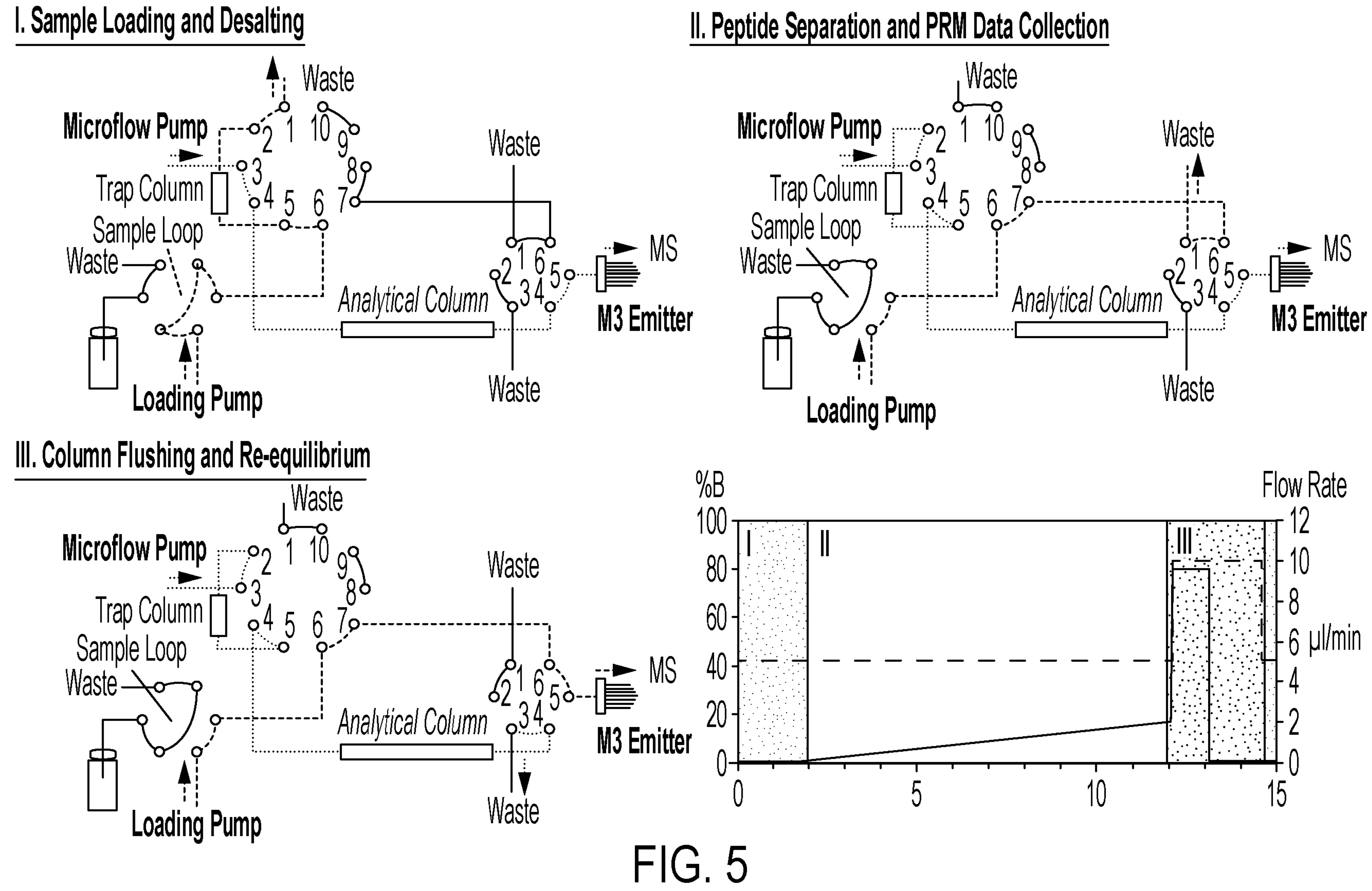
FIG. 5 shows representative diagrams of liquid chromatography (LC) pump and switching valve conditions, according to an exemplary embodiment.

Microflow LC was implemented on an UltiMate™ 3000 HPLC system (Thermo Fisher Scientific). A classic flowmeter with a capillary flow selector was installed to deliver a stable flow rate 1-10 μL/min. Sample corresponding to 400 ng of serum proteins was injected from the sample loop. The injected sample was first purified and condensed in a trapping column (0.3 mm i.d., 2 cm length) for ten column volumes then eluted to an analytical column (0.3 mm i.d., 150 mm Length). The column outlet tubing was connected to a divert valve then connected to an MnESI source equipped with an 8-nozzle emitter with 10 μm tip diameter (Newomics). FIG. 5 shows representative diagrams of the LC pump and switching valve conditions. Sample was loaded and desalted through a loading pump (Step I). Peptides were separated through an analytical column under 5 μl/min flow rate driven by microflow pump. Eluted peptides were introduced to an ion source through M3 emitter The MnESI source was interfaced to an Orbitrap Eclipse™ Tribrid™ mass spectrometer (Thermo Fisher Scientific). The ion-transfer tube temperature was set at 275° C., and the ionization voltage was set at 3500 V globally. During the data acquisition, a full scan spectrum was acquired followed by a series of PRM scans with a scheduled target m/z of 1.6 m/z isolation window (as shown in Table 7). The selection of glycopeptides to be monitored and the retention time were determined using historical DDA datasets acquired on the same system. For the full scan acquisition, the following parameters were set: scan range, 380-1700 (m/z); RF Lens, 40%; normalized AGC target, 300%; maximum injection time, 50 milliseconds. For the PRM scan acquisition, the following parameters were set: RF Lens, 40%, normalized AGC Target, 2000%; maximum injection time, 122 milliseconds. Multiplexing precursor isolation was enabled for simultaneously isolating different charge states of the same glycopeptide. HCD energy for PRM scans was optimized.

Data Processing

Integration of extracted ion chromatogram peaks of all PRM transitions (e.g., Precursors, Y ions, b ions, and y ions) were carried out using Skyline Daily software (University of Washington). To improve the confidence of peak determination, a glycopeptide spectra library (recording the retention time and ID match for each glycopeptide) was built based on historical DDA data and imported to the Skyline document with PRM data.

Calculation Schemes

Partition of Total Y1 for IgG3 and IgG4

Partition of Total Y1 for IgG3

$$T1(IgG3) = Y1(\text{total}) \times \frac{y4(IgG3)}{y4(IgG3) + y4(IgG4)} \quad \text{Equation 1}$$

Partition of Total Y1 for IgG4

$$Y1(IgG4) = Y1(\text{total}) \times \frac{y4(IgG4)}{y4(IgG3) + y4(IgG4)} \quad \text{Equation 2}$$

where Y1 (IgG3) represents the peak area of the Y1 ion of IgG3 (i.e., EEQYN (GlcNAc) STFR(SEQ ID NO: 8)); Y1 (IgG4) represents the peak area of the Y1 ion of IgG4 (i.e., EEQFN (GlcNAc) STYR(SEQ ID NO: 9)); Y1 (total) represents the total peak area of the detected Y1 ion for IgG3 and IgG4; y4 (IgG3) represents the peak area of the y4 ion of IgG3 (i.e., STFR(SEQ ID NO: 5)+); y4 (IgG4) represents the peak area of the y4 ion of IgG4 (i.e., STYR(SEQ ID NO: 7)+).

Glycan Trait Calculation

Percent Fucose $$\% \, Fuc = \sum_{\substack{all\\glycan}} PA \times \#Fuc \Big/ \sum_{\substack{all\\glycan}} PA \quad \text{Equation 3}$$

Percent Galactose $$\% \, Gal = \sum_{\substack{all\\glycan}} PA \times \#Gal \Big/ \sum_{\substack{all\\glycan}} PA \times \#Arm \quad \text{Equation 4}$$

Percent Sialic Acid $$\% \, Sia = \sum_{\substack{all\\glycan}} PA \times \#Sia \Big/ \sum_{\substack{all\\glycan}} PA \times \#Arm \quad \text{Equation 5}$$

Percent Terminal N-Acetylglucosamine $$\% \, tGlcNAc = \sum_{\substack{all\\glycan}} PA \times \#tGlcNAc \Big/ \sum_{\substack{all\\glycan}} PA \times \#Arm \quad \text{Equation 6}$$

Percent Terminal Galactose $$\% \, tGal = \sum_{\substack{all\\glycan}} PA \times \#tGal \Big/ \sum_{\substack{all\\glycan}} PA \times \#Gal \quad \text{Equation 7}$$

TABLE 3

Major and Minor Human IgG N297 Glycoforms

| Glycans to be Monitored | | Information |
|---|---|---|
| FA2 | A2 | Fucosylation/ |
| FA2G1 | A2G1 | Afucosylation/ |
| FA2G2 | A2G2 | Galactosylation |
| FA2G1S1 | | Sialyation |
| FA2G2S1 | | |
| FA2G2S2 | | |
| FA3/FA2B | | Bisecting |
| FA3G1/FA2BG1 | | |
| FA3G2/FA2BG2 | | |
| Man-5 | | Maturity |

Trypsin digestion of human IgGs can produce regular Fc N-glycopeptides, as well as miscleaved Fc N-glycopeptides that contain additional N-terminus threonine, lysine, proline, and arginine residues. Therefore, the ionization potentials of miscleaved human IgG Fc N-glycopeptides were examined because their ionization potentials may be higher due to their extra lysine and arginine residues. Table 4 shows the regular and miscleaved human IgG Fc N-glycopeptides produced by trypsin digestion and the transitions of each that were examined.

TABLE 4

Potential Transitions of Regular and Miscleaved IgG Fc N-Glycopeptides

| IgG Subclass | Precursor Regular | Miscleaved | Transitions |
|---|---|---|---|
| IgG1 | EEQYNSTYR (SEQ ID NO: 3) | TKPREEQYNSTYR (SEQ ID NO: 11) | Precursor (without isolation), Precursor (t-SIM), |
| IgG2 | EEQFNSTFR (SEQ ID NO: 10) | TKPREEQFNSTFR (SEQ ID NO: 12) | Oxonium Ions, |
| IgG3 | EEQYNSTFR (SEQ ID NO: 2) | TKPREEQYNSTFR (SEQ ID NO: 13) | Y1 (pep + 203) or Y* (pep + 83) Ions |
| IgG4 | EEQFNSTYR (SEQ ID NO: 1) | TKPREEQFNSTYR (SEQ ID NO: 14) | b or y Ions (peptide fragments) |

where PA represents the peak area of a selected transition for each glycan; #Fuc, #Gal, #Sia, #tGlcNAc, #tGal, and #Arm represent the number of fucose, galactose, sialic acid, terminal N- acetylglucosamine, terminal galactose, and the branching arm, respectively, for each glycan.

Design of High-Throughput Microflow LC-MnESI-PRM System and Optimization of Experimental Conditions A target-based method was used to monitor fucosylated, afucosylated, sialylated, tri-antennary or bisected, and high-mannose human IgG N297 glycoforms. Table 3 shows the three major human IgG N297 glycoforms, which are fucosylated: FA2, FA2G1, and FA2G2. Table 3 also shows low abundance afucosylated, sialylated, bisected, and high-mannose human IgG N297 glycoforms. Based on the relative abundance of the glycans shown in Table 3, information could be obtained related to glycan maturity, fucosylation, galactosylation, sialyation, etc., which could be used for finding patterns across samples.

Figure 6A:
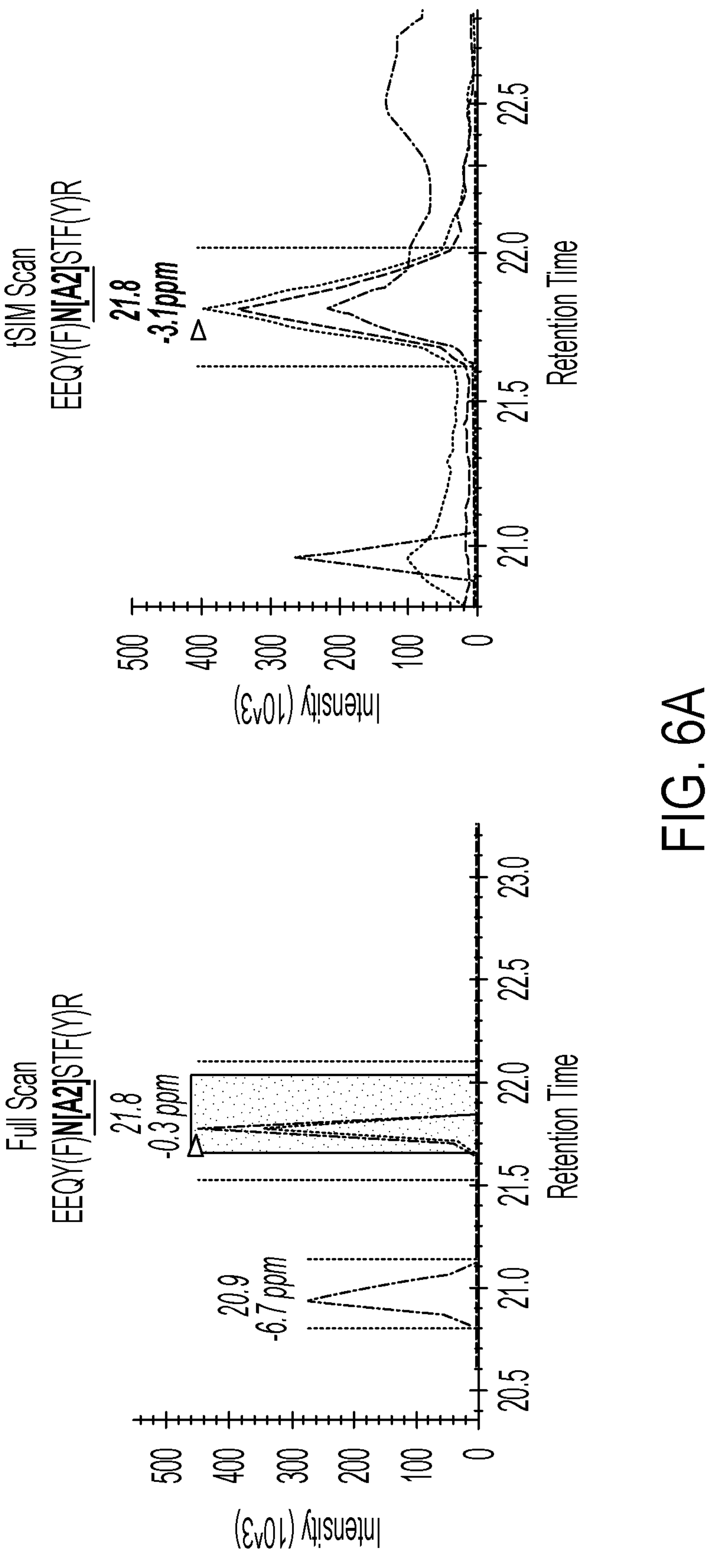
FIG. 6A shows the extracted ion chromatogram peak signals generated in full (left) and t-SIM (right) scan modes for low abundance afucosylated glycoforms (A2) of IgG3 and IgG4, according to an exemplary embodiment (EEQY(F)N[A2]STF(Y)R (SEQ ID NO: 56)).

A targeted scan, like t-SIM, monitors precursors and is more sensitive than a full scan. For instance, FIG. 6A shows that target-based analysis of a low abundant afucosylated glycoform (A2) using t-SIM (right panel) is more sensitive and has a better signal-to-noise ratio (S/N) than full scan DDA analysis (left panel). For the t-SIM scan, the first three isotopic peaks were monitored (e.g., shown as different traces). However, full and tSIM scans could not discriminate IgG3 and IgG4 signals, suffered from poor peak shapes, and suffered from the presence of interfering baseline signal.

Figure 6B:
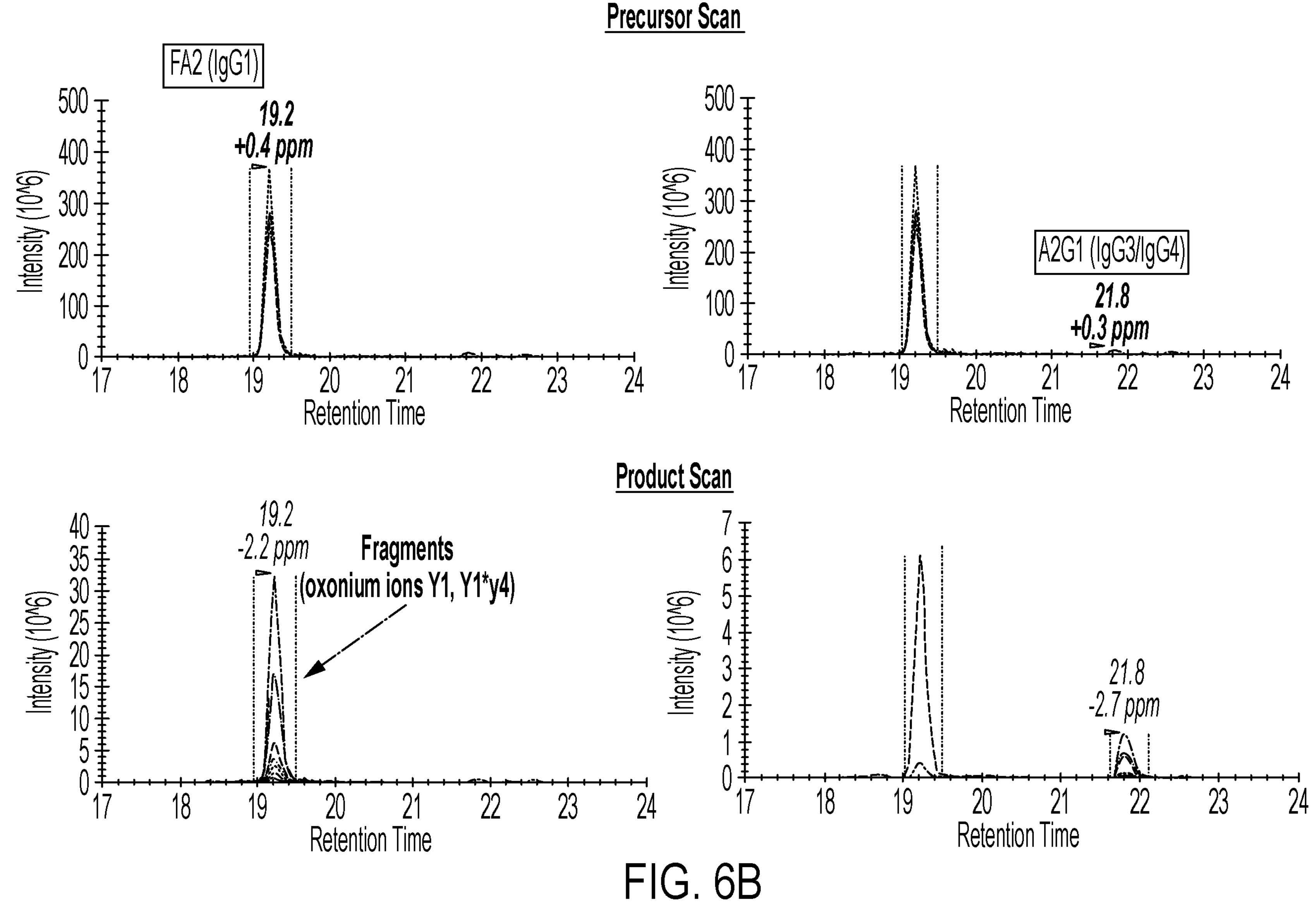
FIG. 6B shows the extracted ion chromatogram peak signals of precursors and products generated for a fucosylated (FA2) IgG1 glycoform (left) and afucosylated (A2G1) IgG3/4 glycoform, according to an exemplary embodiment.
Figure 6C:
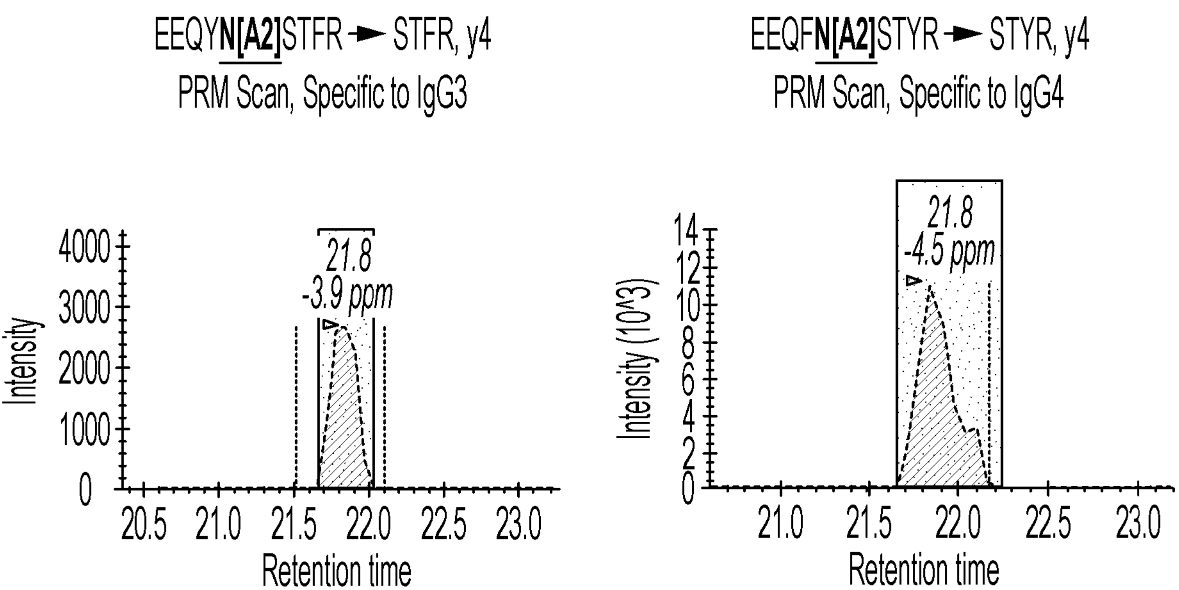
FIG. 6C shows PRM mode allowed to monitor two IgG3 and IgG4 glycopeptides in different transition channels with satisfied peak shape and baseline noise, although the absolute intensity was lower than precursor, according to an exemplary embodiment.
Figure 6C:
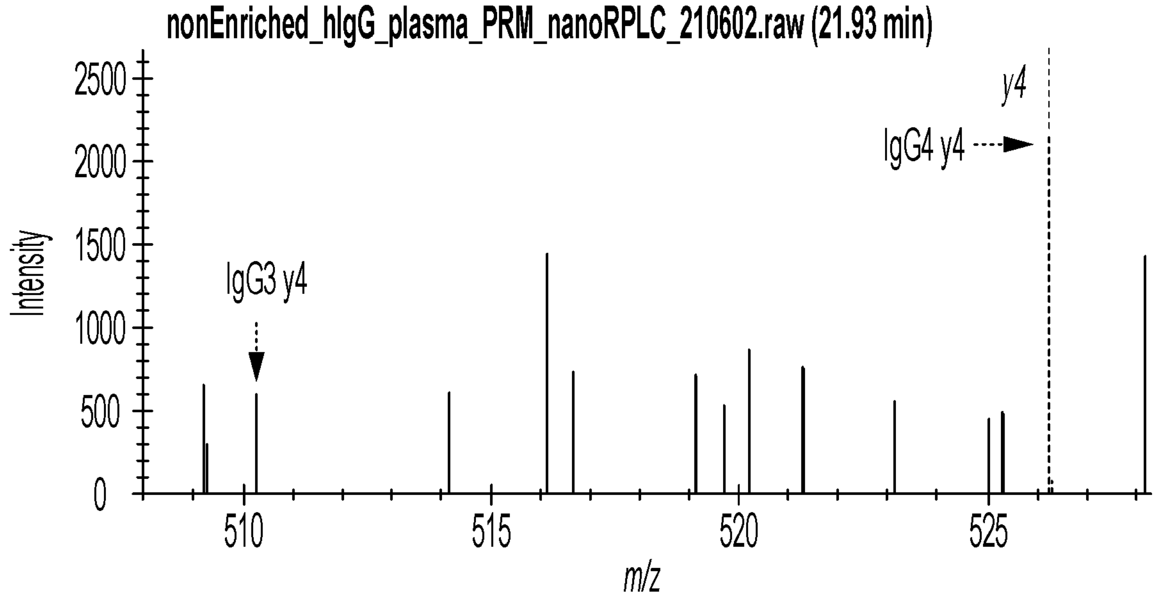

Parallel reaction monitoring (PRM)-based analysis monitors precursors as well as products. The multiple scans performed during PRM-based analysis are advantageous for distinguishing, for example, a fucosylated glycoform of one subclass from an afucosylated glycoform of a different subclass with identical mass. For example, FIG. 6B shows the precursor (top) and product (bottom) scans of a fucosylated IgG1 glycoform (FA2) (left panel) and an afucosylated IgG3 or IgG4 glycoform (A2G1) (right panel) in which the fake peak could be singled out due to lack of multiple product scans, though the oxonium, Y or Y*, ions that are conventionally used for quantitation do not have the capability to distinguish IgG3 and IgG4. However, b and y ions (e.g., peptide backbone fragments) could be used to distinguish IgG3 and IgG4. FIG. 6C shows an exemplary embodiment in which PRM y4 scans specific for afucosylated glycoforms (A2) of IgG3 and IgG4 could be used to distinguish and quantitate IgG3 and IgG4.

Table 5 shows a summary of pros and cons of all the available methods of transition. Y1 ions have high sensitivity but poor selectivity for distinguishing IgG3 and IgG4. Conversely, y4 ions have poor sensitivity but excellent selectivity for distinguishing IgG3 and IgG4. Therefore, the orthogonal information provided by Y1 and y4 can be used for subclass specific quantitation of IgGs, including distinguishing and quantitating IgG3 and IgG4.

TABLE 5

Pros and Cons of All Available Methods of Transition

| Method of Transition | Sensitivity | Selectivity (Glycoform) | Selectivity (IgG3/4) |
|---|---|---|---|
| Full Scan | ☑ | ☑ | ☒ |
| t-SIM | ☑ | ☑ | ☒ |
| Oxonium | ☑ | ☒ | ☒ |
| Y1, Y1* | ☑ | ☑ | ☒ |
| y4 | ☑ | ☑ | ☑ |

Figure 7A:
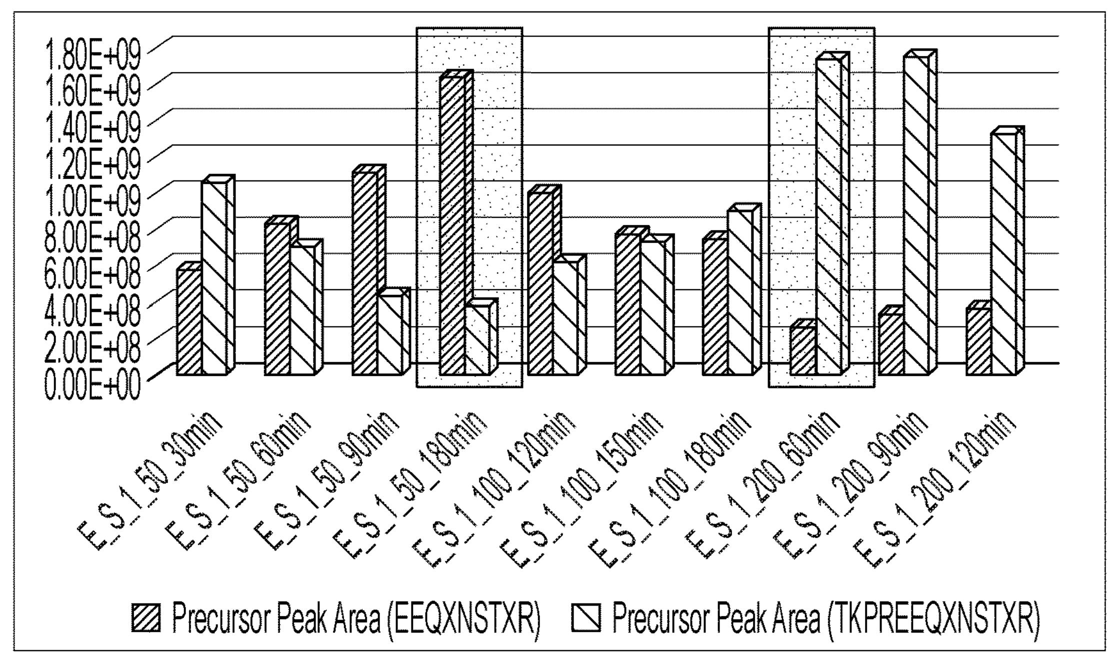
FIG. 7A shows the relative abundance of regular and miscleaved IgG3/4 precursors formed using various enzyme to substrate (E/S) ratios and digestion times, according to an exemplary embodiment. X=Phenylalanine or Tyrosine (EEQXNSTXR (SEQ ID NO: 15) and TKPREEQXNSTXR (SEQ ID NO: 16)).
Figure 7B:
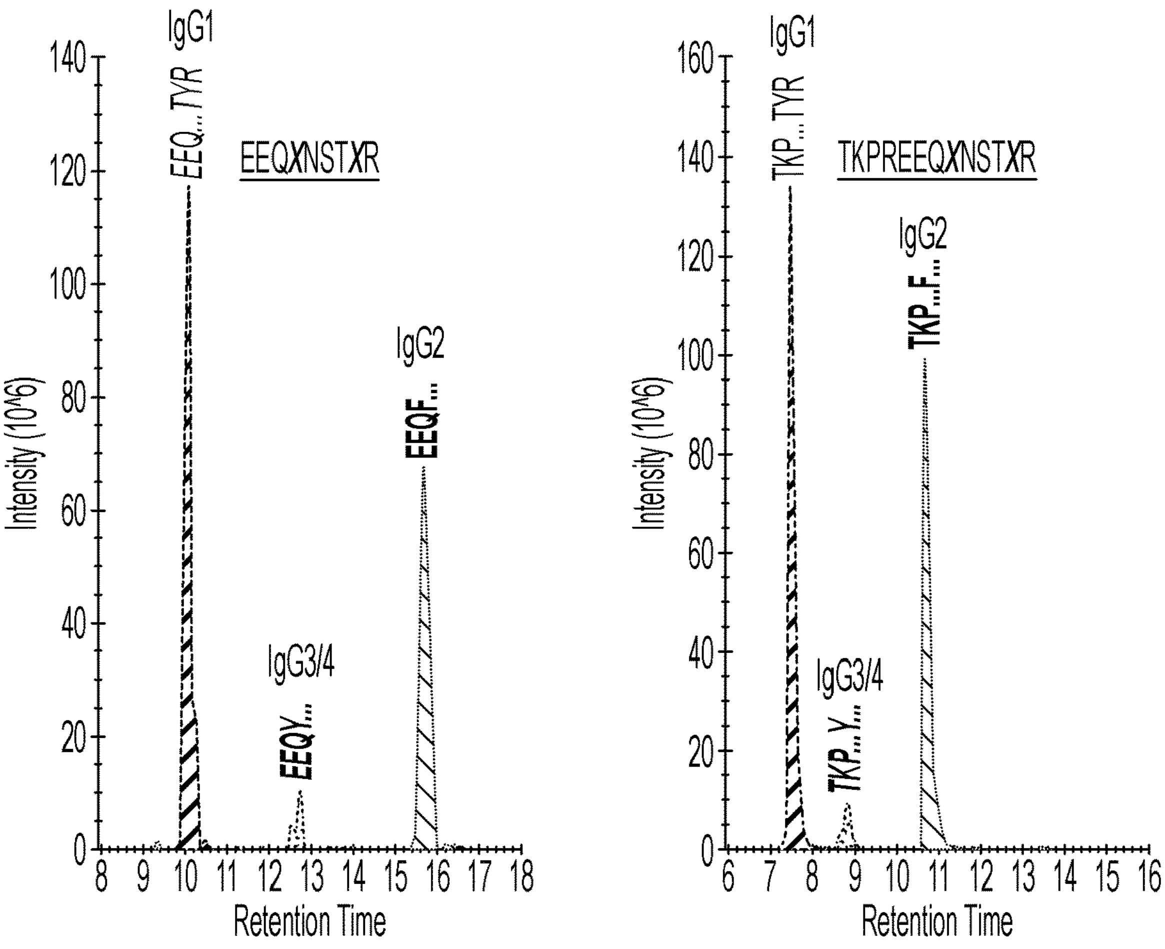
FIG. 7B shows the separation of regular and miscleaved IgG precursors formed using an E/S ratio of 1:50 in a 180-minute digestion and an ES ratio of 1:200 in a 60-minute digestion, respectively, according to an exemplary embodiment. X=Phenylalanine or Tyrosine (EEQXNSTXR (SEQ ID NO: 15); TKPREEQXNSTXR (SEQ ID NO: 16); EEQY (SEQ ID NO: 71); and EEQF (SEQ ID NO: 55)).

FIG. 7A shows the relative abundance of regular and miscleaved IgG3/4 precursors generated using various enzyme to substrate ratios and digestion times. The two digests highlighted in red in FIG. 7A contained maximal amounts of regular (left) and miscleaved (right) IgG3/4 precursors, which comprised approximately 80% of the total population. FIG. 7B and Table 6 show that the IgG3/4 precursor peak area of the two digests highlighted in red in FIG. 7A were approximately equal. However, FIG. 7B shows that the separation of each IgG subclass was better for the regular precursors (left panel) than the miscleaved precursors (right panel). Table 6 shows that the fragmentation efficiency of the miscleaved IgG3/4 precursors was about half that of the regular IgG3/4 precursors, even though the levels of the regular and miscleaved IgG3/4 precursors were approximately equal.

TABLE 6

Ionization and Fragmentation Efficiency of IgG Fc N-Glycopeptides

| Sample | Precursor Peak Area | y4 Peak Area | b4 or b8 Peak Area |
|---|---|---|---|
| EEQXNSTXR (SEQ ID NO: 15) | $1.64 \times 10^9$ | $2.94 \times 10^6$ | $8.75 \times 10^5$ |
| TKPREEQXNSTXR (SEQ ID NO: 16) | $1.74 \times 10^9$ | $1.65 \times 10^6$ | $5.17 \times 10^5$ |
| Fold Difference | 0.9 | 1.8 | 1.7 |

Figure 8:
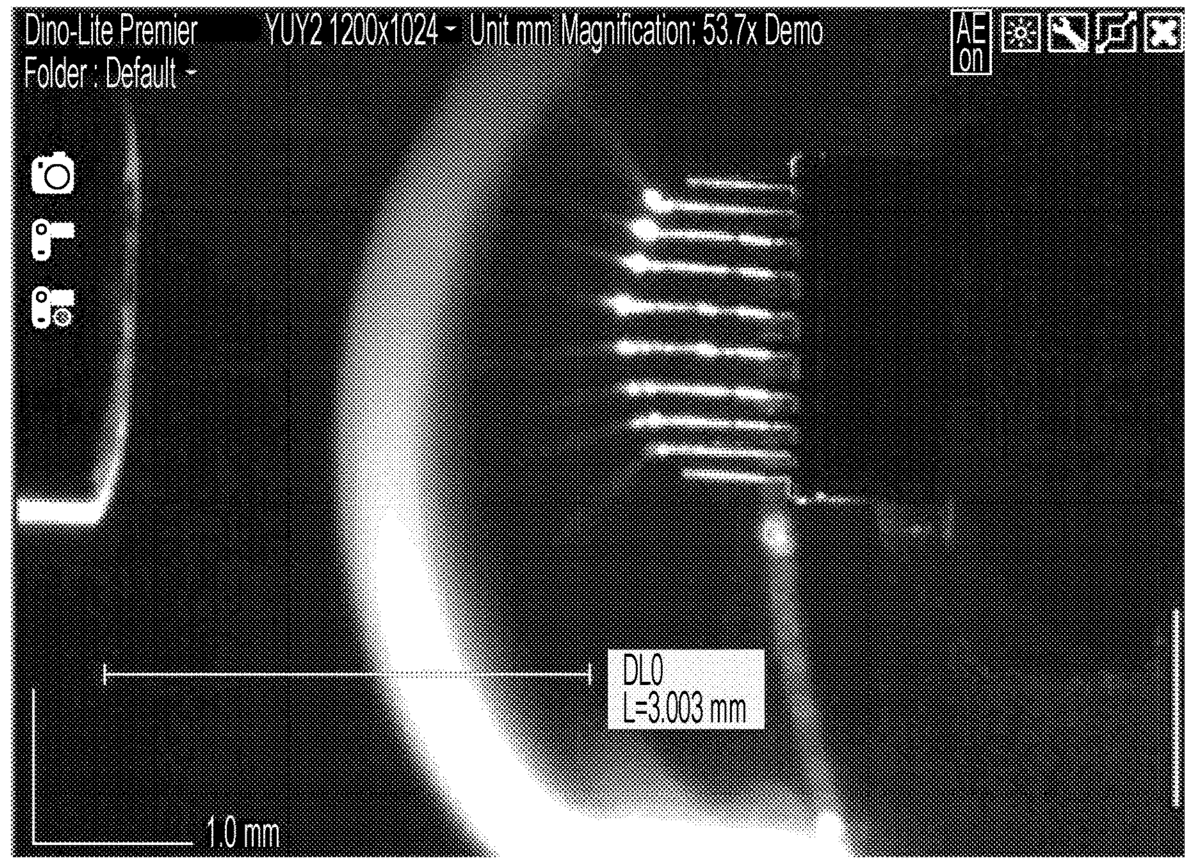
FIG. 8 shows a silicon M3 multi-nozzle emitter that is compatible with microflow rates and produces a flow from each emitter, eight in total, that resembles nanoflow, according to an exemplary embodiment.
Figure 9A:
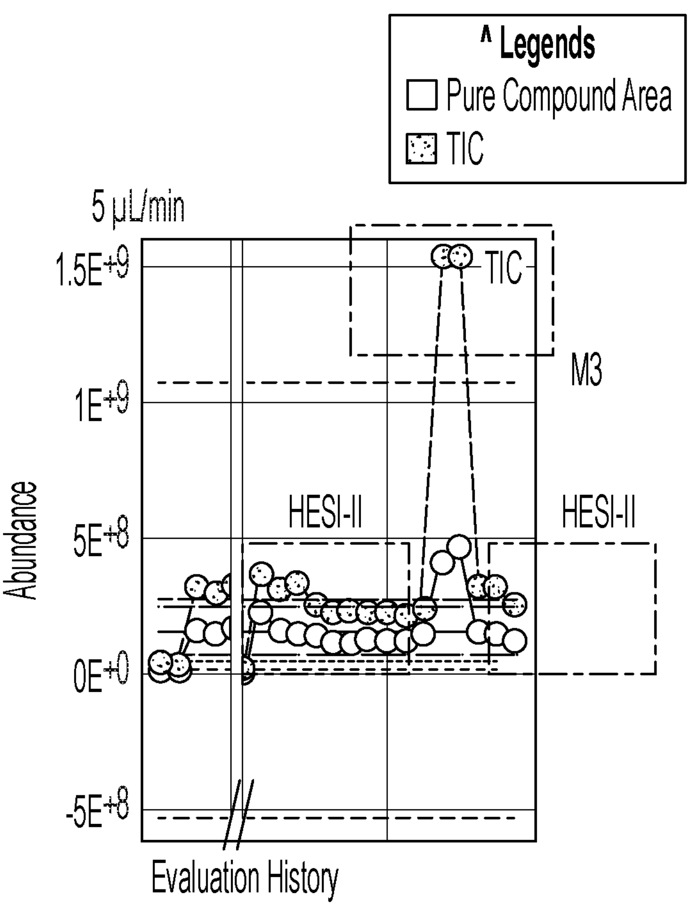
FIG. 9A shows the signal and sensitivity for Calmix Standard Injection obtained using the optimized MnESI-PRM method, according to an exemplary embodiment.
Figures 1, 9B:
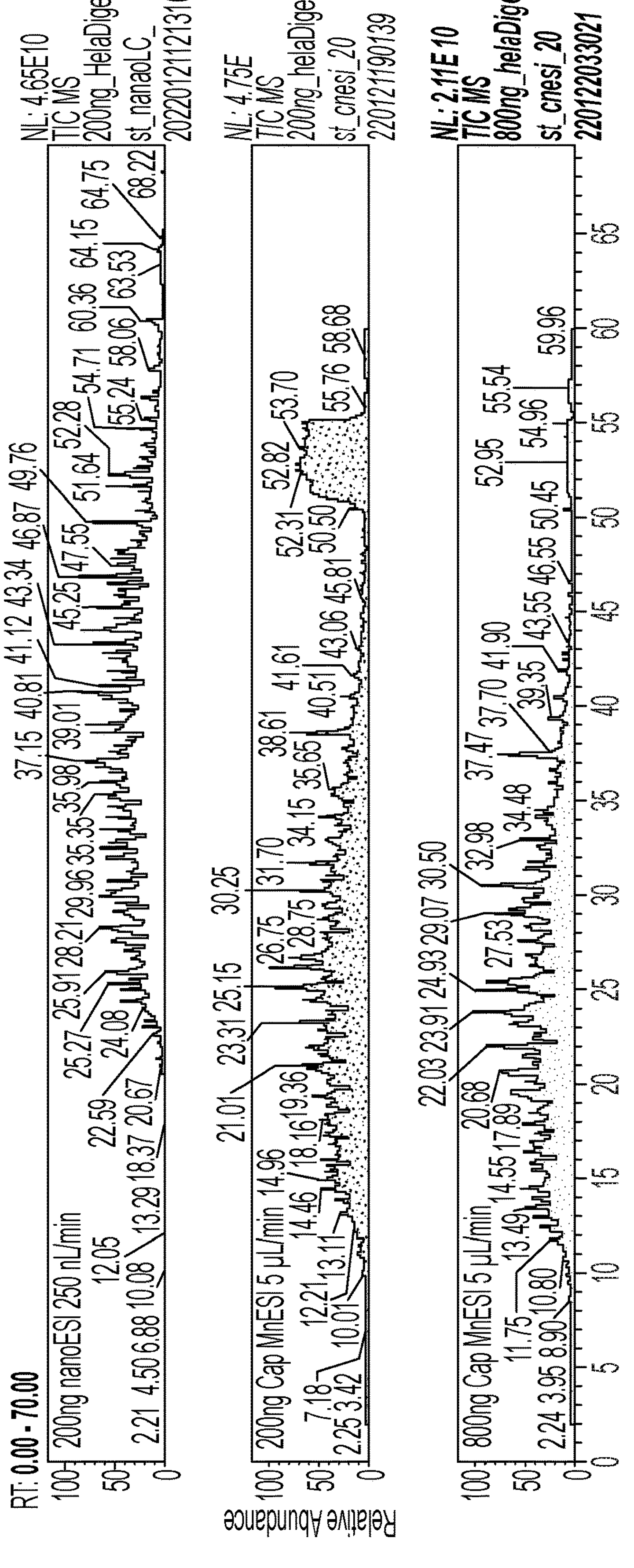
Figures 2, 9B:
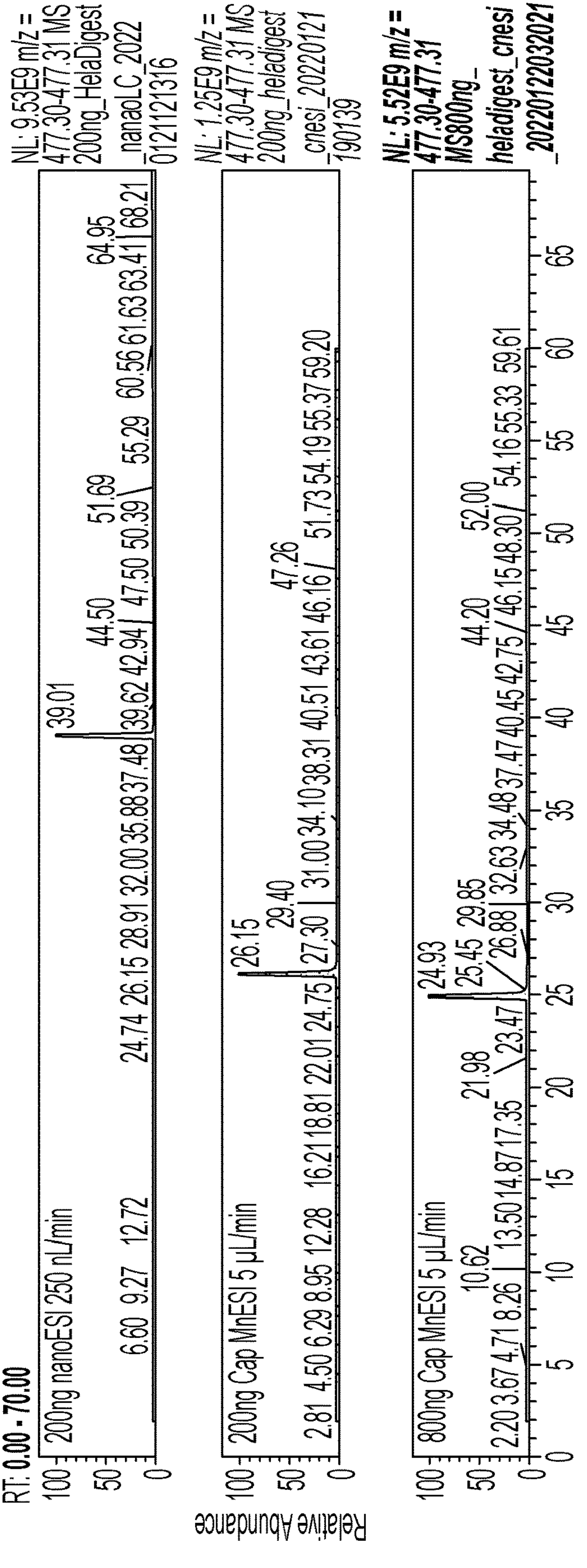
Figure 9B:
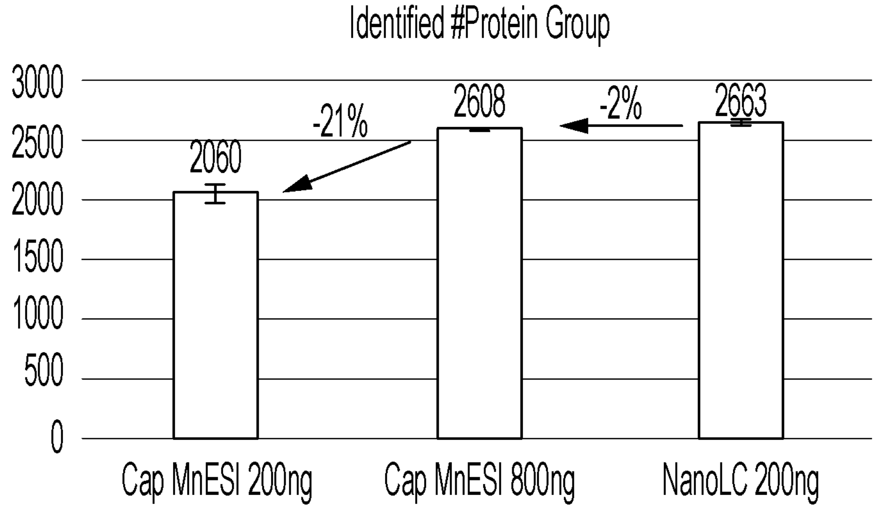
Figure 3:
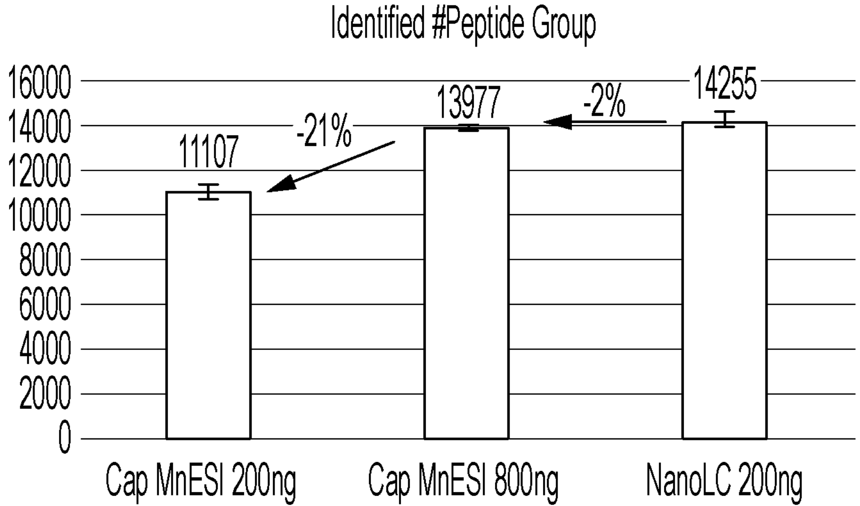

Flow rate for LC was optimized to achieve the best MS signal. Generally, a MS signal may benefit from a lower flow rate because of improved desolvation, but a lower flow rate may broaden the peak, decrease the sample concentration at the apex and require longer run times. In contrast, a microflow rate of 1-50 μL/min can provide robustness and throughput, but lacks sensitivity. However, FIG. 8 shows a silicon M3 multi-nozzle emitter that is compatible with microflow rates and produces a flow from each emitter, 8 in total, that resembles nanoflow. An M3 multi-nozzle emitter was used to develop a high throughput microflow MS (MnESI MS) assay that could use as short as 20-minute gradient ("the optimized method"). FIG. 9A shows that the optimized method improved the signal and sensitivity for Calmix Standard Injection. HeLa digests were used to compare the optimized method to nanoflow LC. The platform was tested using Hela digests. FIGS. 9B-1, 9B-2 and 9B-3 shows that the optimized method and nanoflow LC identified a similar number of protein/peptide groups and produced similar intensities and peak shapes, though the optimized method reduced dead volume, which reduced the overall run time of samples.

Testing various flow rates and evaluating the peak shapes and intensity of the total ion chromatograms (TIC) demonstrated that a 5 μl/min flow rate provided a good MS signal. To shorten the run time per sample acquisition, the gradient was ramped immediately to 100% mobile phase B after the IgG glycopeptides were eluted to quickly flush out the remaining peptides. The flow rate was then increased to 10 μl/min to further reduce the required time for column flushing and re-equilibration. To avoid potential emitter clogging and front-end contamination of the mass spectrometer caused by the large amount of peptide and undigested protein eluates during this step, the LC outlet was diverted to waste after the gradient was switched to high organic phase and high flow rate. The stable spray could not be recovered if the M3 emitter was dry temporarily while the high voltage was still being applied. Therefore, a compensate flow from the loading pump line could keep the M3 emitter hydrated when the sample was diverted to the waste, as illustrated in FIG. 5. The gradient was further optimized to separate the clusters of different IgG subclasses from one another. The final optimized gradient contained a 12-minute gradient for peptide trapping and glycopeptide separation and the total LC run time was 20 minutes for each sample, as illustrated in FIG. 5.

Based on the historical data, the thirteen most representative glycans for each IgG subclass were monitored using target-based methods. From these glycans, the most common glycan traits that reflected the biosynthesis of glycans for IgGs could be interpreted, including fucosylation, galactosylation, sialylation, bisecting or tri-antenary, high-mannose, though some (e.g., afucosylated, sialylated, high mannose) were not highly abundant in normal human serum. In addition, the two most abundant charge states (+2 and +3) instead of a single charge state were selected during multiplexed precursor isolation to eliminate the bias caused by charge state distribution, which could vary across different glycoforms or between different runs.

Figure 10:
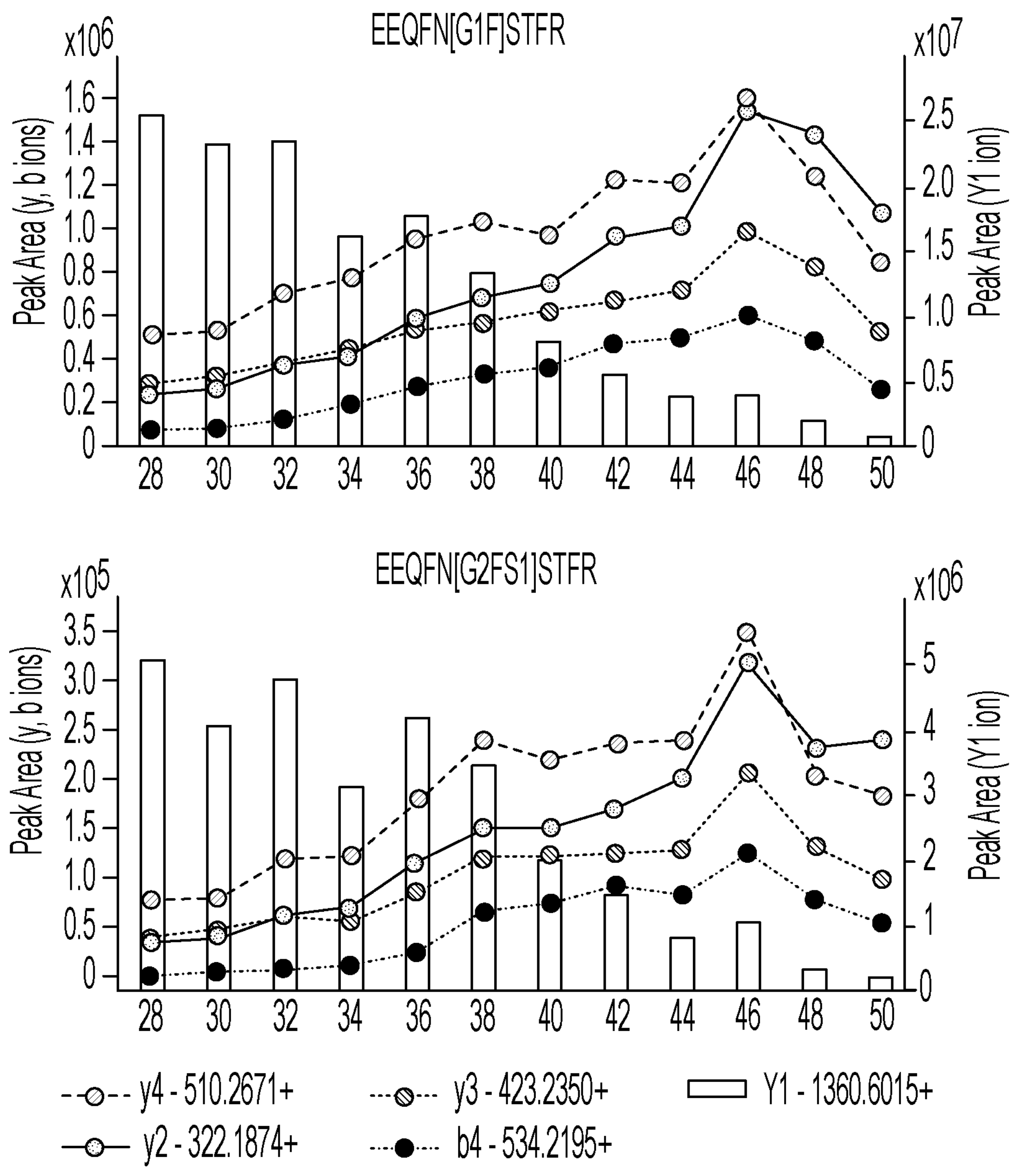
FIG. 10 shows the collision energy optimization for glycopeptide product ions generated due to peptide bond fragmentation (y, b ions) that allows IgG3 and IgG4 differentiation and glycosidic bond fragmentation (Y1 ion), according to an exemplary embodiment (EEQFN[G1F]STFR (SEQ ID NO: 59) and EEQFN[G2FS1]STFR (SEQ ID NO: 51).

Collision energy (CE) was optimized for both the regular and miscleaved precursor glycopeptides presented in Table 4. Regular precursor glycopeptides were optimally generated using an overnight digest with a 1:50 enzyme to substrate ratio, whereas miscleaved precursor glycopeptides were optimally generated using a 60-minute digest with a 1:200 enzyme to substrate ratio. In order to generate sufficient level of peptide backbone fragmentation, the collision energy in the HCD cell was titrated based on the performance of IgG1 glycopeptides. FIG. 10 shows that the backbone fragmentation increased as the CE increased, yielding four product ions ($y2^+$, $y3^+$, $y4^+$, and $b4^+$) that can be used to differentiate IgG3 and IgG4, and the maximum was reached at CE 46. Within these ions, $y4^+$ exhibited highest yield for all glycoforms at each collisional energy.

As far as the product ions caused by saccharide diester bond cleavage ($P^+$, $Y1^+$) and saccharide cross-ring fragmentation ($Y1^{*+}$), they all monotonically decrease as CE increased, where $Y1^+$ exhibited higher yield than others. The yield of $Y1^+$ were still much higher than $y4^+$ even under the condition where $y4^+$ production is mostly favored (i.e., CE=48). Therefore, $Y1^+$ was selected as a general quantifier for better sensitivity of each glycopeptide, while $Y4^+$ was only used for distinguishing IgG3 and IgG4 and calculating their relative ratio. Finally, CE-38 was used to achieve both good yield for $y4^+$ and $Y1^+$. Under CE=38, the yield of $y4^+$ was around 75% of the maximum value and was found to be sufficient for the PRM experiment. In addition, the alternative version of N297-containing peptides possessing a single missed cleavage site (TKPREEQXNSTXR)(SEQ ID NO: 16) can be used as the precursors to be monitored in a PRM analysis and therefore the profile of peptide backbone prone to fragmentation was also inspected during the same CE titration experiment. Moreover, FIG. 7B shows that the individual IgG subclass clusters of TKPREEQXNSTXR (SEQ ID NO: 16) glycopeptides were eluted very closely with the same gradient compared to the EEQXNSTXR(SEQ ID NO: 15) clusters, increasing the number of co-scheduled targets. As a result, the regular version of N297-containing glycopeptides (EEQXNSTXR)(SEQ ID NO: 15) were selected as the precursors for the PRM analysis. The full list of targets is shown in Table 7.

TABLE 7

List of Targeted Glycopeptide Precursors

| Glycopeptides | Protein | Precursor m/z z = 2 | Precursor m/z z = 3 | Retention Time (min) |
|---|---|---|---|---|
| EEQYN[G0]STYR (SEQ ID NO: 17) | IgG1 | 1244.50 | 830.00 | 7.8-9.5 |
| EEQYN[G1]STYR (SEQ ID NO: 18) | IgG1 | 1325.52 | 884.02 | 7.8-9.5 |
| EEQYN[G2]STYR (SEQ ID NO: 19) | IgG1 | 1406.55 | 938.04 | 7.8-9.5 |
| EEQYN[G2F]FTYR (SEQ ID NO: 20) | IgG1 | 1479.58 | 986.72 | 7.8-9.5 |
| EEQYN[Man5]STYR (SEQ ID NO: 21) | IgG1 | 1203.47 | — | 7.8-9.5 |
| EEQYN[G0F + GlcNAc]STYR (SEQ ID NO: 22) | IgG1 | 1419.07 | 946.38 | 7.8-9.5 |
| EEQYN[G1F + GlcNAc]STYR (SEQ ID NO: 23) | IgG1 | 1500.09 | 1000.40 | 7.8-9.5 |
| EEQYN[G2F + GlcNAc]STYR (SEQ ID NO: 24) | IgG1 | 1581.12 | 1054.42 | 7.8-9.5 |
| EEQYN[G0F + GlcNAc]STYR (SEQ ID NO: 22) or EEQYN[G1]STFR (SEQ ID NO: 25) | IgG1 or IgG3/4 | 1317.53 | 878.69 | 7.8-10.8 |
| EEQYN[G1F]STYR (SEQ ID NO: 26) or EEQYN[G2]STFR (SEQ ID NO: 27) | IgG1 or IgG3/4 | 1398.55 | 932.70 | 7.8-10.8 |
| EEQYN[G0F + GlcNAc]STFR (SEQ ID NO: 28) | IgG1 | 1411.07 | 941.05 | 9.1-10.8 |
| EEQYN[G1F + GlcNAc]STFR (SEQ ID NO: 29) | IgG1 | 1492.10 | 995.07 | 9.1-10.8 |
| EEQYN[G2F]STFR (SEQ ID NO: 30) | IgG3/4 | 1471.58 | 981.39 | 9.1-10.8 |
| EEQYN[G2F + GlcNAc]STFR (SEQ ID NO: 31) | IgG3/4 | 1573.12 | 1049.08 | 9.1-10.8 |
| EEQYN[Man5]STFR (SEQ ID NO: 32) | IgG3/4 | 1195.47 | — | 9.1-10.8 |
| EEQYN[G0]STFR (SEQ ID NO: 33) | IgG3/4 | 1236.50 | 824.67 | 9.1-10.8 |
| EEQYN[G0F]STFR (SEQ ID NO: 34) or EEQFN[G1]STFR (SEQ ID NO: 35) | IgG3/4 or IgG2 | 1309.53 | 873.36 | 9.1-12.3 |
| EEQYN[G1F]STFR (SEQ ID NO: 36) or EEQFN[G2]STFR (SEQ ID NO: 37) | IgG3/4 or IgG2 | 1390.56 | 927.37 | 9.1-12.3 |
| EEQYN[GFS1]STYR (SEQ ID NO: 38) | IgG1 | 1544.10 | 1029.74 | 9.4-11 |
| EEQYN[G2FS1]STYR (SEQ ID NO: 39) | IgG1 | 1625.13 | 1083.75 | 9.4-11 |
| EEQFN[G0]STFR (SEQ ID NO: 40) | IgG2 | 1228.50 | 819.34 | 10.9-12.6 |
| EEQFN[G0F]STFR (SEQ ID NO: 41) | IgG2 | 1301.53 | 868.02 | 10.9-12.6 |
| EEQFN[1F]STFR (SEQ ID NO: 42) | IgG2 | 1382.56 | 922.04 | 10.9-12.6 |
| EEQFN[G2F]STFR (SEQ ID NO: 43) | IgG2 | 1463.58 | 976.06 | 10.9-12.6 |

TABLE 7-continued

List of Targeted Glycopeptide Precursors

| Glycopeptides | Protein | Precursor m/z z = 2 | Precursor m/z z = 3 | Retention Time (min) |
|---|---|---|---|---|
| EEQFN[Man5]STFR (SEQ ID NO: 44) | IgG2 | 1187.48 | — | 10.9-12.6 |
| EEQFN[G0F + GlcNAc]STFR (SEQ ID NO: 45) | IgG2 | 1403.07 | 935.72 | 10.9-12.6 |
| EEQFN[G1F + GlcNAc]STFR (SEQ ID NO: 46) | IgG2 | 1484.10 | 989.73 | 10.9-12.6 |
| EEQFN[G2F + GlcNAc]STFR (SEQ ID NO: 47) | IgG2 | 1565.12 | 1043.75 | 10.9-12.6 |
| EEQYN[G1FS1]STFR (SEQ ID NO: 48) | IgG3/4 | 1536.10 | 1024.41 | 11.2-12.8 |
| EEQYN[G2FS1]STFR (SEQ ID NO: 49) | IgG3/4 | 1617.13 | 1078.42 | 11.2-12.8 |
| EEQFN[G1FS1]STFR (SEQ ID NO: 50) | IgG2 | 1528.11 | 1019.07 | 12.2-13.8 |
| EEQFN[G2FS1]STFR (SEQ ID NO: 51) | IgG2 | 1609.13 | 1073.09 | 12.2-13.8 |

Method Validation Using Standard Protein of IgG Subclasses

Figure 11:
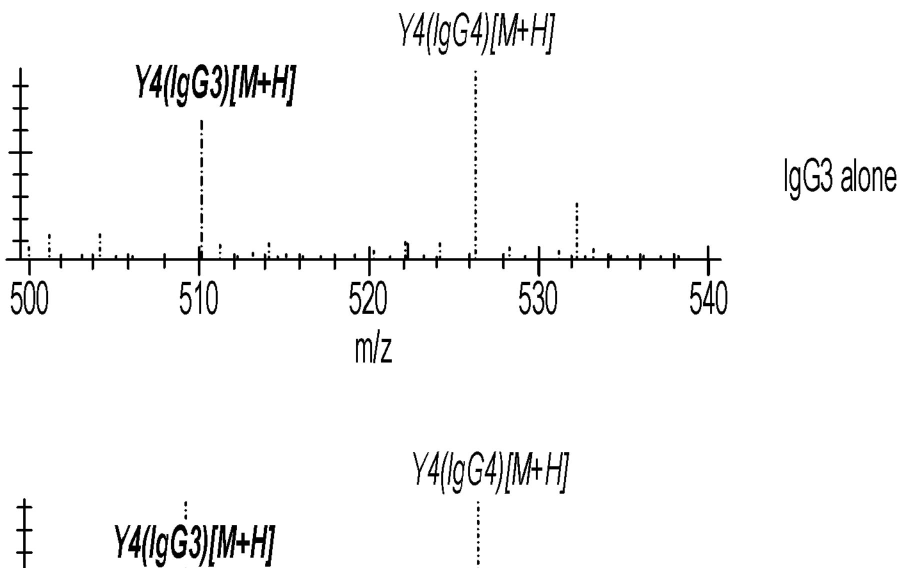
FIG. 11 shows representative MS signals were monitored in two channels for isomeric glycopeptides from IgG3 (EEQYN [FA2G1] STFR (SEQ ID NO: 4)→STFR (SEQ ID NO: 5) +, 510 m/z) and IgG4 (EEQFN [FA2G1] STYR (SEQ ID NO: 6)→STYR (SEQ ID NO: 7) +, 526 m/z) for the standard IgG samples, according to an exemplary embodiment.
Figure 11:
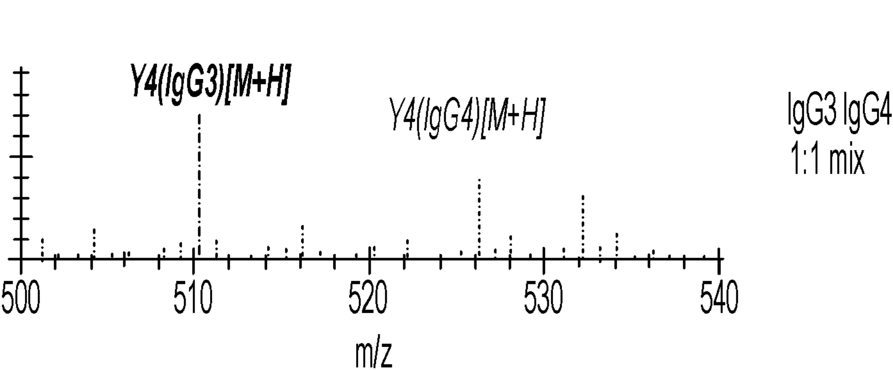

FIG. 11 shows that, for the standard IgGs, y4 from IgG3 (STFR(SEQ ID NO: 5)+, 510 m/z) and IgG4 (STYR(SEQ ID NO: 7)+, 526 m/z) displayed in the same MS/MS spectrum when these two subclasses were co-isolated for HCD fragmentation. Because the mass difference between these two ions corresponds to an oxygen atom (16 Da), the ion with 526 m/z could also be produced during gas-phase oxidation of STFR(SEQ ID NO: 5)+ (IgG3), which interferes with the detection of original STYR(SEQ ID NO: 7)+ from IgG4. Similarly, STYR(SEQ ID NO: 7)+ could undergo gas-phase oxygen loss (−16 Da) or dehydration (−18 Da), and deoxidized species and the third isotope of the dehydration species (both 510 m/z) could also interfere with the detection of original STFR(SEQ ID NO: 5)+ from IgG3. These possibilities were investigated using the sample containing only IgG3 or IgG4. FIG. 11 shows that the levels of ST(F/Y)R(SEQ ID NO: 5 or 7)+ peak converted from the other IgG subclasses in the gas phase were negligible. In addition, FIG. 6A and FIG. 6C show that sensitivity was significantly increased when either y4 or Y1 were monitored compared with the full scan, especially for low abundance glycoforms.

Table 1 shows a series of mixtures of standard IgGs from all four subclasses in the presence of mouse serum, in which IgG1 and IgG2 were fixed at 5000 and 2500 μg/ml, respectively, and IgG3 and IgG4 were varied from 10 to 1000 μg/ml. In Table 1, sample 7 (shaded column) represents general physiological concentrations of the IgGs, which are shown in Table 2. The series of mixtures presented in Table 1 were used to evaluate whether IgG3 and IgG4 glycopeptides could be correctly quantified using y4 ions when both IgG subclasses were present at different ratios. Although mouse serum was selected as the matrix due to the absence of endogenous human IgGs, mouse IgG1 can produce the same glycosite-containing tryptic peptide as human IgG2 (EEQFNSTFR)(SEQ ID NO: 10). Nevertheless, Table 8 shows that the detection of glycopeptides for the other three human IgG subclasses was still evaluated without bias because the corresponding peptides can only be generated by the spiked-in standard human IgGs.

Figure 12A:
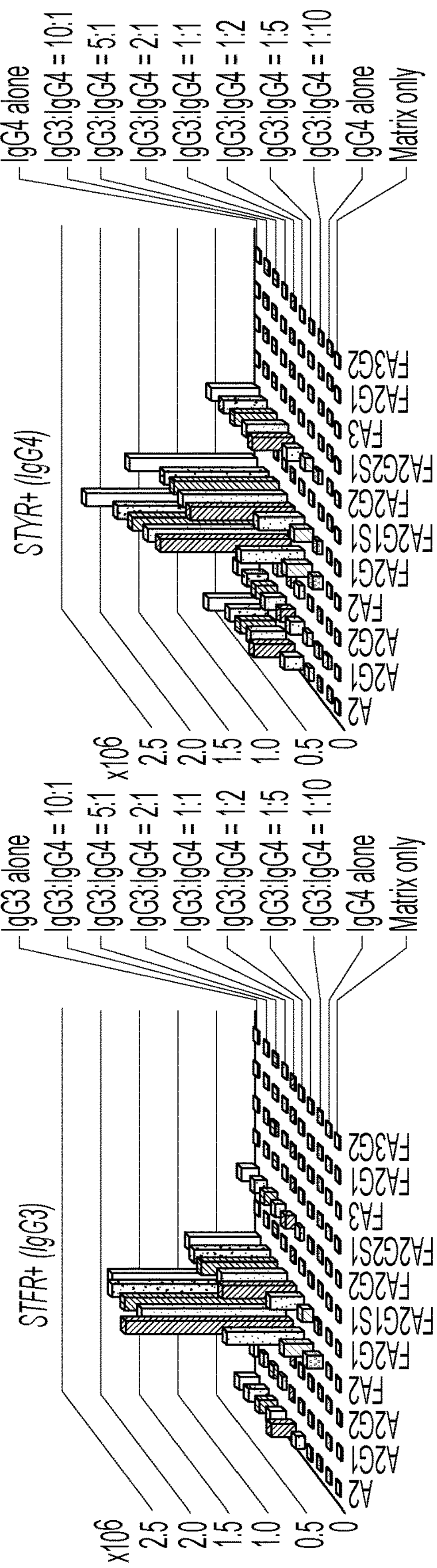
FIG. 12A shows the level of individual glycoforms quantified using absolute extracted peak area of the product ions (STFR (SEQ ID NO: 5)+ for IgG3 and STYR (SEQ ID NO: 7) + for IgG4) in different samples, according to an exemplary embodiment.

FIG. 12A shows that the relative level of major glycoforms from IgG3 and IgG4 could be quantified individually based on the intensity of y4 ion. The profile of the relative level of major glycoforms from IgG3 and IgG4 were different. For example, IgG3 had a lower level of galactosylated glycoforms (according to distribution amongst FA2, FA2G1, and FA2G2), lower level of afucosylated glycoforms (A2, A2G1), and higher level of sialylated glycoforms (FA2G1S1, FA2G2S1) than IgG4. FIG. 12A also shows that the glycoprofile of IgG3 could be preserved when IgG3 and IgG4 were mixed at different ratio, even when IgG3 was less abundant than IgG4 or vice versa. Additionally, several glycoforms, such as FA3G2 in IgG3 and A2G1 in IgG4, did not tend to decrease as the protein concentration decreased, which could have perturbed the observed glycoprofile for the lower level IgGs. Since the aforementioned peaks were also observed when only the matrix is processed, it was concluded that these interference species could have come from mouse serum and may not be an issue during analysis of human serum sample.

TABLE 8

Amino Acid Sequences of Fc Glycosylated Peptides in Human and Mouse IgG Subclasses

| Human | | Mouse | |
|---|---|---|---|
| IgG1 | EEQYNSTYR (SEQ ID NO: 3) | IgG1 | EEQFNSTFR (SEQ ID NO: 10) |
| IgG2 | EEQFNSTFR (SEQ ID NO: 10) | IgG2a/c | EDYNSTIR (SEQ ID NO: 52) |
| IgG3 (major allotype)* | EEQYNSTFR (SEQ ID NO: 2) | IgG2b | EDYNSTLR (SEQ ID NO: 53) |
| IgG4 | EEQFNSTYR (SEQ ID NO: 1) | IgG3 | EAQYNSTFR (SEQ ID NO: 54) |

Figures 12B, 12C:
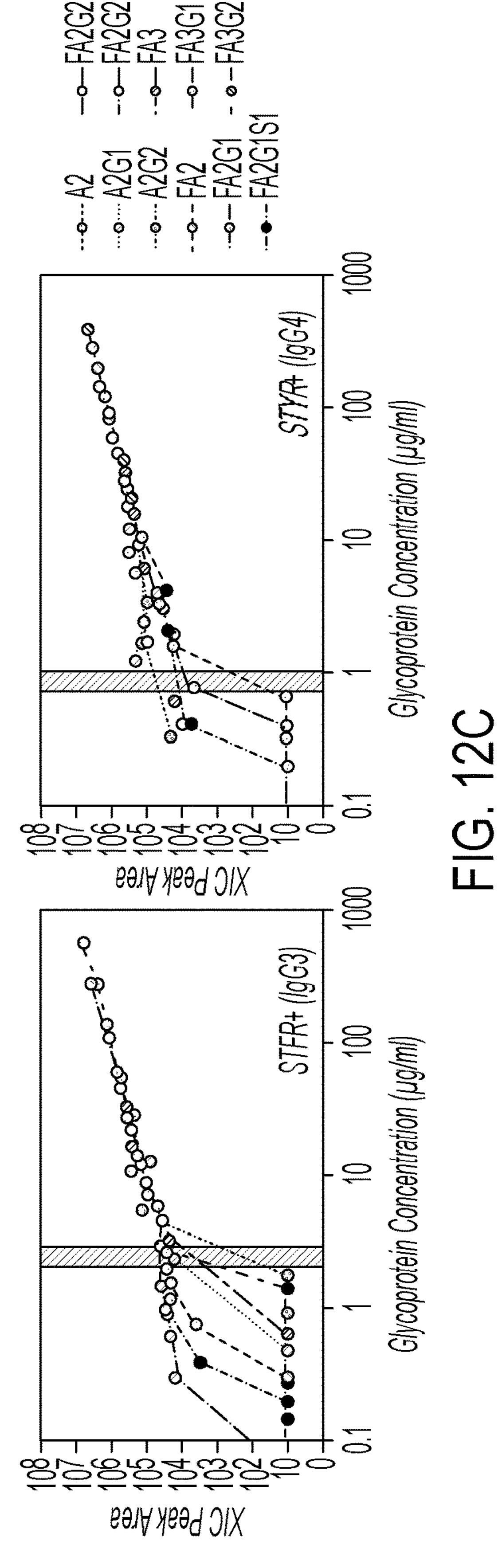
FIG. 12B shows the response curves for individual IgG3 and IgG4 glycoforms at various glycoprotein concentrations in the standard samples prepared in the presence of mouse serum, according to an exemplary embodiment STFR (SEQ ID NO: 5) and STYR (SEQ ID NO: 7).
FIG. 12C shows the response curves for individual IgG3 and IgG4 glycoforms at various glycoprotein concentrations in the standard samples prepared without mouse serum, according to an exemplary embodiment STFR (SEQ ID NO: 5) and STYR (SEQ ID NO: ∂5).
Figure 13A:
FIG. 13A-13G shows N-glycosylation profiles quantified in standard IgG subclass mixtures (IgG1, IgG2, IgG3, and IgG4) with matrix using the extracted ion chromatogram peak area of y4 ions, according to an exemplary embodiment.
Figure 13A:
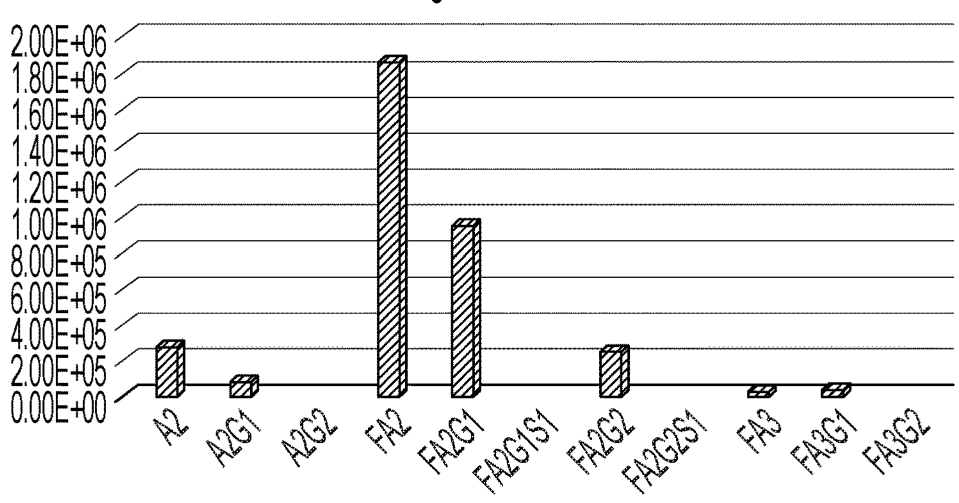
Figure 13A:
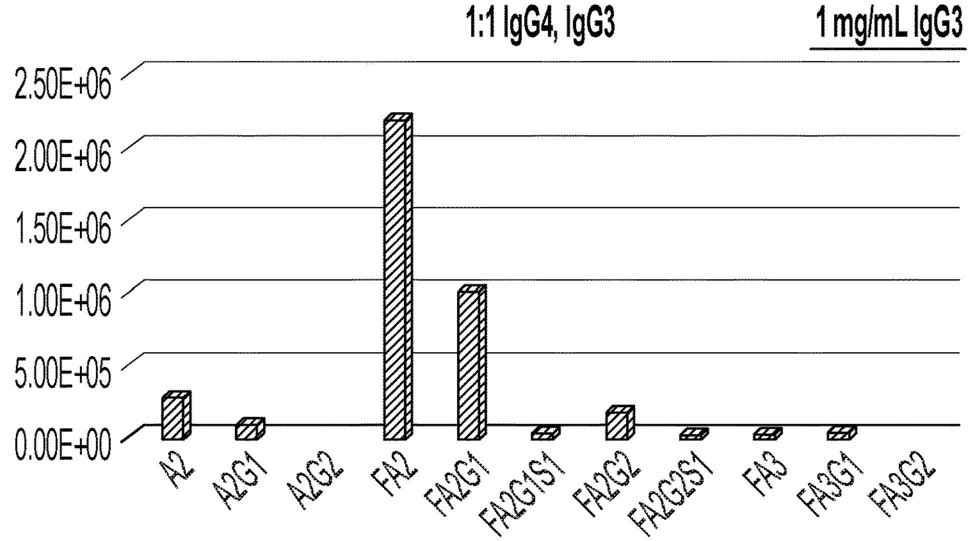
Figure 13A:
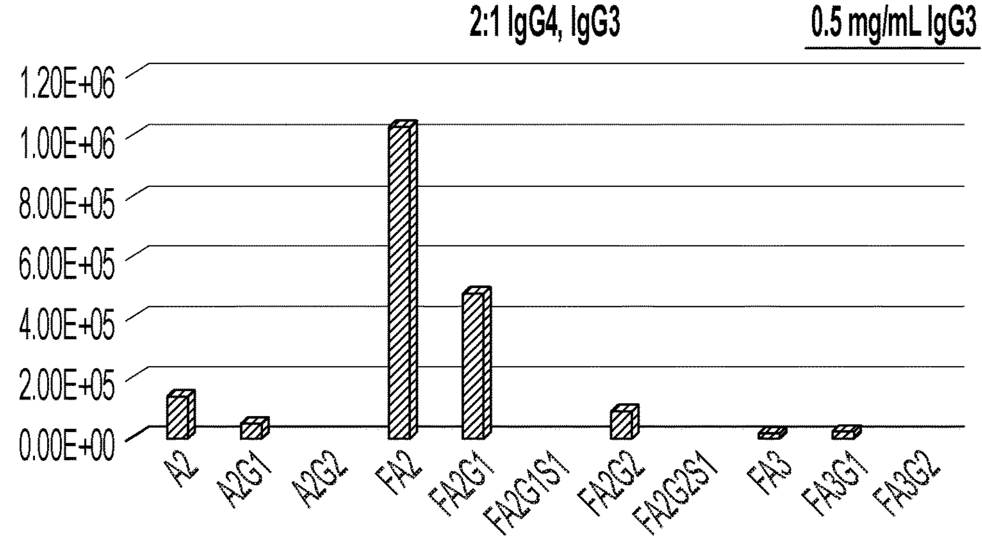
Figure 13B:
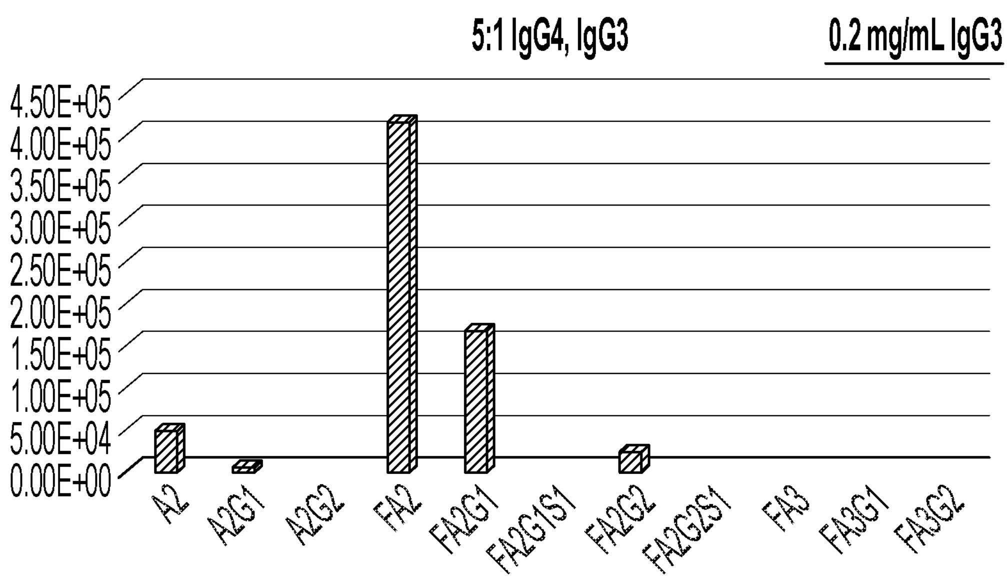
Figure 13B:
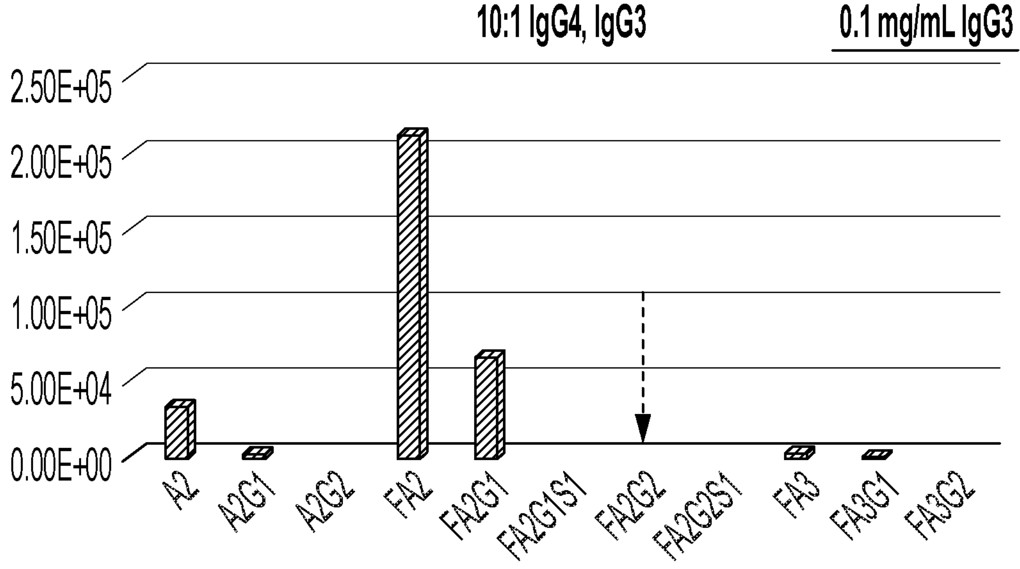
Figure 13C:
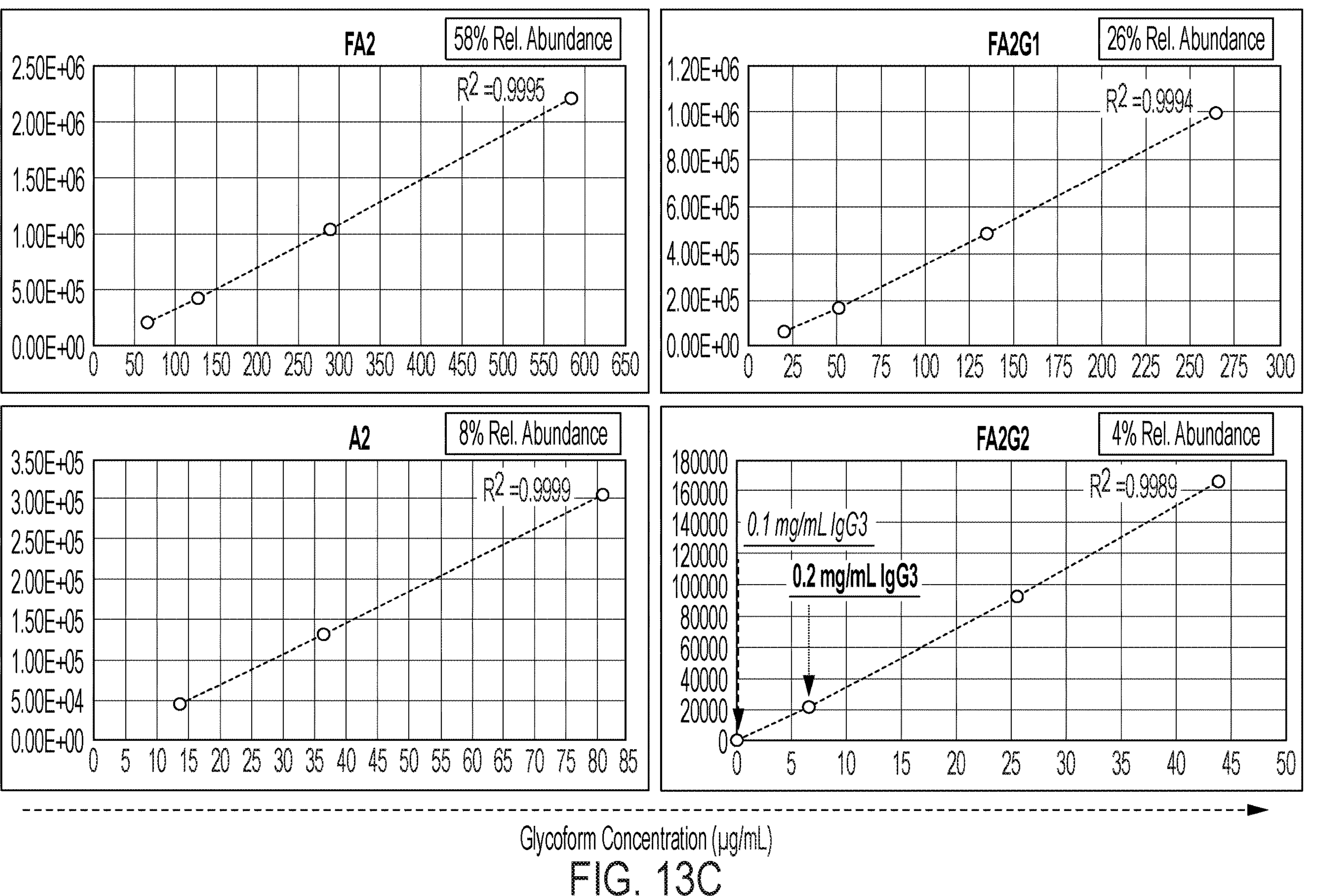
Figure 13D:
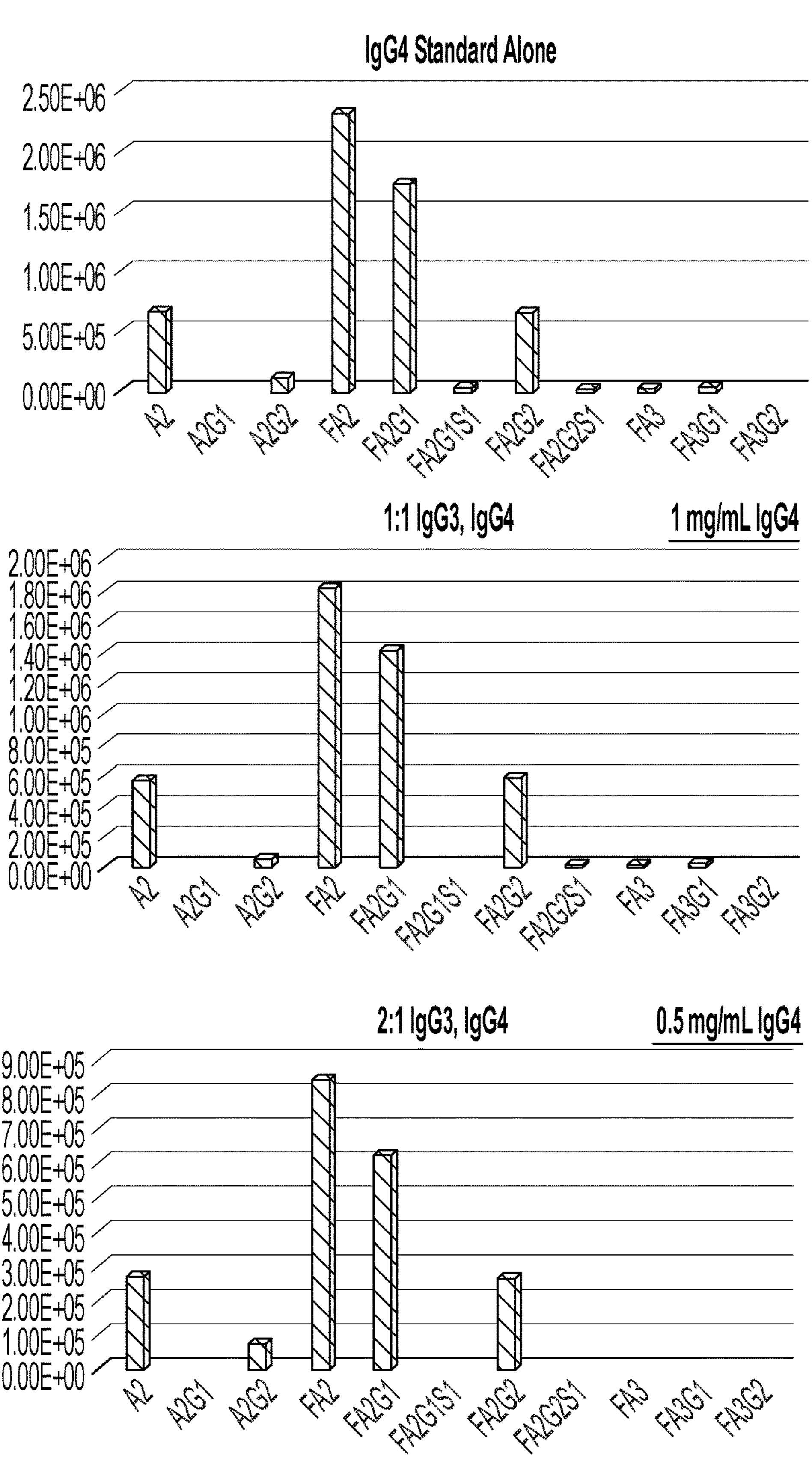
Figure 13E:
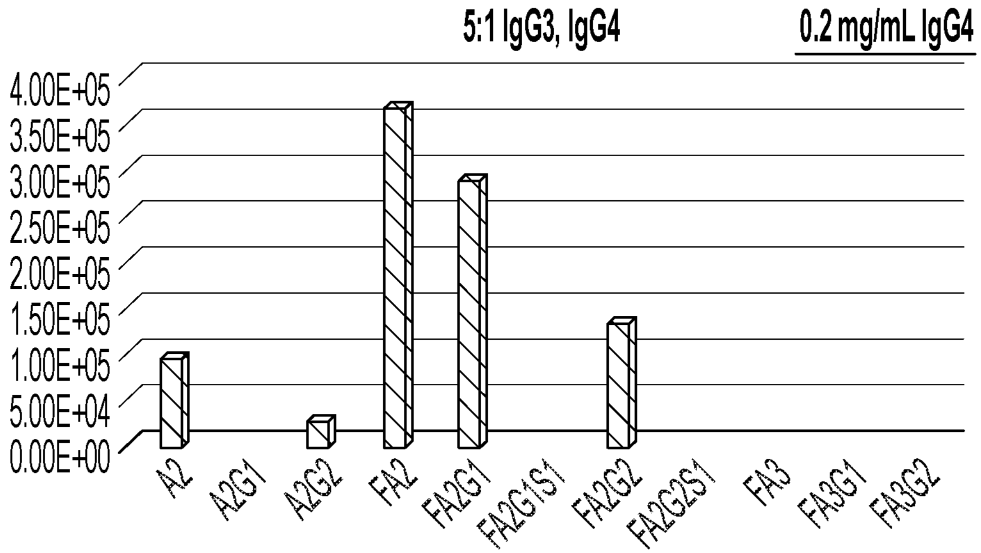
Figure 13E:
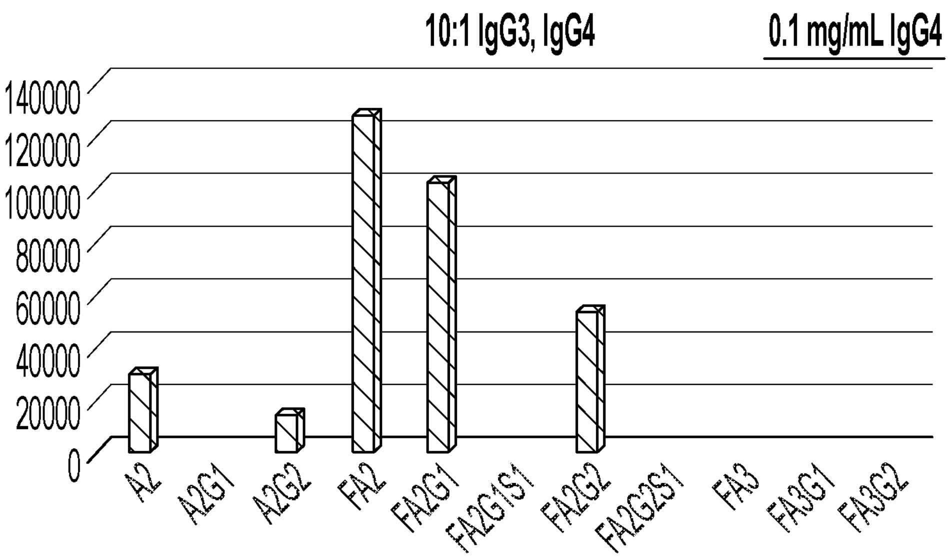
Figure 13F:
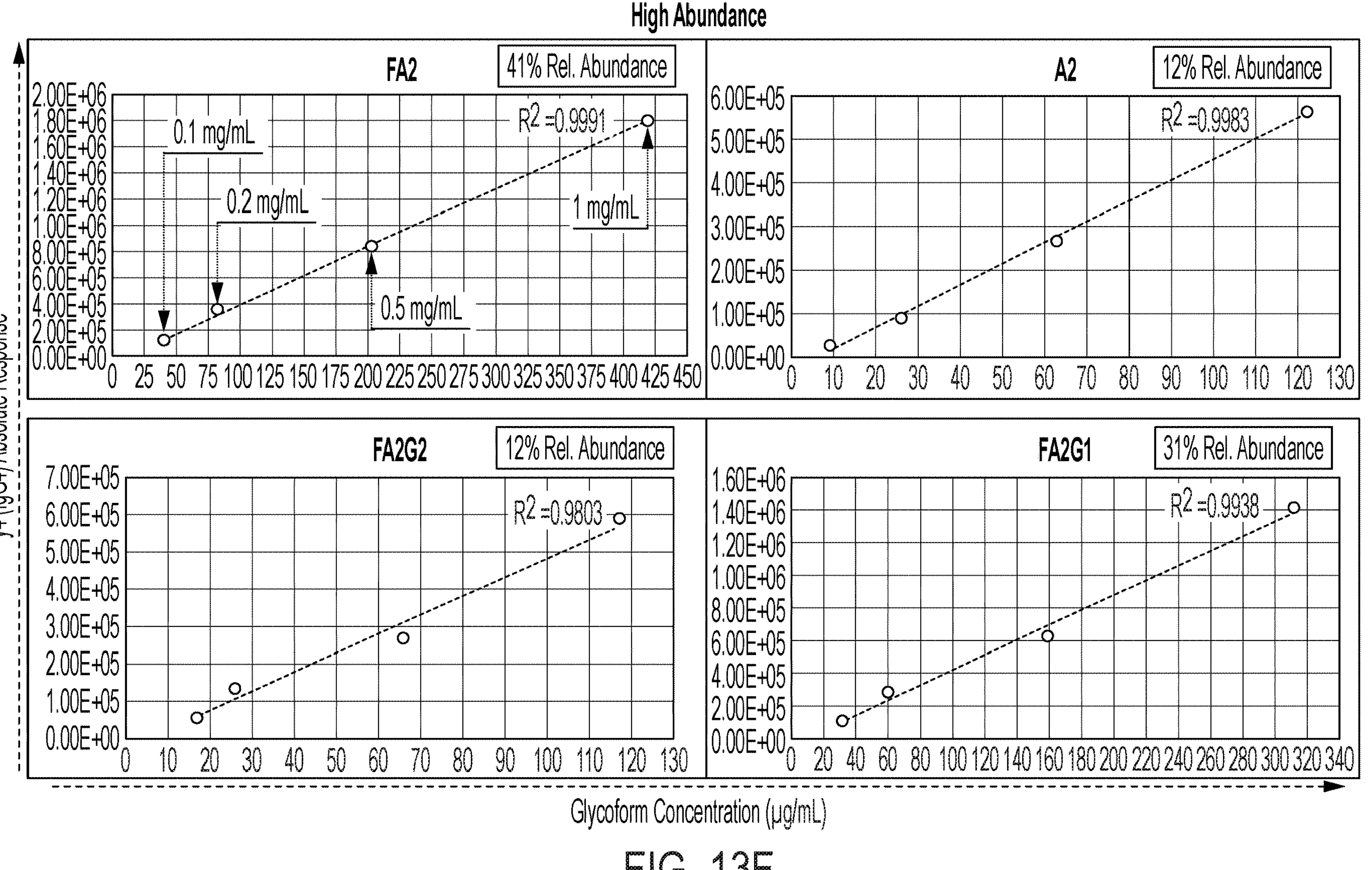
Figure 13G:
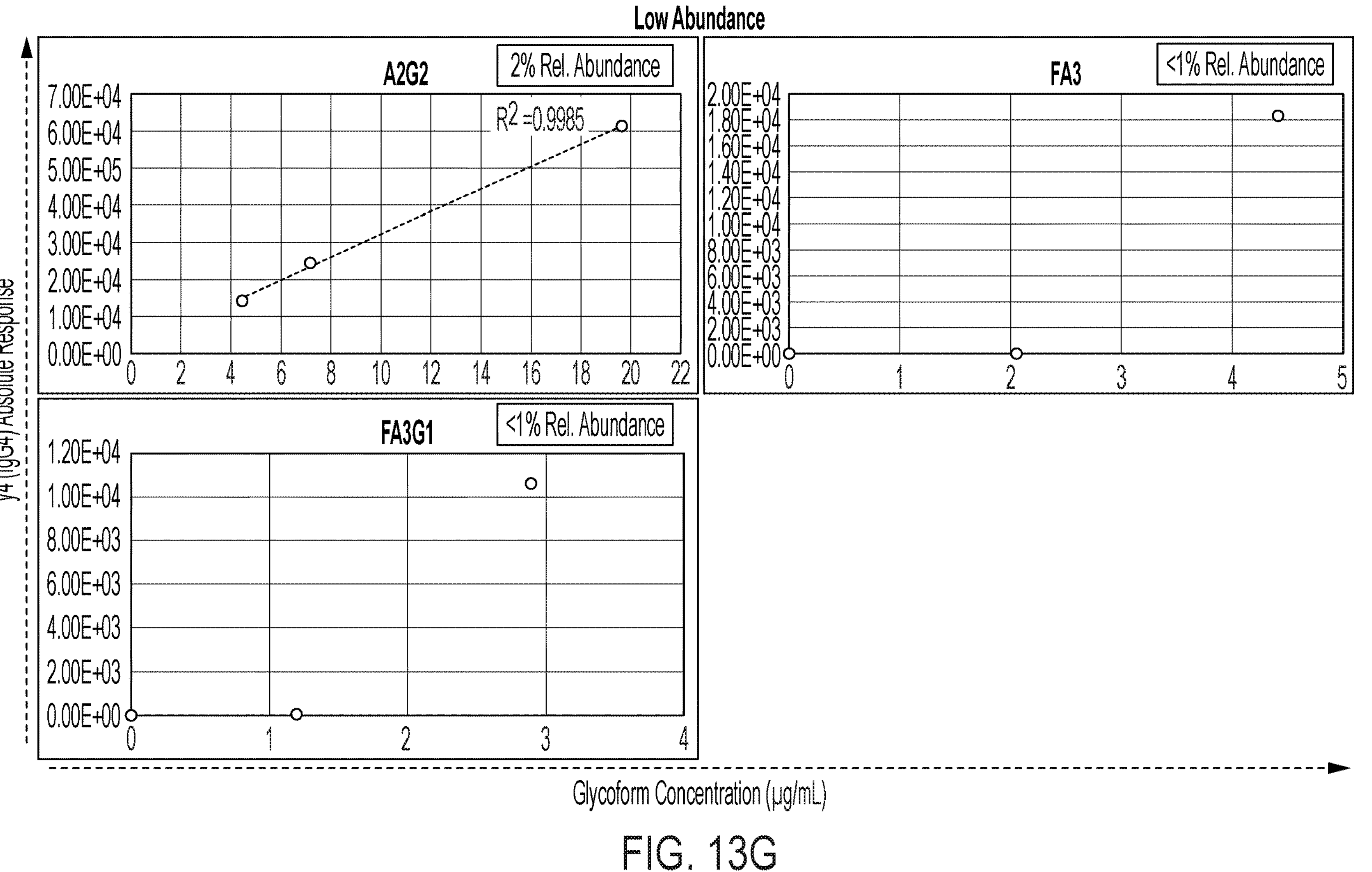
Figure 14A:
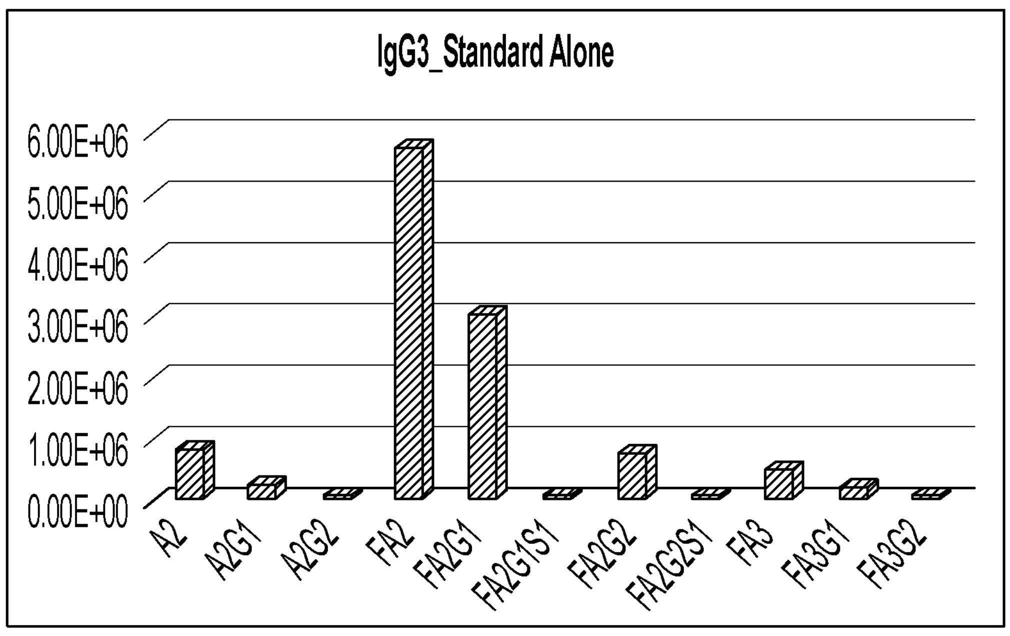
FIG. 14A-14J shows N-glycosylation profiles quantified in standard IgG subclass mixtures (IgG1, IgG2, IgG3, and IgG4) without matrix using the extracted ion chromatogram peak area of y4 ions, according to an exemplary embodiment.
Figure 14A:
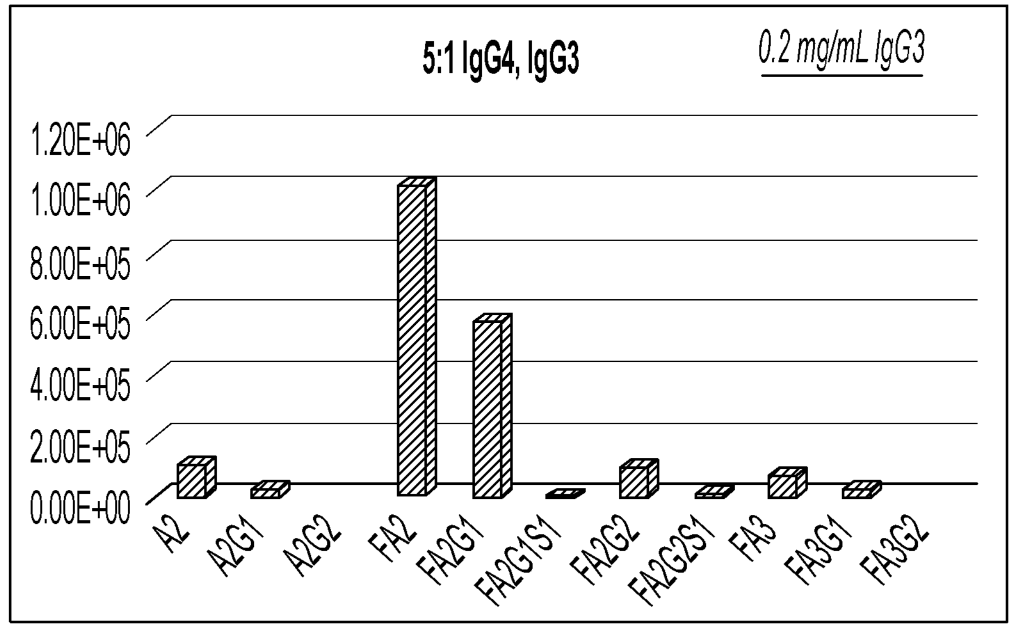
Figure 14B:
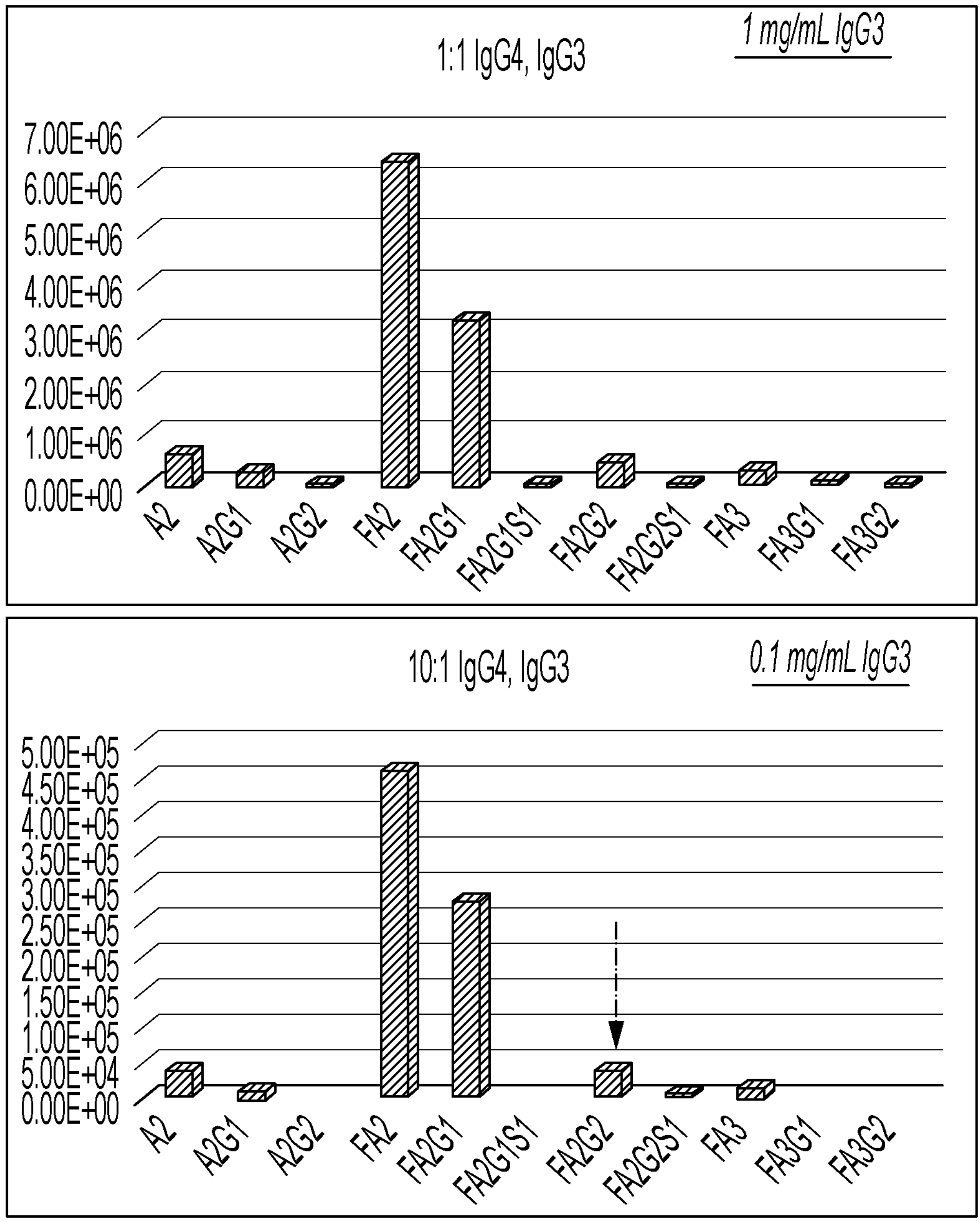
Figure 14C:
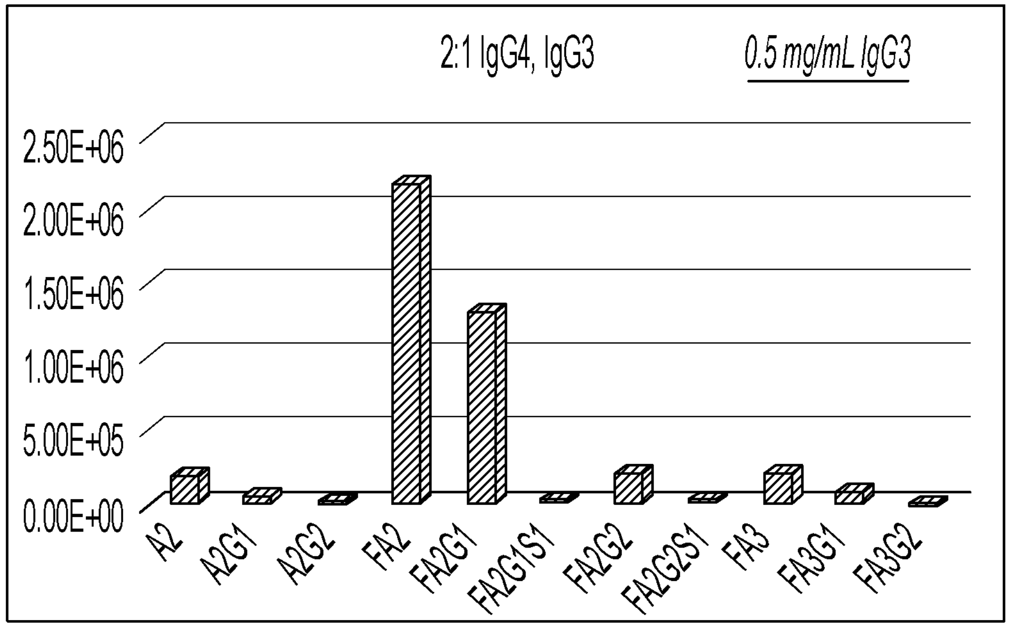
Figure 14C:
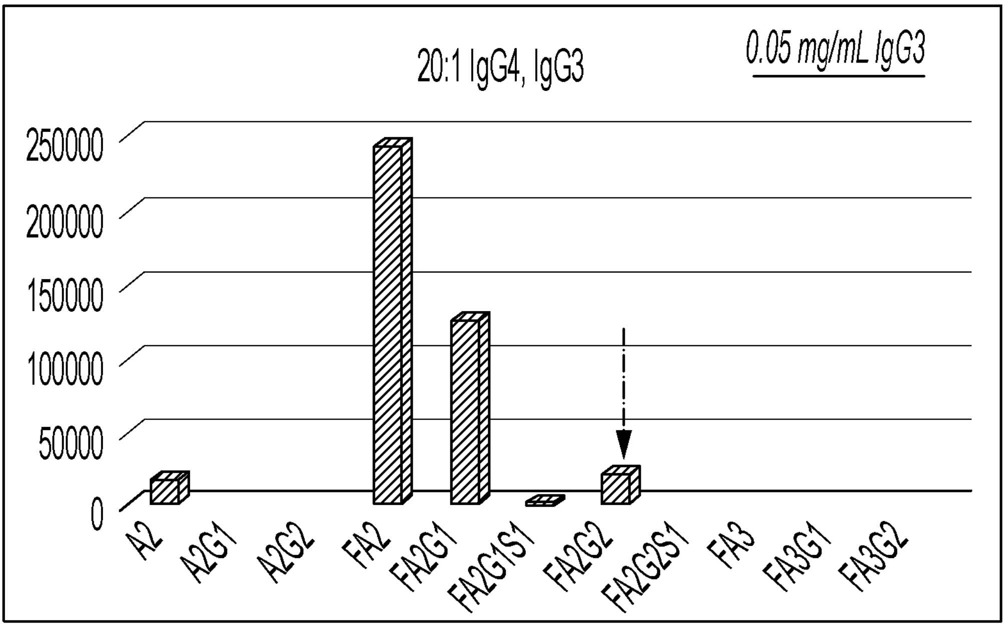
Figure 14D:
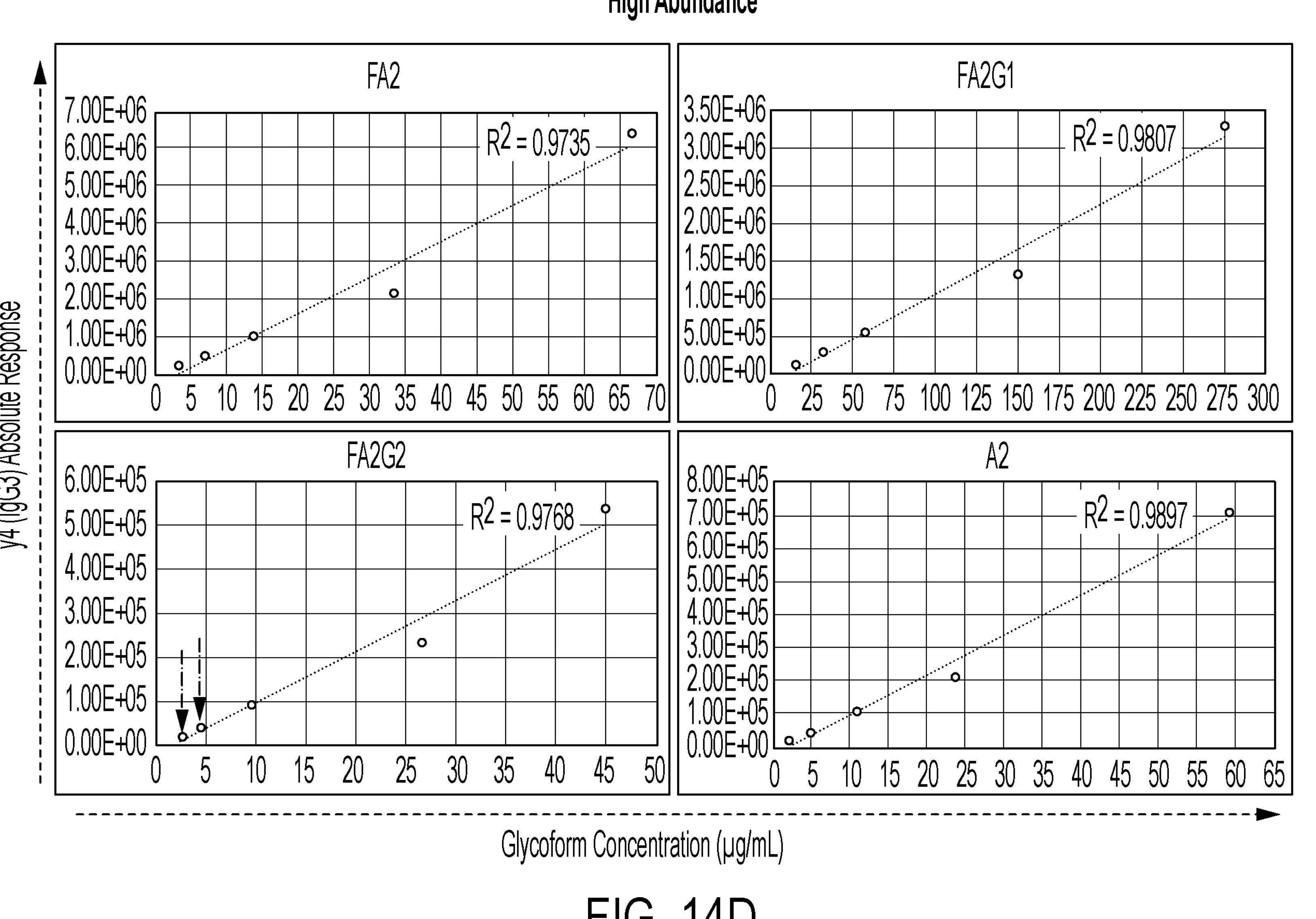
Figure 14E:
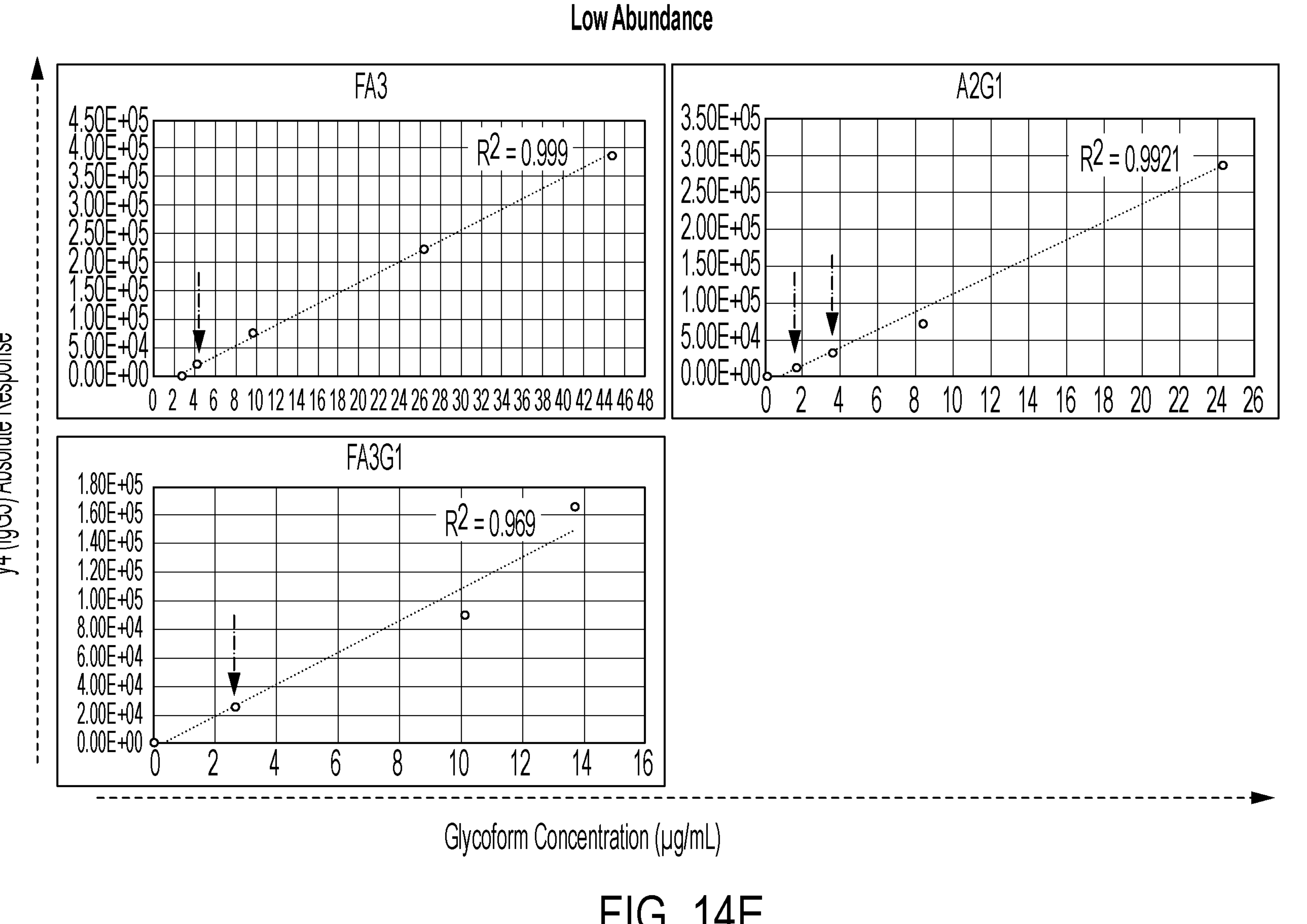
Figure 14F:
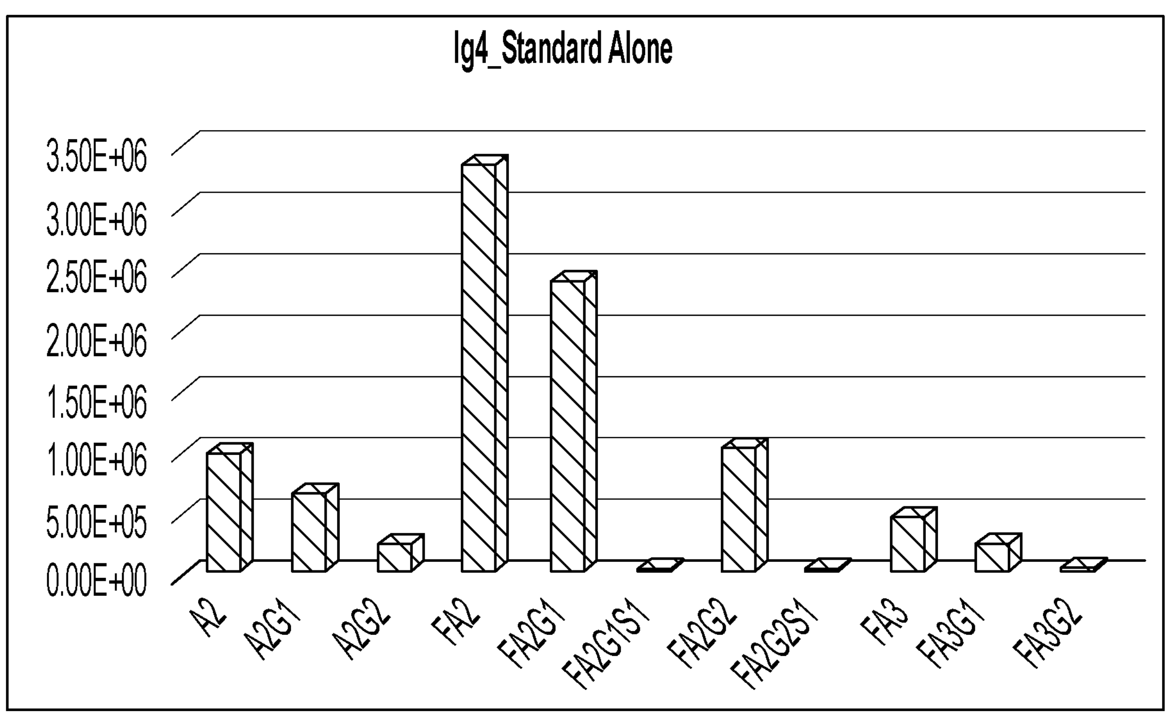
Figure 14F:
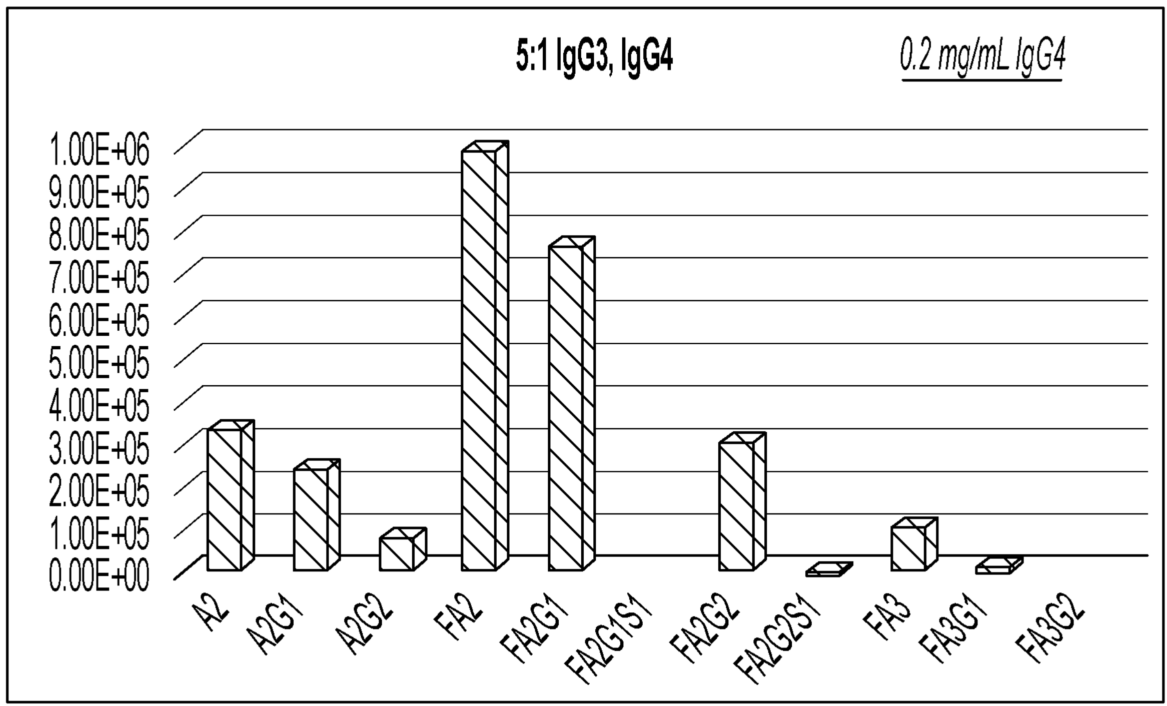
Figure 14G:
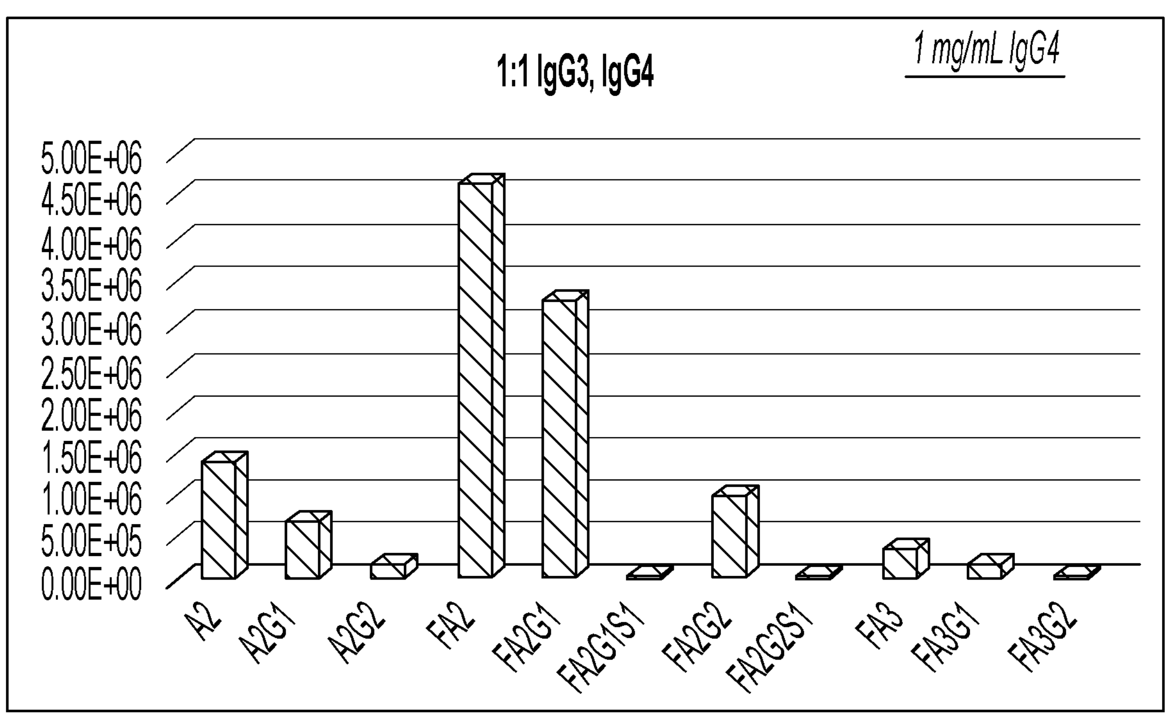
Figure 14G:
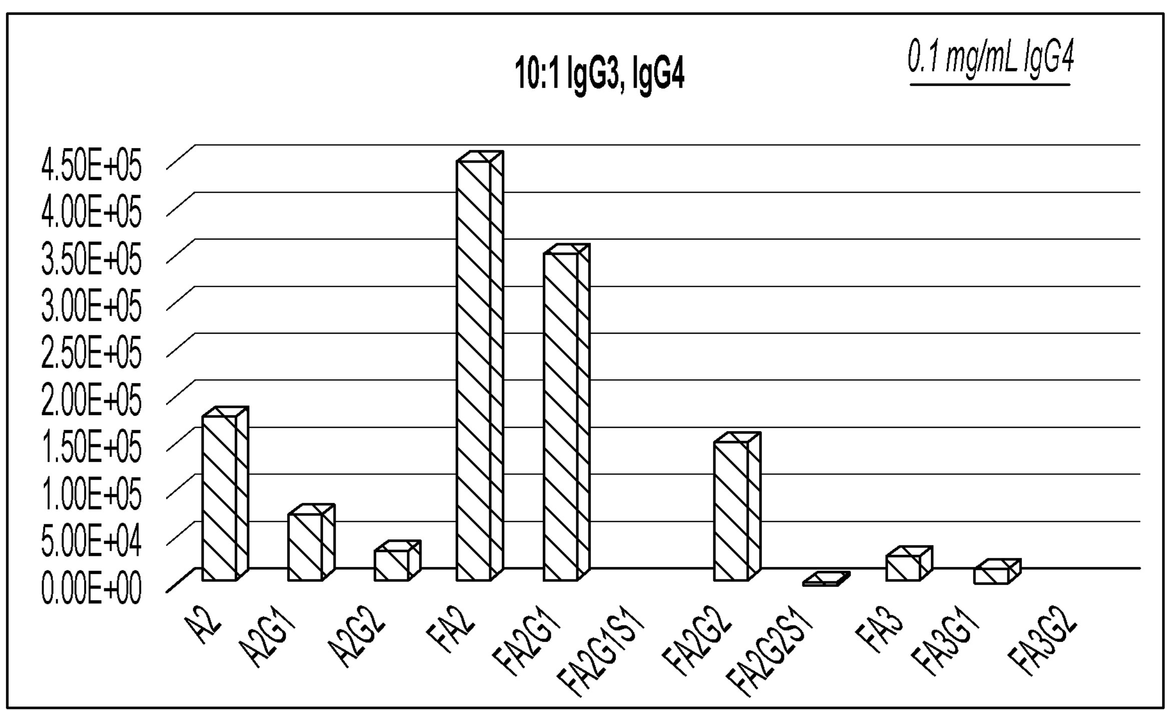
Figure 14H:
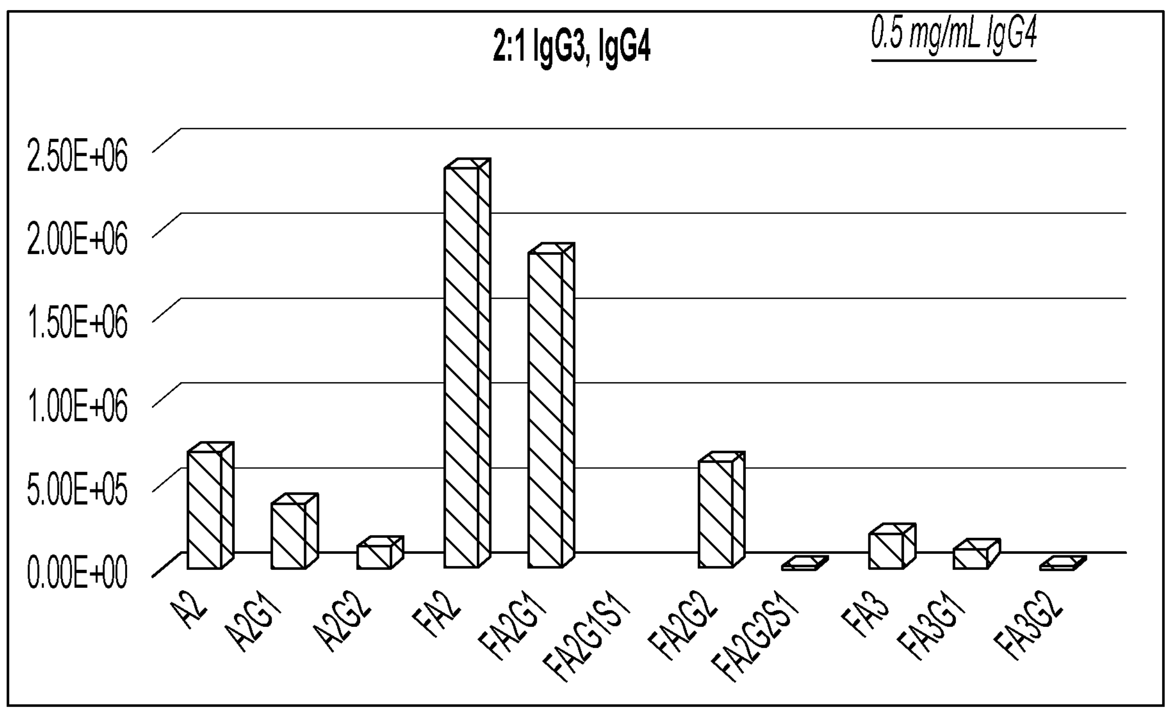
Figure 14H:
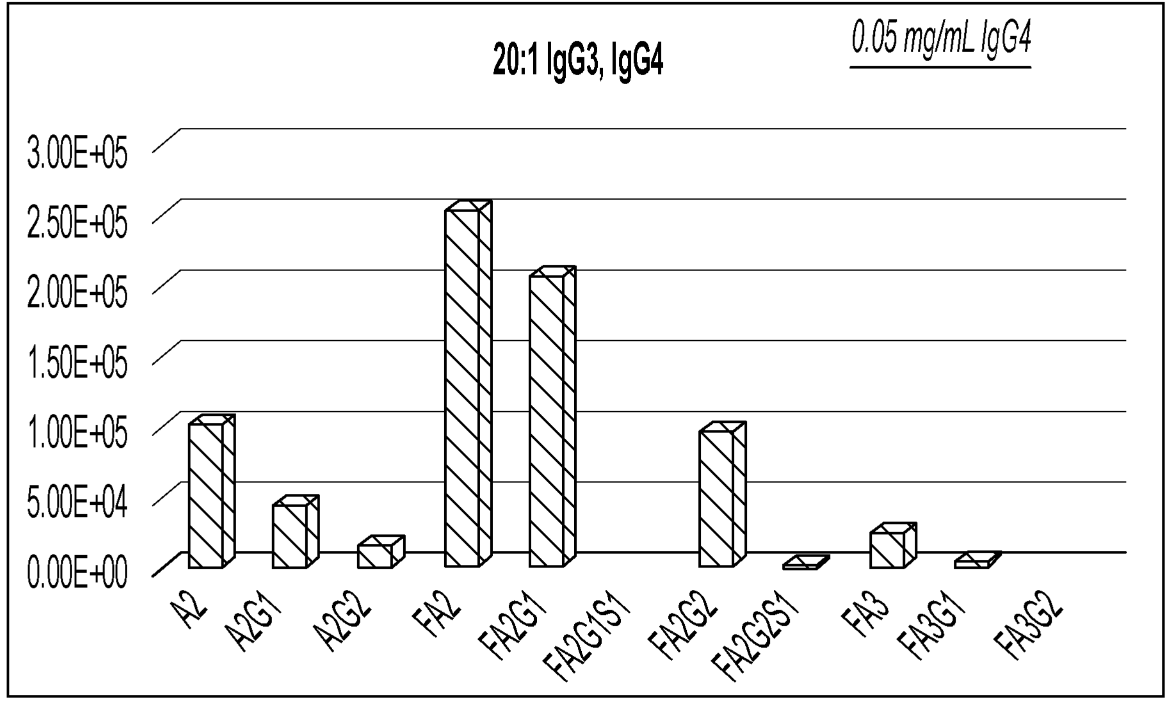
Figure 14I:
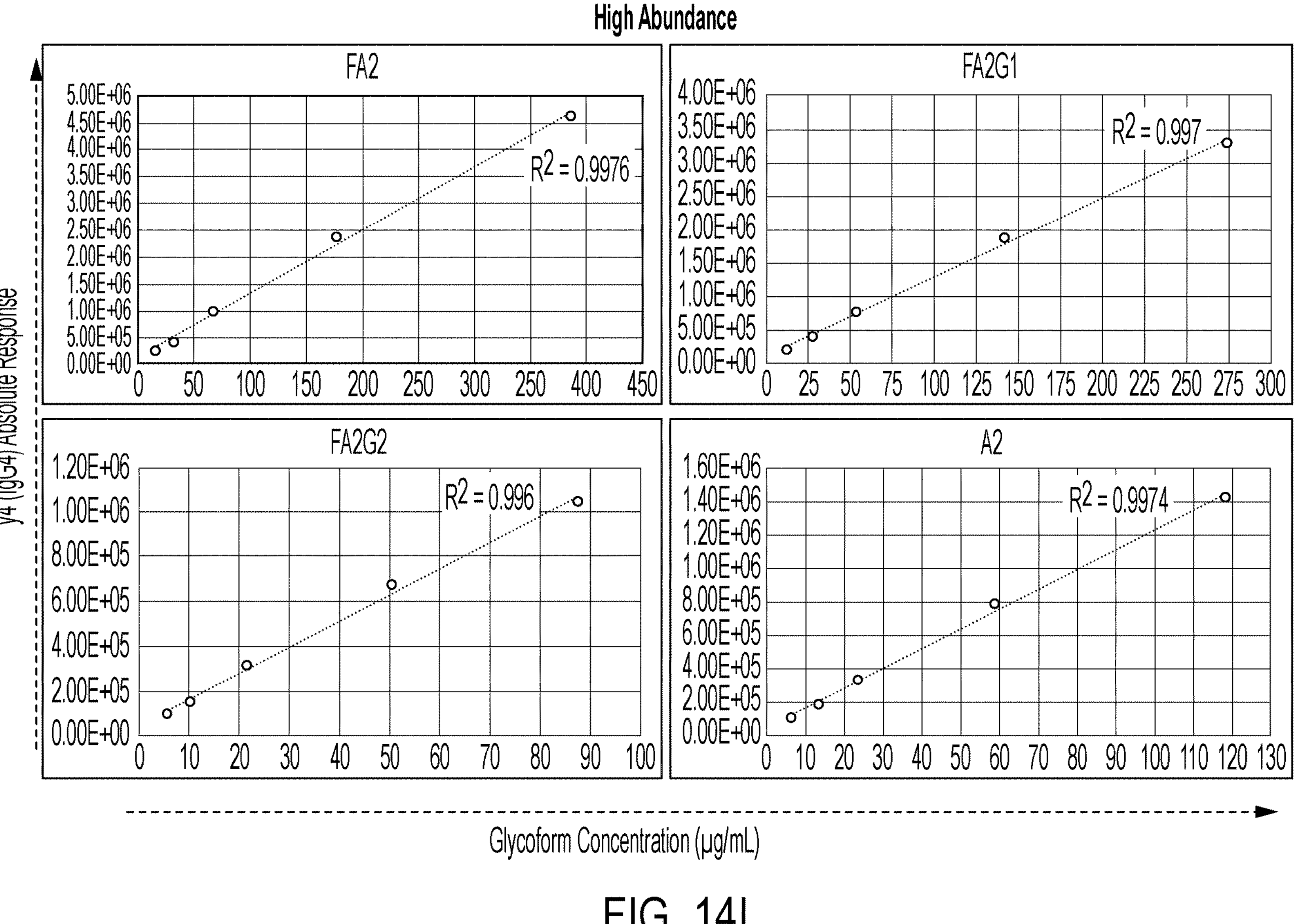
Figure 14J:
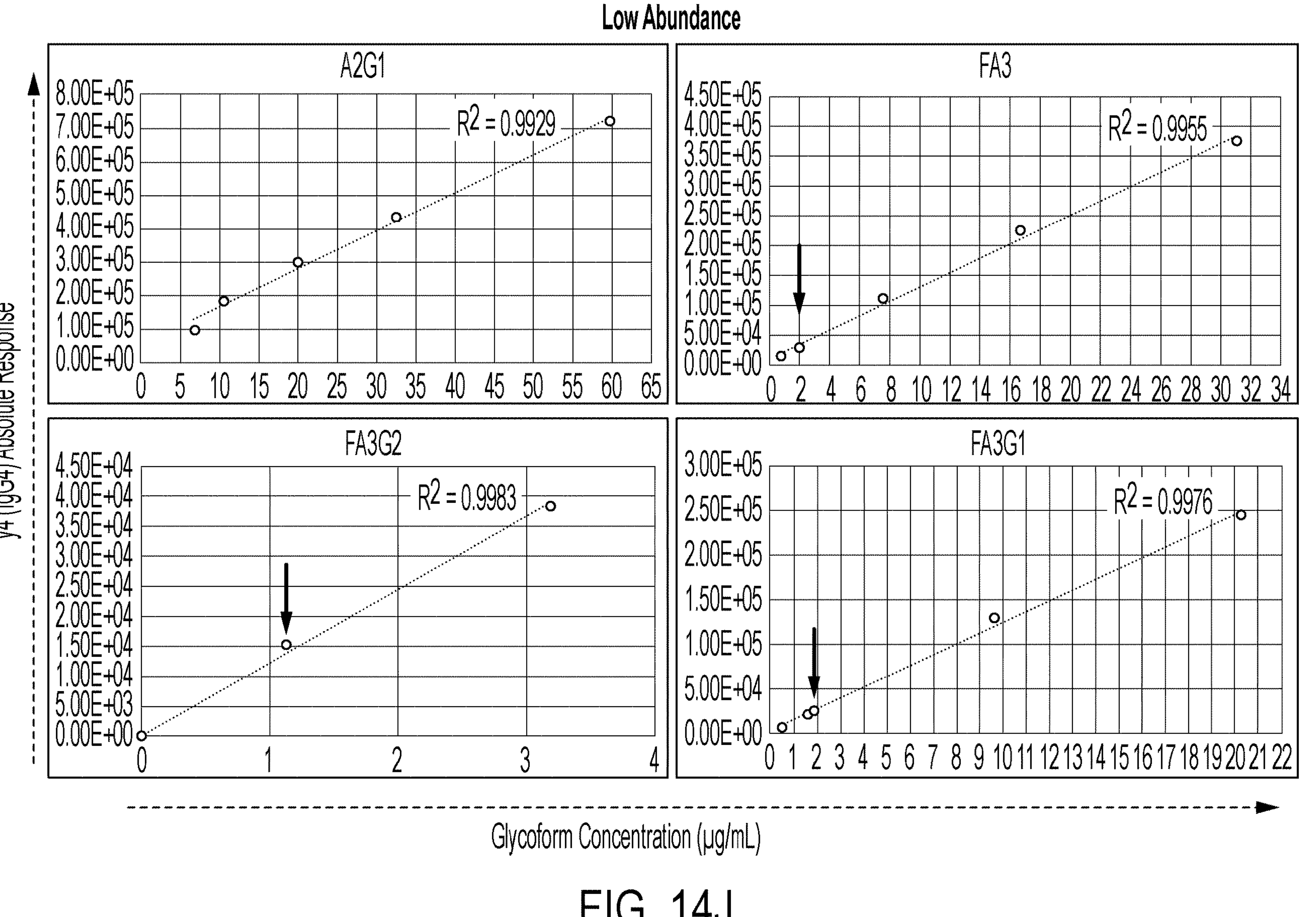

To further evaluate the detection limit for each glycoform from IgG3 and IgG4, FIG. 12B shows the y4 product ion peak area versus the actual protein concentration of each IgG glycoform. The actual protein concentration for a specific glycoform was calculated using the nominal concentration of IgG3 or IgG4 in each mixture sample applied by the percentile level of that glycoform determined in the samples containing IgG3 or IgG4 at their highest concentration (1000 μg/ml). FIG. 12B, FIG. 13A-13G, Table 9 and Table 10 show that the potential detection limit of individual glycoproteoforms can be as low as 10 μg/ml for IgG3 and 5 μg/ml for IgG4. This result also suggested that all the monitored glycoforms cannot always be detected when the concentration of IgG3 or IgG4 was low. For example, FIG. 12B, FIG. 13A-13G and Table 9 show that, if the nominal concentration of total IgG3 was 500 μg/ml, the low occupancy glycoforms with a relative level of less than 2% could not be detected because the corresponding concentration was less than 10 g/ml, below the limit of detection, although the other abundant glycoforms could still be quantified. Therefore, the relative percentage of high abundance glycoforms could have been exaggerated when the IgG protein level was low and glycoforms below the detection limit could not have contributed to the percentage calculation. The aforementioned problem could be solved by establishing absolute quantification using synthetic standard glycopeptides.

TABLE 9

Quantitation of IgG3 Glycoforms in Excess IgG4 Milieu

| Glycopeptide | IgG3 Std. | 1:1 IgG3, IgG4 | 1:2 IgG3, IgG4 | 1:5 IgG3, IgG4 | 1:10 IgG3, IgG4 |
|---|---|---|---|---|---|
| A2 | 7.9% | 8.1% | 7.3% | 6.9% | 12.8% |
| A2G1 | 2.5% | 1.4% | 2.1% | 0.0% | 0.2% |
| FA2 | 54.8% | 58.4% | 57.7% | 64.3% | 66.0% |
| FA2G1 | 26.5% | 26.4% | 26.9% | 25.5% | 20.4% |
| FA2G1S1 | 0.0% | 0.1% | 0.0% | 0.0% | 0.0% |
| FA2G2 | 7.1% | 4.4% | 5.1% | 3.3% | 0.0% |
| FA3 | 0.5% | 0.2% | 0.9% | 0.0% | 0.6% |
| FA3G1 | 0.7% | 0.9% | 0.0% | 0.0% | 0.0% |
| % Fucosylation | 90% | 91% | 91% | 93% | 87% |
| % Galactosylation | 22% | 19% | 20% | 16% | 10% |
| % Sialyation | 0.0% | 0.3% | 0.0% | 0.0% | 0.0% |

TABLE 10

Quantitation of IgG4 Glycoforms in Excess IgG3 Milieu

| Glycopeptide | IgG4 Std. | 1:1 IgG3, IgG4 | 2:1 IgG3, IgG4 | 5:1 IgG3, IgG4 | 10:1 IgG3, IgG4 |
|---|---|---|---|---|---|
| A2 | 12.2% | 12.6% | 13.0% | 10.4% | 9.0% |
| A2G2 | 2.0% | 1.4% | 3.6% | 2.8% | 4.4% |
| FA2 | 41.9% | 40.4% | 40.7% | 40.6% | 39.1% |
| FA2G1 | 31.2% | 31.6% | 30.1% | 31.7% | 31.2% |
| FA2G1S1 | 0.1% | 0.0% | 0.0% | 0.0% | 0.0% |
| FA2G2 | 11.7% | 13.1% | 12.6% | 14.6% | 16.3% |
| FA2G2S1 | 0.2% | 0.3% | 0.0% | 0.0% | 0.0% |
| FA3 | 0.4% | 0.4% | 0.0% | 0.0% | 0.0% |
| FA3G1 | 0.3% | 0.2% | 0.0% | 0.0% | 0.0% |
| % Fucosylation | 86% | 86% | 83% | 87% | 87% |
| % Galactosylation | 30% | 31% | 31% | 33% | 30% |
| % Sialyation | 0.4% | 0.3% | 0.0% | 0.0% | 0.0% |

Detection of glycopeptides in the PRM method could be improved by removing the matrix to reduce ion suppression, as well as the amount co-isolated interfering precursors. This can be performed using affinity-based enrichment with immobilized protein A, immobilized protein G or a combination thereof during sample preparation, which can effectively bind to all IgG subclasses. To evaluate the signal improvement in the ideal case of matrix-free samples, the aforementioned standard IgG mixtures were directly prepared in water and analyzed using the same approach. FIG. 12B shows that the estimated detection limit was significantly improved to about 3 μg/ml for IgG3 and about 1 μg/ml for IgG4. FIG. 14A-14I shows that all major glycoforms were successfully detected without quantitative bias in the sample where the concentration of IgG3 or IgG4 was 50 μg/ml (e.g., about 10 times lower than the samples with matrix) when the co-isolated partner IgG subclass was 1000 μg/ml.

IgG Glycosylation Profiling in Commercial Sera and System Robustness Evaluation

The optimized microflow LC-MnESI-PRM method was first applied to IgG N-glycosylation profiling in two commercial human pooled sera from different vendors. Enrichment of total IgGs was not performed during sample preparation. FIG. 15 shows a summary of IgG subclass-specific N-glycosylation profiles and glycan traits. Quantification using different types of transitions (Y1 and y4) were highly comparable for IgG1 and IgG2. For IgG3 and IgG4, since their Y1 fragments cannot be distinguished by the m/z and retention time, the partition of the total Y1 peak area for IgG3 and IgG4 was determined based on relative peak area of y4 ions (Calculation Scheme I). Calculation of relative levels of individual glycopeptides using Y1 (determined by total Y1 and y4) and y4 alone exhibited highly comparable quantitative profiles in both IgG3 and IgG4; however, Y1 was preferentially used in such cases due to the relatively high production yield.

Figure 15A:
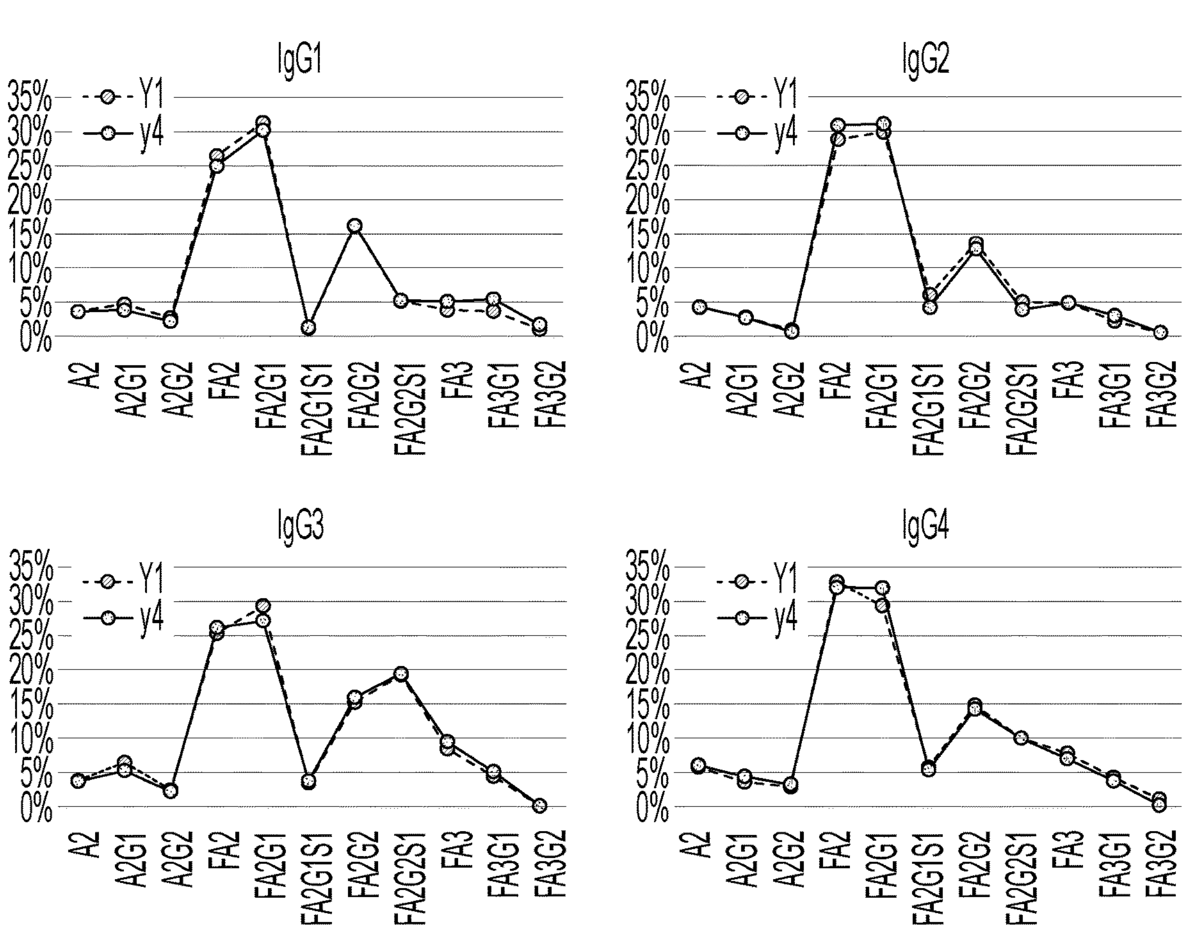
FIG. 15A shows the relative abundance of individual glycoforms of a commercially available human serum from Vendor 1, as determined using the optimized MnESI-PRM method for IgG N-glycosylation profiling, according to an exemplary embodiment. Relative abundance of individual glycoforms was quantified using selected transitions for each IgG subclass, including Y1 and y4. For IgG3 and IgG4, the partition of Y1 was determined based on the y4 ratio.
Figure 15B:
FIG. 15B shows the relative abundance of individual glycoforms of a commercially available human serum from Vendor 2, as determined using the optimized MnESI-PRM method for IgG N-glycosylation profiling, according to an exemplary embodiment. Relative abundance of individual glycoforms was quantified using selected transitions for each IgG subclass, including Y1 and y4. For IgG3 and IgG4, the partition of Y1 was determined based on the y4 ratio.
Figure 15B:
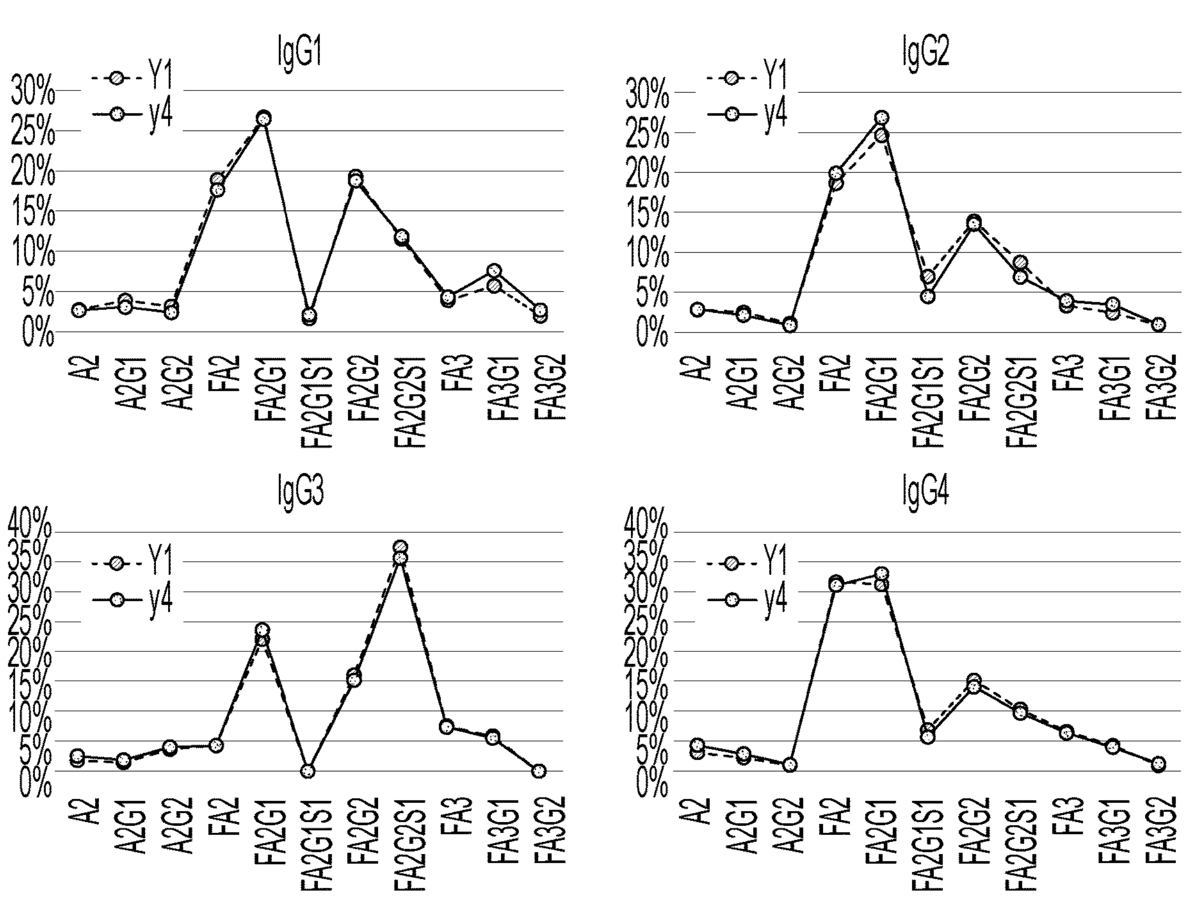

FIG. 15A and Tables 11-14 show that, except for a slightly higher level of FA2G2S1 in IgG3 (15%) compared to the level in other IgGs (5-10%), the overall IgG N-glycosylation profiles were similar across all four IgG subclasses in the serum from Vendor 1. FIG. 15B and Tables 15-18 show that the unique N-glycosylation profile of IgG3 was also present in the serum from Vendor 2, in which the relative level of FA2G2S1 was further enhanced (35%) and meanwhile a significantly decreased FA2 (5%) was also observed compared to other IgG subclasses (20%-25%) and IgG3 in Vendor 1 (20%). To better represent the difference in N-glycosylation profiles in different IgG subclasses, several glycan traits were calculated according to the peak area of individual glycoforms (Calculation Scheme II).

Figure 15C:
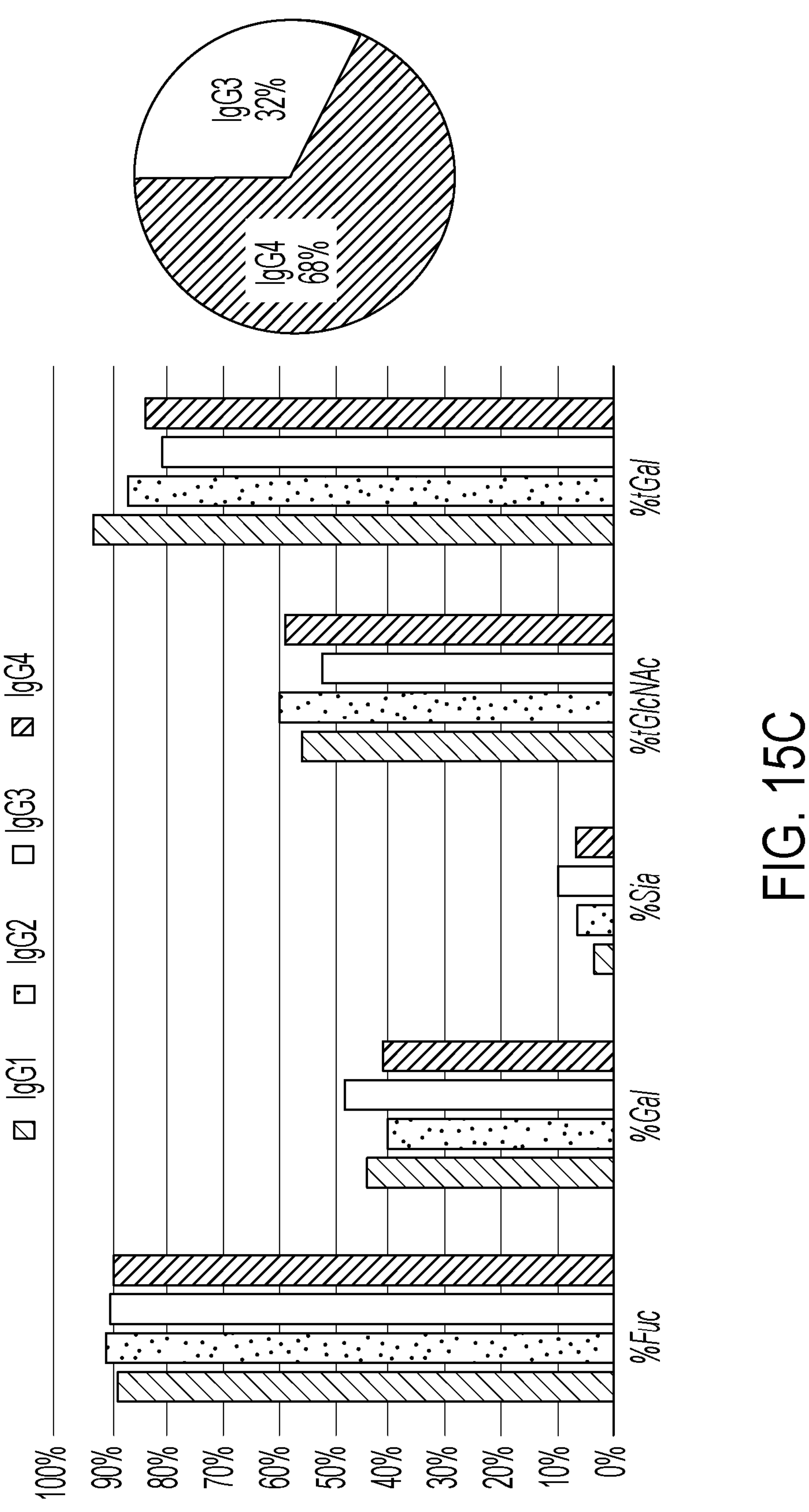
FIG. 15C shows the glycan traits calculated according to the relative abundance of individual glycoforms for Vendor 1, according to an exemplary embodiment.
Figure 15D:
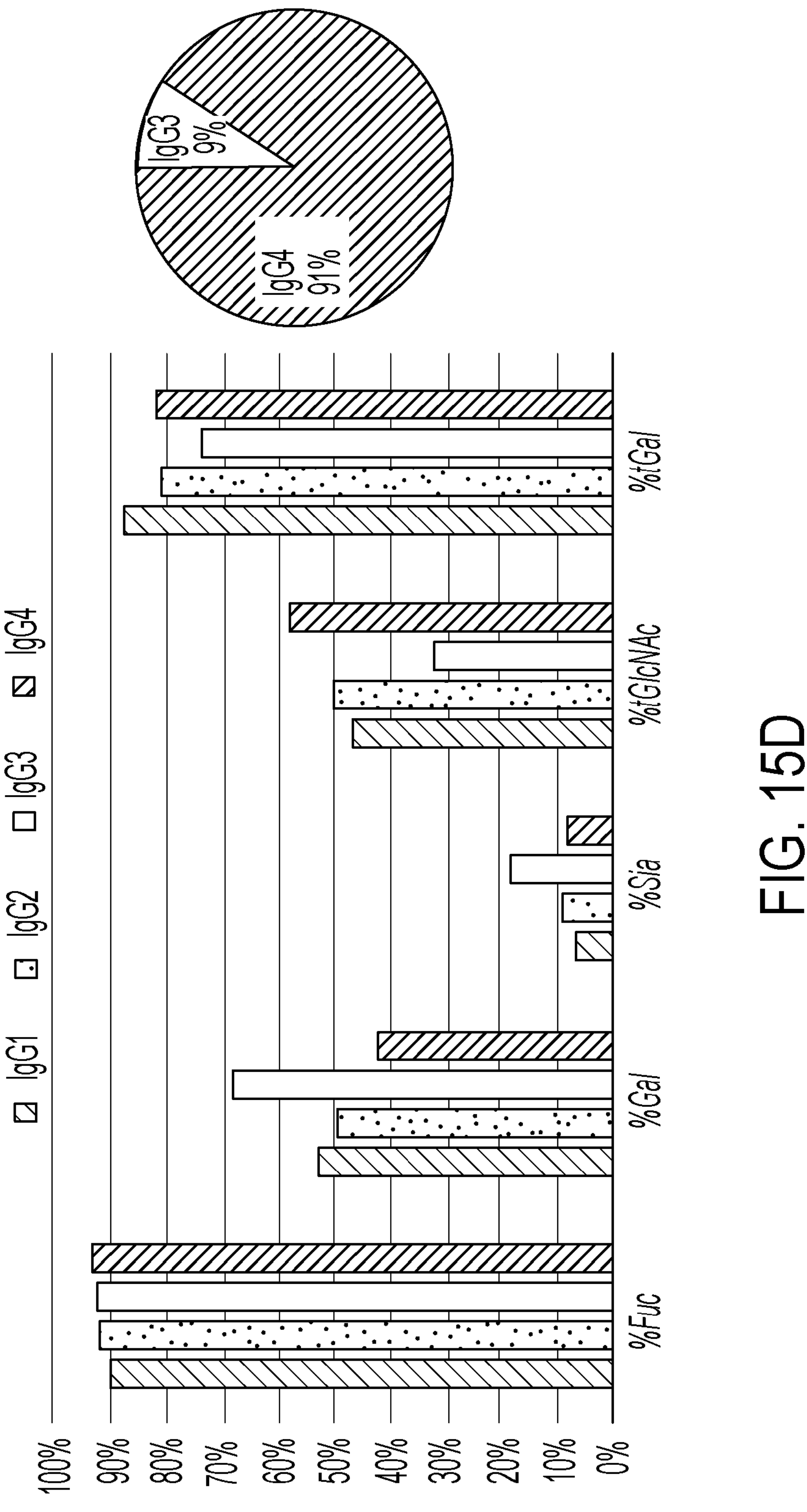
FIG. 15D shows the glycan traits calculated according to the relative abundance of individual glycoforms for Vendor 2, according to an exemplary embodiment.

FIG. 15C and FIG. 15D show that, except for the level of fucosylation (% Fuc), which was highly consistent in all IgGs, all other glycan traits exhibited variation in different IgG subclasses, and their trends are consistent in serum from either Vendor 1 or Vendor 2. The increased FA2G2S1 and decreased FA2 in IgG3 contributed to the highest level of galacosylation (% Gal) and sialyation (% Sia) among all subclasses, especially in serum from Vendor 2. The degree of alteration for the IgG3 N-glycosylation profile could be correlated with the protein concentration of IgG3, which was estimated using the sum of peak area of all monitored glycoforms. FIG. 15C shows that, in serum from Vendor 1, IgG3 was 32% of the total IgG3 and IgG4 mixture, whereas FIG. 15D shows that, in serum from Vendor 2, IgG3 was 9% of the total IgG3 and IgG4 mixture. FIG. 15D also shows that the levels of terminal galactose (% tGal) and terminal N-acetylglucosamine (% tGlcNAc) in IgG3 were 8.7% and 25.5% lower than IgG4 in Vendor 2 serum. FIG. 15C shows that the same trend was also observed in Vendor 1 serum, albeit to a lesser extent. The concentrations of IgG1, IgG2 and IgG4 in both Vendor 1 and Vendor 2 serum were comparable. These data demonstrate that the aforementioned methods have sufficient sensitivity to distinguish levels of IgG3 from other IgG subclasses.

TABLE 11

| Relative Abundance of IgG1 Glycopeptides for Serum from Vendor 1 (Normal Human Serum) | | |
|---|---|---|
| | Y1, y4 | y4 |
| % Fucosylation | 89.0% | 90.4% |
| % Galactosylation | 43.0% | 43.2% |
| % Sialyation | 6.4% | 6.6% |

TABLE 12

| Relative Abundance of IgG2 Glycopeptides for Serum from Vendor 1 (Normal Human Serum) | | |
|---|---|---|
| | Y1, y4 | y4 |
| % Fucosylation | 91.7% | 92.0% |
| % Galactosylation | 38.6% | 37.0% |
| % Sialyation | 11.3% | 8.4% |

TABLE 13

| Relative Abundance of IgG3 Glycopeptides for Serum from Vendor 1 (Normal Human Serum) | | |
|---|---|---|
| | Y1, y4 | y4 |
| % Fucosylation | 89.5% | 90.8% |
| % Galactosylation | 41.5% | 41.0% |
| % Sialyation | 19.2% | 19.6% |

TABLE 14

| Relative Abundance of IgG4 Glycopeptides for Serum from Vendor 1 (Normal Human Serum) | | |
|---|---|---|
| | Y1, y4 | y4 |
| % Fucosylation | 89.8% | 88.6% |
| % Galactosylation | 38.2% | 38.3% |
| % Sialyation | 13.3% | 13.0% |

TABLE 15

| Relative Abundance of IgG1 Glycopeptides for Serum from Vendor 2 (Pooled Human Complement Serum) | | |
|---|---|---|
| | Y1, y4 | y4 |
| % Fucosylation | 90.2% | 91.9% |
| % Galactosylation | 49.5% | 49.6% |
| % Sialyation | 13.3% | 14.0% |

TABLE 16

| Relative Abundance of IgG2 Glycopeptides for Serum from Vendor 2 (Pooled Human Complement Serum) | | |
|---|---|---|
| | Y1, y4 | y4 |
| % Fucosylation | 92.5% | 93.1% |
| % Galactosylation | 44.8% | 43.4% |
| % Sialyation | 18.3% | 13.3% |

TABLE 17

| Relative Abundance of IgG3 Glycopeptides for Serum from Vendor 2 (Pooled Human Complement Serum) | | |
|---|---|---|
| | Y1, y4 | y4 |
| % Fucosylation | 93.1% | 91.6% |
| % Galactosylation | 71.7% | 70.3% |
| % Sialyation | 37.4% | 35.6% |

TABLE 18

| Relative Abundance of IgG4 Glycopeptides for Serum from Vendor 2 (Pooled Human Complement Serum) | | |
|---|---|---|
| | Y1, y4 | y4 |
| % Fucosylation | 94.3% | 92.6% |
| % Galactosylation | 43.9% | 43.2% |
| % Sialyation | 15.2% | 13.6% |

Figure 16A:
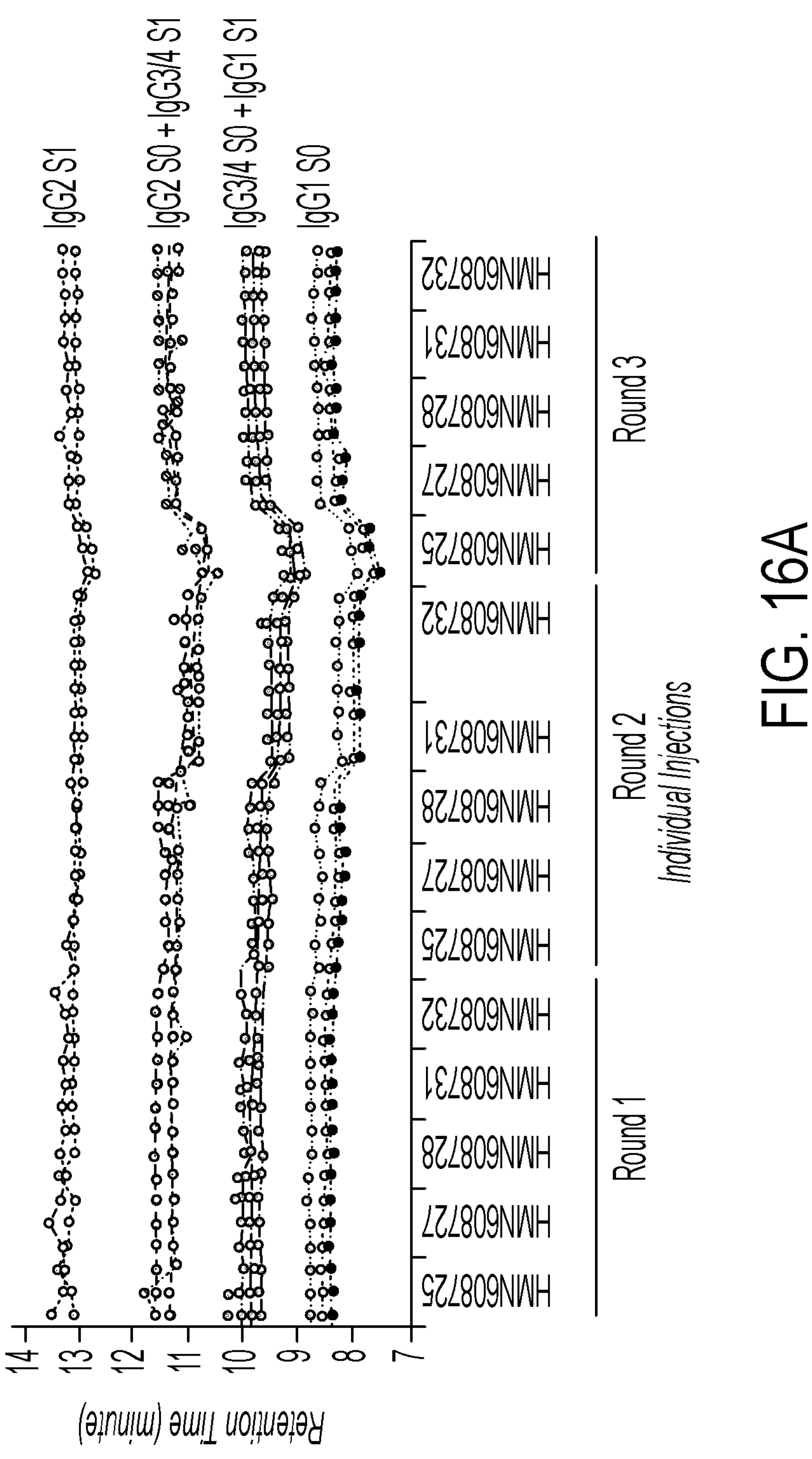
FIG. 16A shows the retention time for detected peaks of individual glycopeptides from four IgG phenotypes that were monitored across different injections, according to an exemplary embodiment. Each line indicates one glycopeptide.

IgG N-glycosylation profiling was also performed for five individual human sera using the same microflow LC-MnESI-PRM-based method (without total IgG enrichment). Assay precision was first evaluated by continuously injecting each digested serum multiple times (at least 3 times) followed by repeating the entire sample list for another two rounds. At least a 12-hour interval where no data injection and acquisition happened was set between the end of one round and the beginning of next round for evaluating day-to-day variation of the system. FIG. 16A shows that the monitored glycopeptides from all four IgG subclasses exhibited modest retention time shifts (less than 1-minute) across all samples and injections, which demonstrated that a stable peak retention time was achieved using microflow LC. Therefore, the 1.7-minute time window in the inclusion list (Table 7) was suitable for a long-term data acquisition requiring less frequent adjustment of RT schedule. The major retention time shift observed after a system idle time (e.g., between round 2 and round 3) could be avoided by continuously acquiring a dataset without a pause between rounds.

Figure 16B:
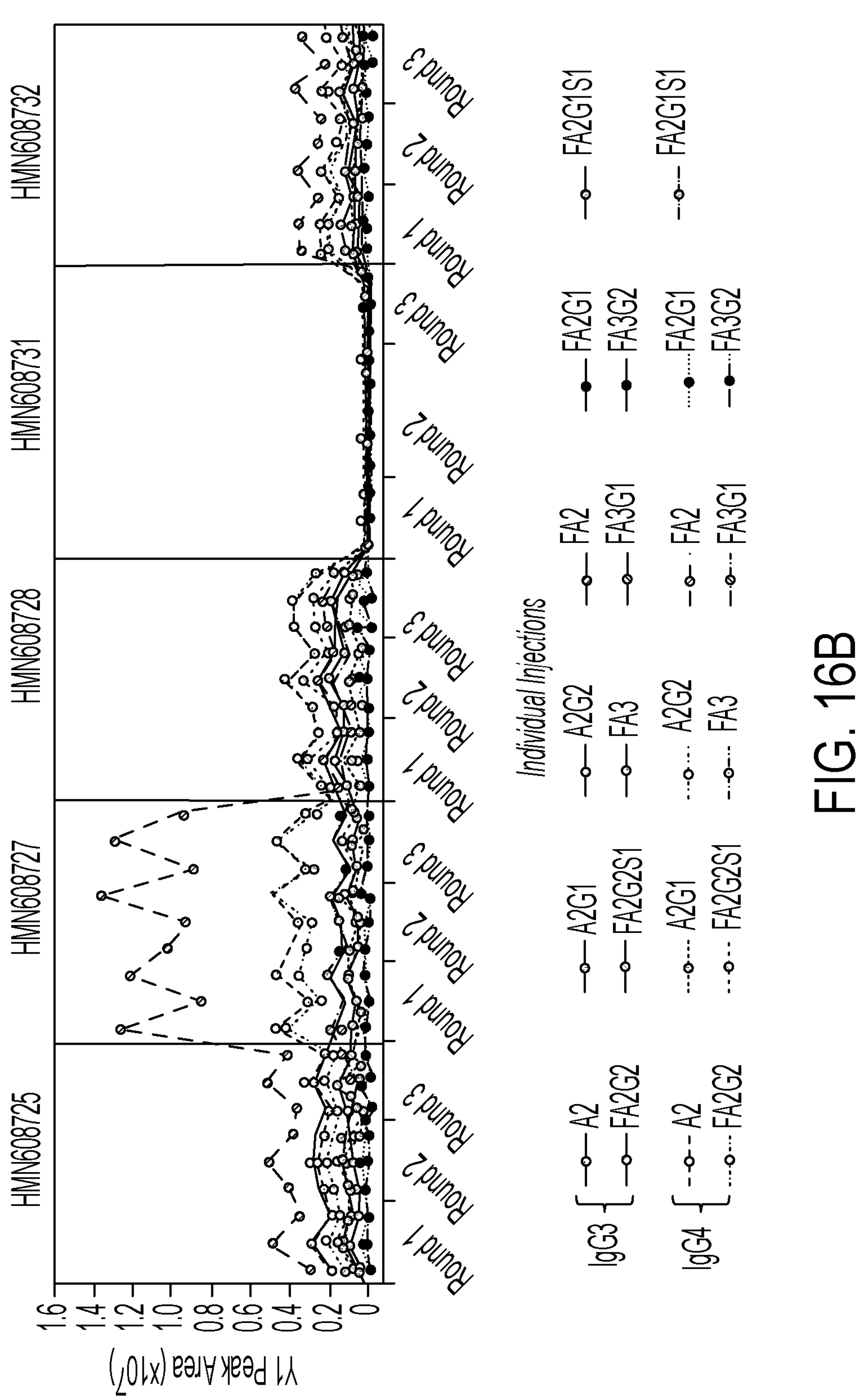
FIG. 16B shows the absolute peak area of Y1 detected for individual glycopeptides from IgG3 and IgG4 (determined by Calculation Scheme I) that were monitored across different injections for each serum, according to an exemplary embodiment. Each line represents one glycopeptide from IgG3 (solid lines) and IgG4 (dash lines). The identical glycoforms from IgG3 and IgG4 are shown in the same color, indicated at the bottom of the panel.
Figure 17:
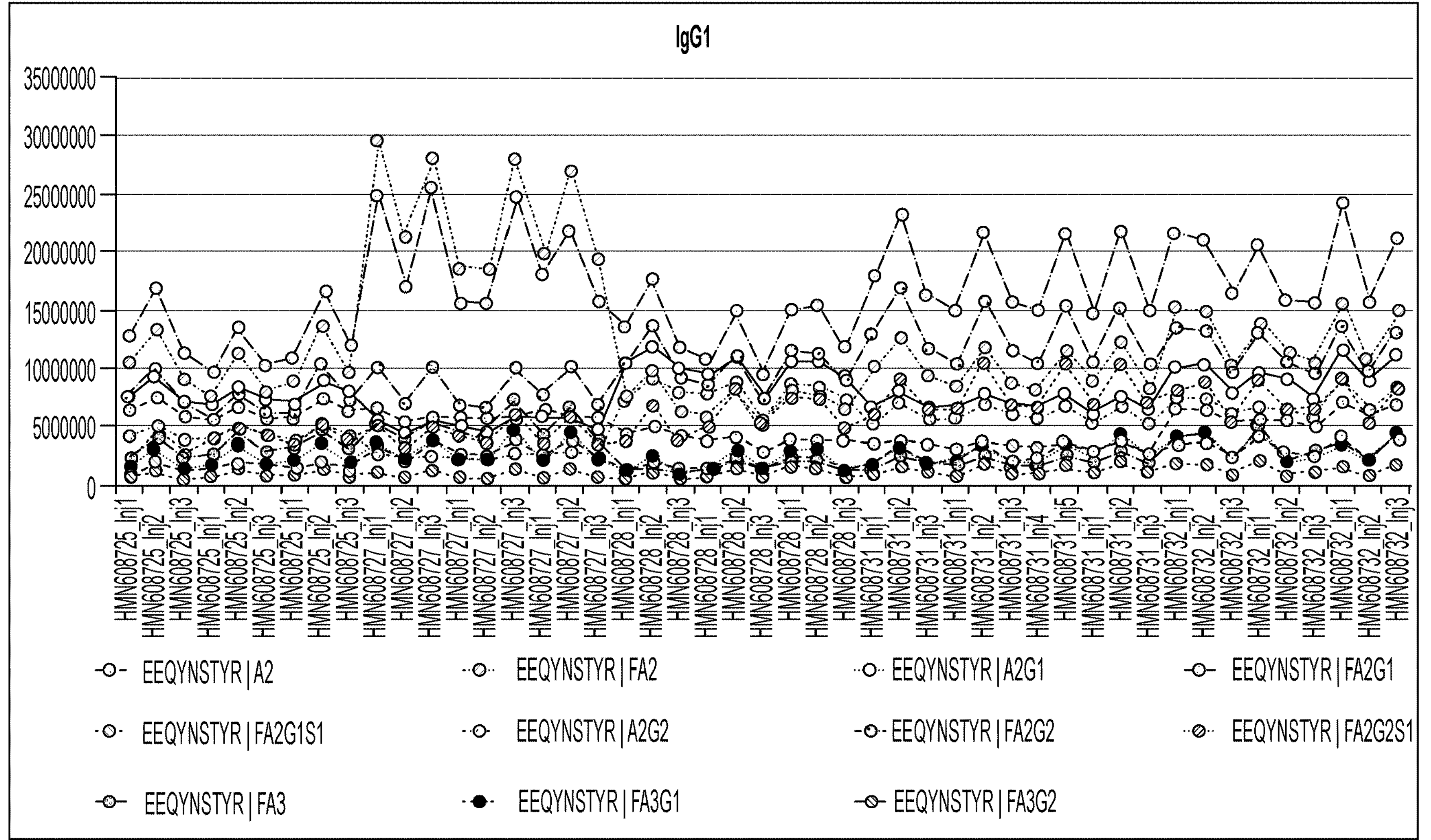
FIG. 17 shows the absolute peak area of Y1 detected for individual glycopeptides from IgG1 that were monitored across different injections for each serum, according to an exemplary embodiment. Each line represents one glycopeptide, indicated at the bottom of the panel.
Figure 18A:
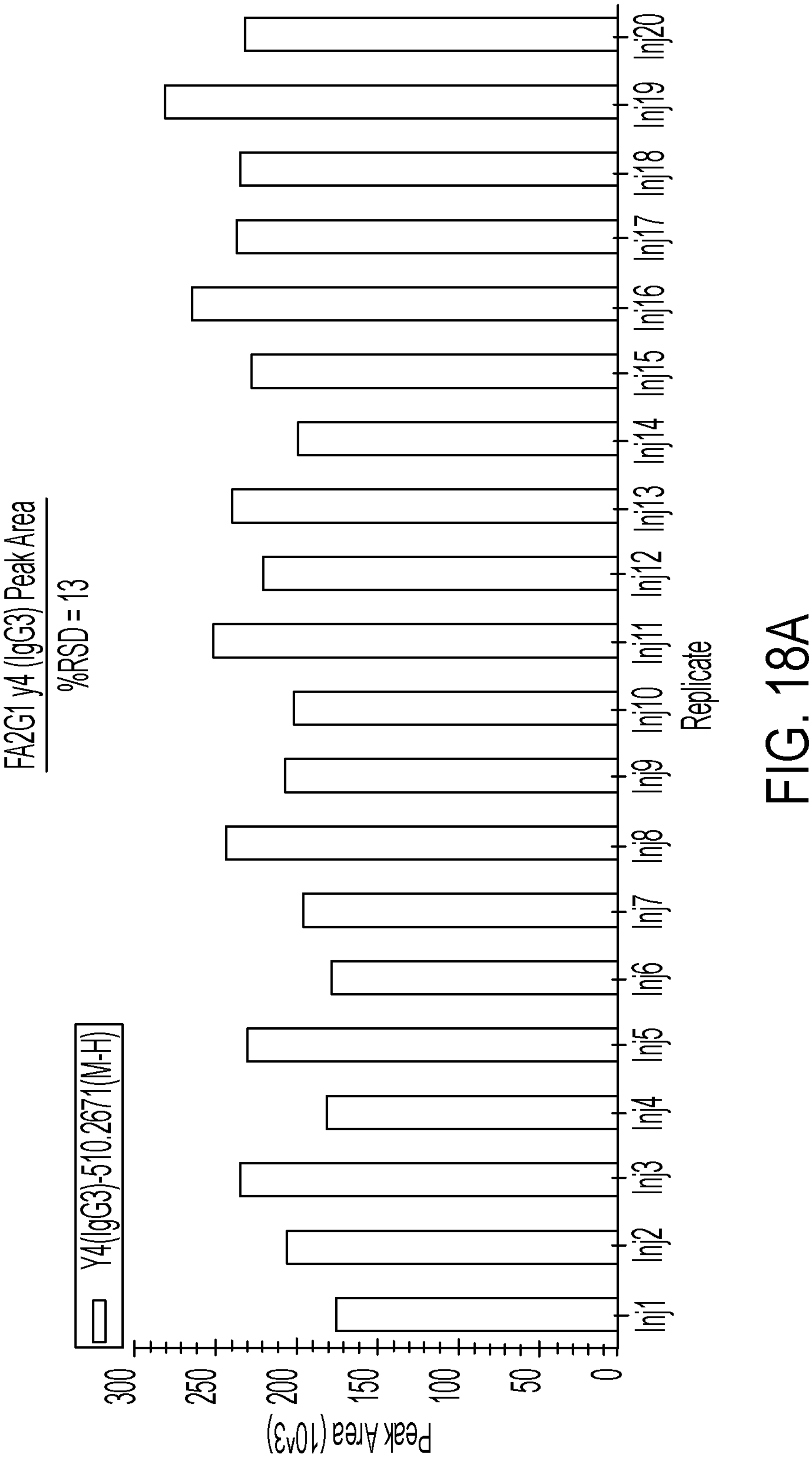
Figure 18B:
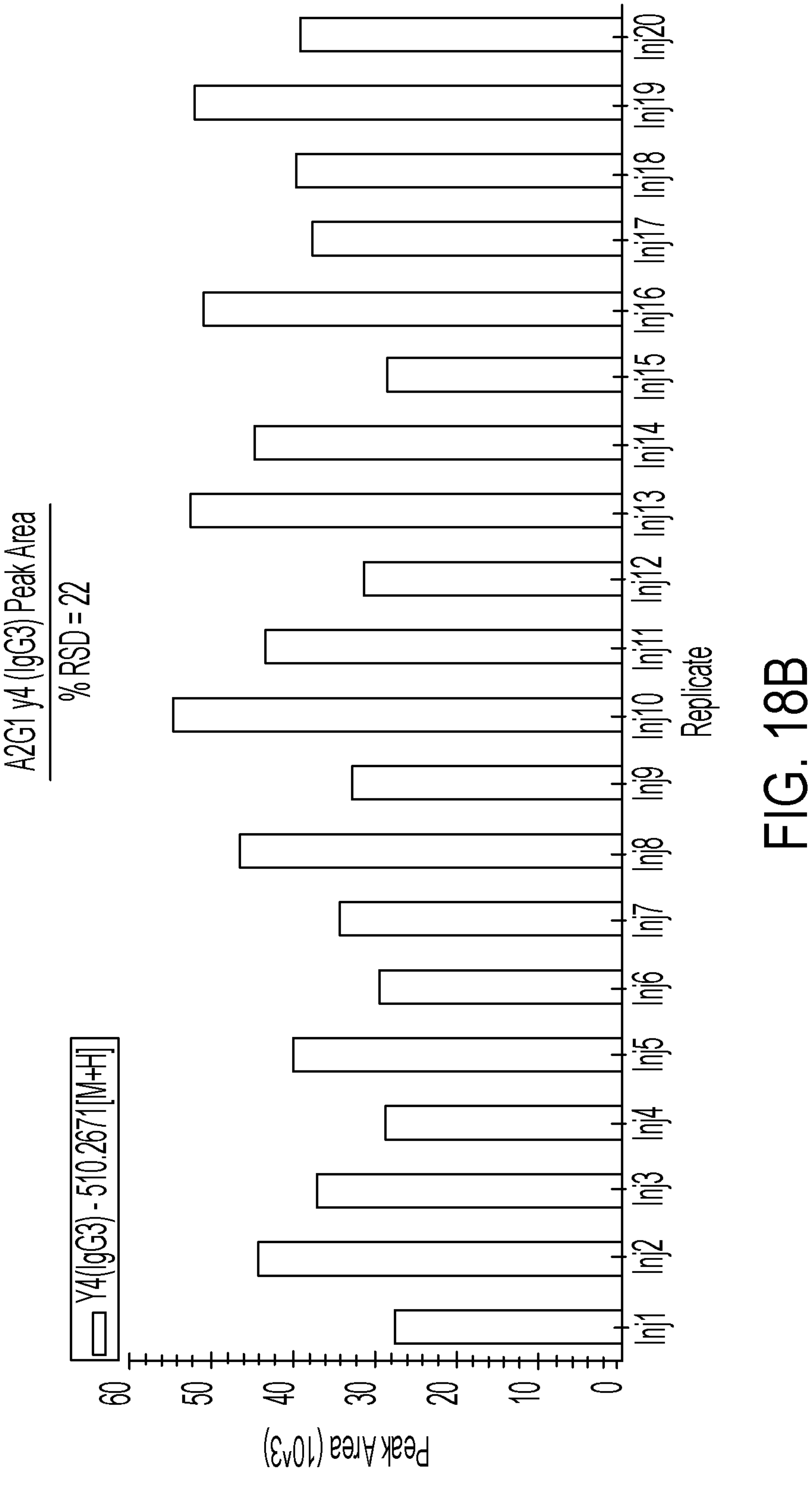
Figure 18C:
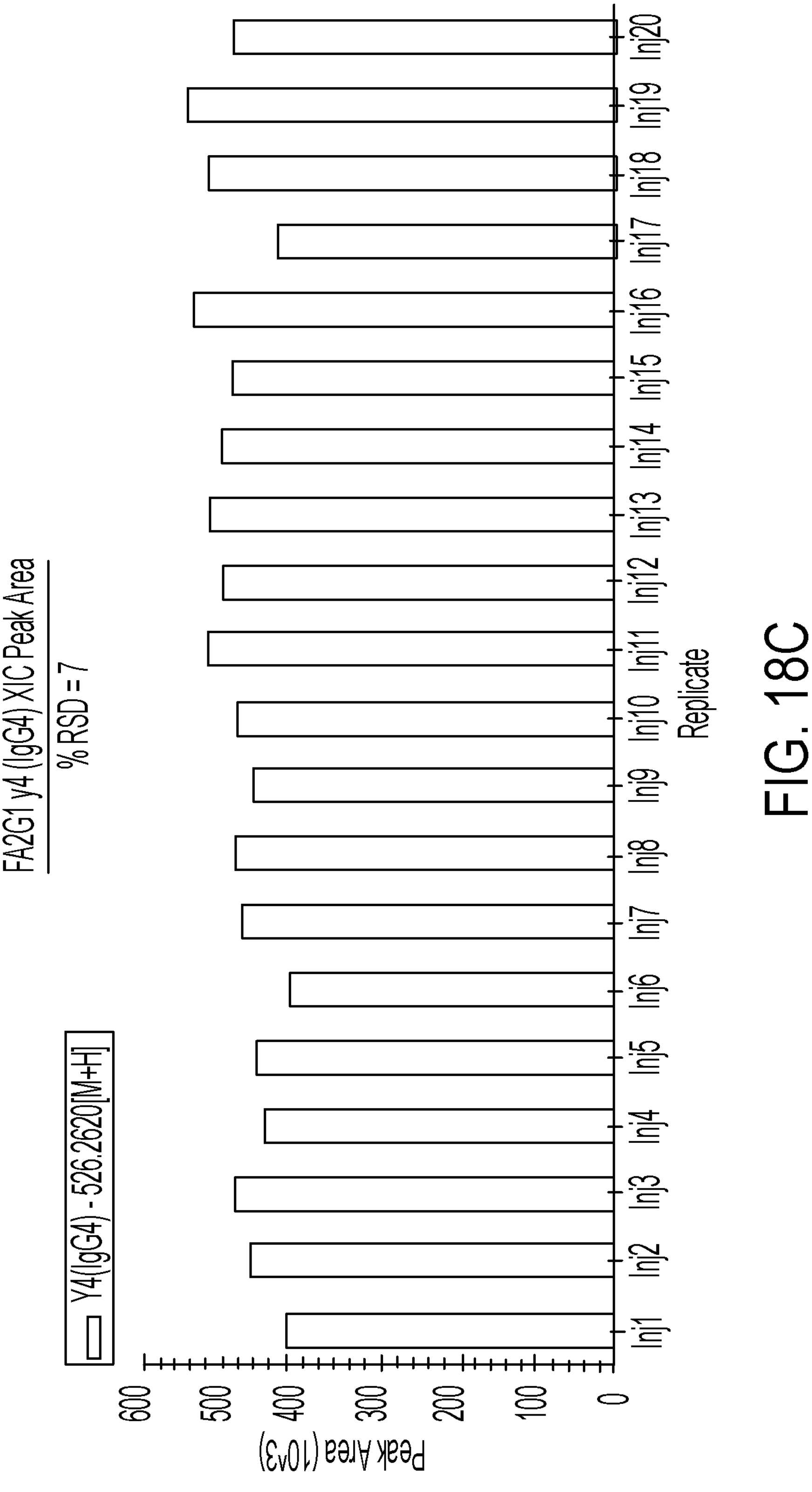
Figure 18D:
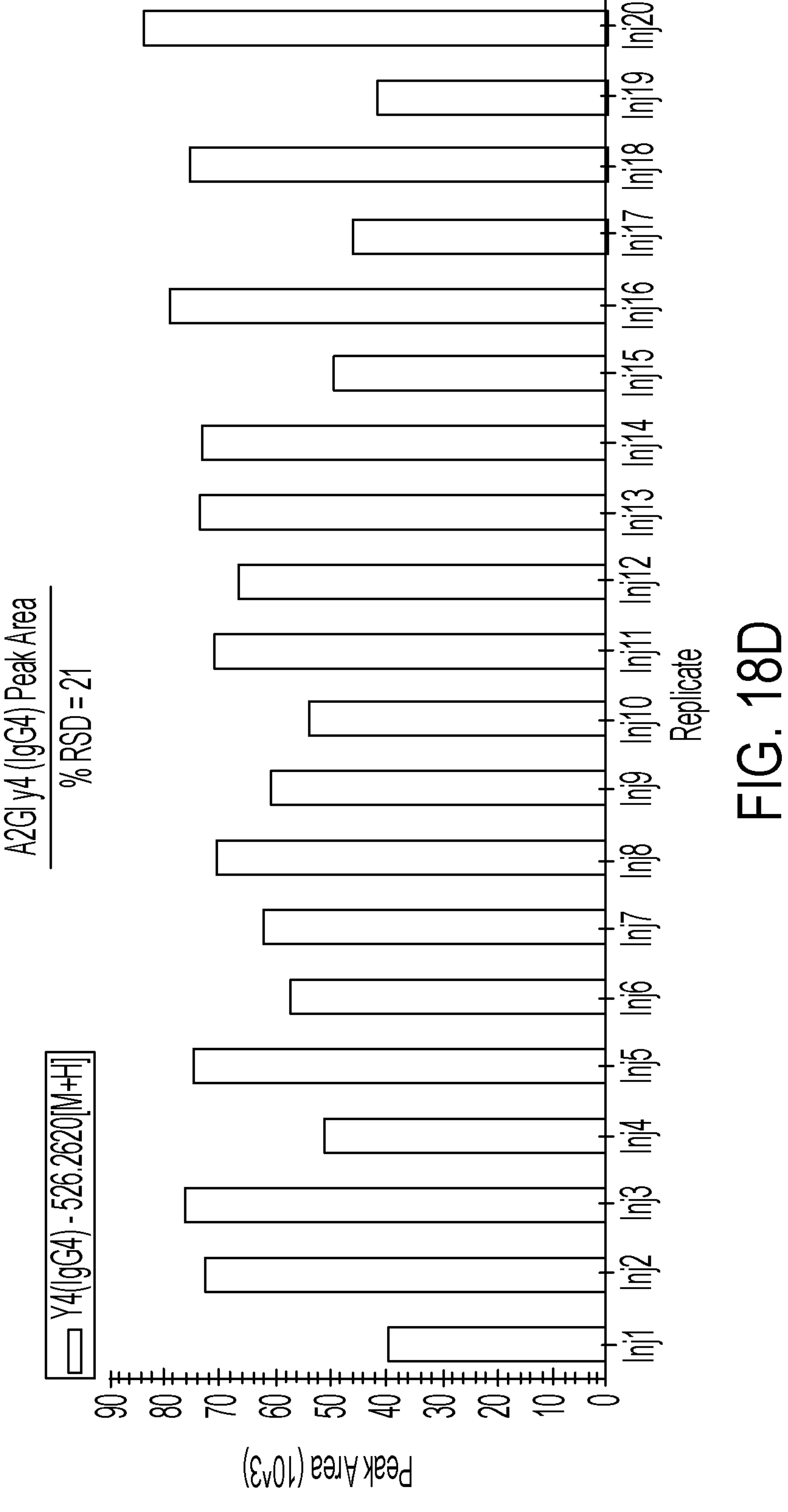
Figure 18E:
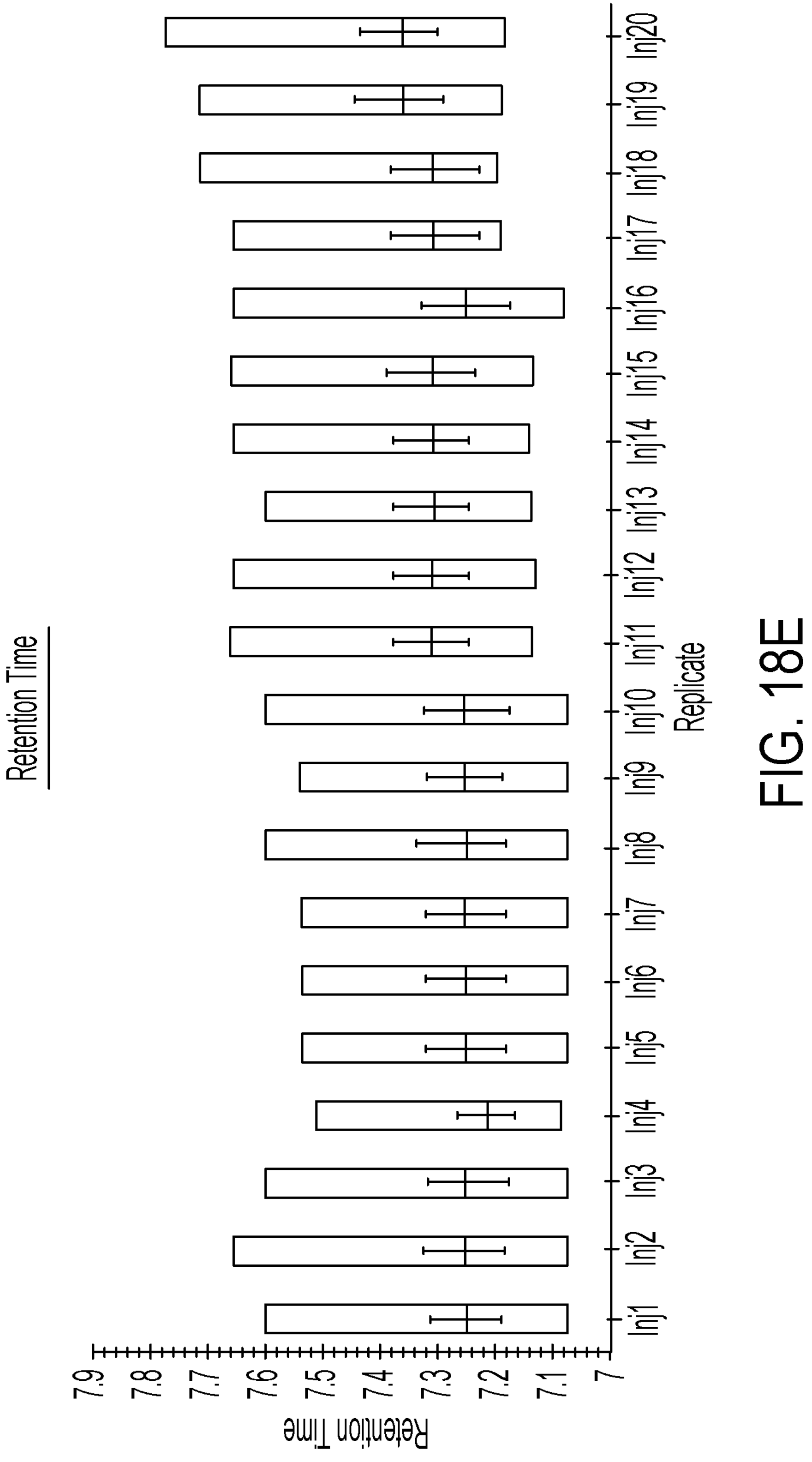

The absolute peak intensities of IgG glycopeptides, including IgG3 and IgG4 glycopeptides, were stable across different injections, despite prolonged experimentation, even though IgG3 and IgG4 glycopeptides were most likely to be affected by signal variation (e.g., due to the relatively low intrinsic protein level compared to IgG1 and IgG2 and indirect measurement of Y1, for which the variation comprised the accumulated variation of total Y1, y4 of IgG3, and y4 of IgG4). FIG. 16B shows that, although Y1 from either IgG3 or IgG4 exhibited noticeable signal variation (average % RSD was about 40%) within the same sample, the intra-sample variations were smaller than the inter-sample differences with respect to the variation of total glycopeptide level (protein level), as well as the switch of dominant glycoforms across individual samples or between IgG subclasses. For example, the total intensity of glycopeptides from IgG4 was greater than that from IgG3 for HMN608725, HMN608727 and HMN608732. In contrast, HMN608728 exhibited a high level of IgG3 against IgG4. FIG. 17 shows that a low level of either IgG3 or IgG4 was detected, while other IgG subclasses, such as IgG1, remained abundant. FIG. 15A and FIG. 15B shows that FA2 was the dominant glycoform in IgG4 while FA2G1 was the dominant glycoform in IgG3, consistent with the observation in pooled human serum data. The low abundant glycans exhibited a % RSD of less than 20%. No obvious retention time shift was observed. This may highlight the advantage of microflow LC over nanoflow LC. The system robustness was further evaluated by 20 continuous runs of the digested pooled normal human serum (Vendor 1). FIG. 18A-18F shows that the system exhibited a negligible retention time shift (less than 0.3 minutes) and relatively stable peak intensity for given high-abundance (% RSD less than 13) or low abundance (% RSD less than 25%) glycopeptides.

Figure 16C:
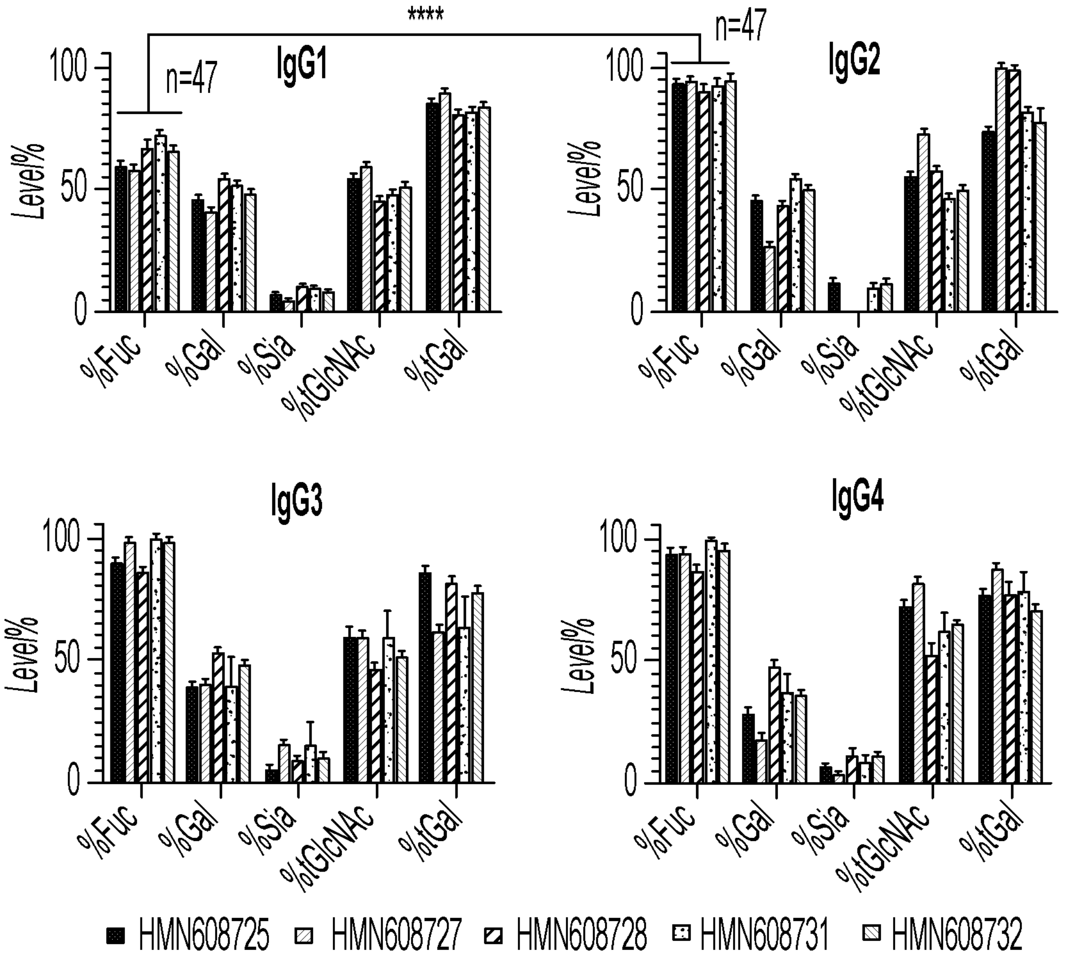
FIG. 16C shows the glycan traits calculated for each IgG subclass and individual serum based on the peak area of Y1 detected in 9 injections (11 injections for sample HMN608731), according to an exemplary embodiment. For IgG3 in HMN609731, data from some injections were subject to be excluded due to the poor signals. Wilcoxon test was performed between the IgG1 and IgG2 for % Fuc. The asterisk indicates significant difference between two groups (p-value <0.0001).

The variations in absolute peak intensity within multiple injections of the same sample had minimal impact on determination of relative percentage of individual glycoforms, as well as the glycan traits. From the same dataset, the variation of each glycan trait across different injections was very limited, as indicated by the small error bars in FIG. 16C, except for IgG3 and IgG4 in HMN608731 due to the failure of signal detection, as shown in FIG. 16B. The results revealed that IgG N-glycosylation profiles varied considerably between individuals, which may be associated with the gender, age, and other factors. Despite the variation from individuals, the difference between IgG subclasses were still able to be captured for certain glycan traits. For instance, % Fuc in IgG1 was significantly lower than that in IgG2 (p-value less than 0.0001) as well as IgG3 or IgG4, quantified within each group of total 47 replicates, which was consistent with the observation in pooled human serum data shown in FIGS. 15A-B and Tables 11-18.

What is claimed is:

1. A method of identifying an N-glycan profile of a protein in a sample, comprising:
- enriching the sample using an affinity chromatography column to generate an enriched sample;
- contacting the enriched sample with one or more proteases to obtain a digested sample, wherein the digested sample comprises one or more peptides;
- loading the digested sample with a liquid chromatography column to provide an eluent;
- performing a multiple reaction monitoring on at least a portion of the eluent to obtain peptide backbone fragments using collision energy in a mass spectrometer; and
- analyzing the peptide backbone fragments to identify the N-glycan profile of the protein.

2. The method of claim 1, wherein the eluent is introduced in the mass spectrometer using a multi-nozzle electrospray emitter.

3. The method of claim 2, wherein the multi-nozzle electrospray emitter has at least 5 channels.

4. The method of claim 3, wherein the multi-nozzle electrospray emitter emits an electrospray of less than about 1 μL/min at a tip of each of the channels.

5. The method of claim 2, wherein a tip of each nozzle of the multi-nozzle electrospray emitter has a diameter of about 10 μm.

6. The method of claim 1, further comprising denaturing the sample before contacting the sample with one or more proteases.

7. The method of claim 1, further comprising reducing the sample before contacting the sample with one or more proteases.

8. The method of claim 1, further comprising alkylating the sample before contacting the sample with one or more proteases.

9. The method of claim 1, wherein flowrate for the liquid chromatography column is about 5 μL/min.

10. The method of claim 1, wherein the sample is at least about 5 μL in volume.

11. The method of claim 1, wherein the affinity chromatography column comprises immobilized protein A, immobilized protein G, or combination of immobilized protein A and immobilized protein G.

12. The method of claim 1, wherein enriching the sample using the affinity chromatography column includes:
- adding a kosmotropic salt to the sample;
- loading the sample onto the affinity chromatography column;
- introducing a wash buffer to the affinity chromatography column; and
- introducing an elution buffer to the affinity chromatography column.

13. A method for identifying a glycosylated peptide biomarker in a sample, comprising:
- loading the sample on an affinity chromatography column;
- eluting an eluate from the affinity chromatography column;
- contacting the eluate with one or more proteases to obtain a digested sample, wherein the digested sample comprises one or more peptides;
- loading the digested sample with a liquid chromatography column to provide an eluent;
- performing a multiple reaction monitoring on at least a portion of the eluent to obtain peptide backbone fragments using collision energy in a mass spectrometer; and
- analyzing the peptide backbone fragments to identify the glycosylated peptide biomarker.

14. The method of claim 13, wherein the eluent is introduced in the mass spectrometer using a multi-nozzle electrospray emitter.

15. The method of claim 14, wherein the multi-nozzle electrospray emitter has at least 5 channels.

16. The method of claim 15, wherein the multi-nozzle electrospray emitter emits an electrospray of less than about 1 μL/min at a tip of each of the channels.

17. The method of claim 14, wherein a tip of each nozzle of the multi-nozzle electrospray emitter has a diameter of about 10 μm.

18. The method of claim 13, further comprising denaturing the sample before contacting the sample with one or more proteases.

19. The method of claim 13, further comprising reducing the sample before contacting the sample with one or more proteases.

20. The method of claim 13, further comprising alkylating the sample before contacting the sample with one or more proteases.

21. The method of claim 13, wherein flowrate for the liquid chromatography column is about 5 μL/min.

22. The method of claim 13, wherein the sample is at least about 5 μL in volume.

23. The method of claim 13, wherein the affinity chromatography column comprises immobilized protein A, immobilized protein G, or combination of immobilized protein A and immobilized protein G.

24. The method of claim 13, further comprising:
- prior to loading the sample on the affinity chromatography column, adding a kosmotropic salt to the sample such that a concentration of the kosmotropic salt in the sample is about 0.3 M to about 1.1 M; and
- after eluting the eluate from the affinity chromatography column, desalting the sample.

* * * * *